(12) United States Patent
Kim

(10) Patent No.: US 10,561,385 B2
(45) Date of Patent: *Feb. 18, 2020

(54) X-RAY IMAGING APPARATUS AND CONTROL METHOD THEREOF

(71) Applicant: Samsung Electronics Co., Ltd., Suwon-si (KR)

(72) Inventor: Myeong Je Kim, Seoul (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 334 days.

This patent is subject to a terminal disclaimer.

(21) Appl. No.: 15/613,771

(22) Filed: Jun. 5, 2017

(65) Prior Publication Data

US 2017/0265827 A1 Sep. 21, 2017

Related U.S. Application Data

(63) Continuation of application No. 14/555,907, filed on Nov. 28, 2014, now Pat. No. 9,675,309.

(30) Foreign Application Priority Data

Nov. 28, 2013 (KR) .................. 10-2013-0145963
Nov. 26, 2014 (KR) .................. 10-2014-0166254

(51) Int. Cl.
*H05G 1/08* (2006.01)
*A61B 6/00* (2006.01)
*G01T 1/175* (2006.01)

(52) U.S. Cl.
CPC .......... *A61B 6/4494* (2013.01); *A61B 6/4266* (2013.01); *A61B 6/547* (2013.01); *A61B 6/566* (2013.01); *G01T 1/175* (2013.01)

(58) Field of Classification Search
CPC ......... A61B 6/00; A61B 6/566; A61B 6/4494; A61B 6/44; A61B 6/54; A61B 6/547;
(Continued)

(56) References Cited

U.S. PATENT DOCUMENTS 8,848,872 B2   9/2014   Lee
9,675,309 B2 *  6/2017  Kim ..................... A61B 6/4266
(Continued)

FOREIGN PATENT DOCUMENTS

EP      2 543 318 A1     1/2013

OTHER PUBLICATIONS

European Intention to Grant dated Mar. 8, 2018 in corresponding European Patent Application No. 14 195 182.2, 95 pgs.
(Continued)

*Primary Examiner* — Jurie Yun
(74) *Attorney, Agent, or Firm* — Staas & Halsey LLP

(57) ABSTRACT

An X-ray imaging apparatus includes an X-ray source to generate and irradiate X-rays; an X-ray detector installed in at least one module of one or more modules, to detect the irradiated X-rays; an Identification (ID) resistor included in the module; a port included in the X-ray detector; and a controller to determine a module in which the X-ray detector has been installed, using the ID resistor and the port. The controller may assign a static Information Provider (IP) address to the module, and determine a module in which the X-ray detector has been installed, based on the static IP address. According to the X-ray imaging apparatuses and a control method thereof, it is possible to determine an installation location of the X-ray detector, and to use the X-ray detector in various modules without having to provide separate X-ray detectors for different locations.

15 Claims, 42 Drawing Sheets

(58) Field of Classification Search
CPC ..... A61B 6/4266; A61B 6/4411; A61B 6/587;
G01T 1/2928; G01T 1/175
USPC .................. 378/91, 98.8, 116, 204, 205, 210
See application file for complete search history.

(56) References Cited

U.S. PATENT DOCUMENTS

| | | |
|---|---|---|
| 2007/0140424 A1 | 6/2007 | Serceki |
| 2009/0257564 A1 | 10/2009 | Kito et al. |
| 2010/0169423 A1 | 7/2010 | Eguchi |
| 2011/0254563 A1 | 10/2011 | Liu et al. |
| 2012/0166607 A1 | 6/2012 | Kitano et al. |
| 2013/0038738 A1 | 2/2013 | Ando et al. |
| 2013/0127613 A1 | 5/2013 | Zhang et al. |
| 2013/0168568 A1 | 7/2013 | Watanabe |
| 2015/0146862 A1* | 5/2015 | Kim ...................... G01T 1/2018 378/91 |

OTHER PUBLICATIONS

Extended European Search Report dated Mar. 27, 2015 for corresponding European Patent Application No. 14195182.2.
International Search Report dated Feb. 26, 2015 for corresponding International Patent Application No. PCT/KR2014/011505.
U.S. Notice of Allowance dated Feb. 7, 2017 in U.S. Appl. No. 14/555,907.
U.S. Office Action dated Aug. 25, 2016 in U.S. Appl. No. 14/555,907.
U.S. Appl. No. 14/555,907, filed Nov. 28, 2014, Myeong Je Kim, Samsung Electronics Co., Ltd.

\* cited by examiner

FIG. 8
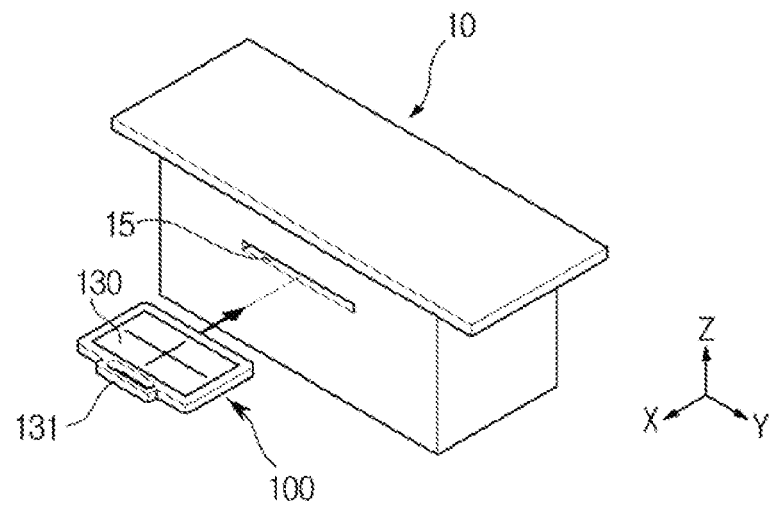
(a)
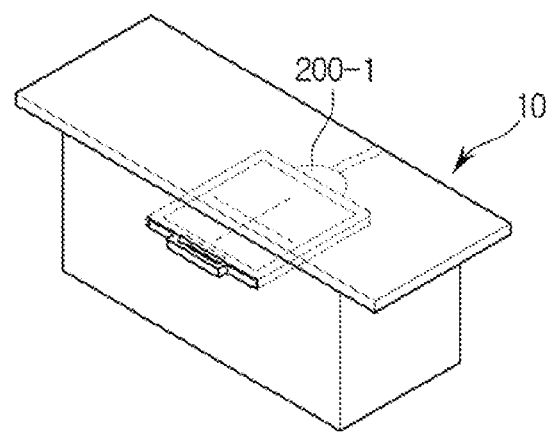
(b)

FIG. 9
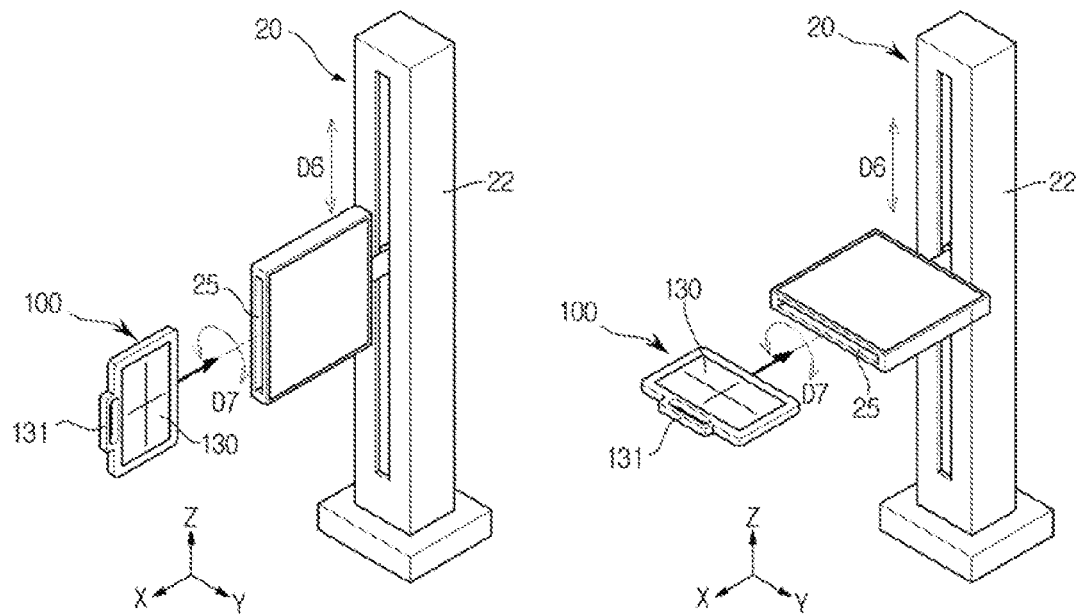
(a)
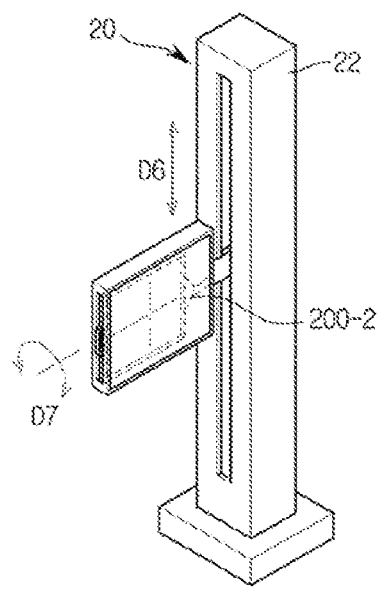
(b)

FIG. 11
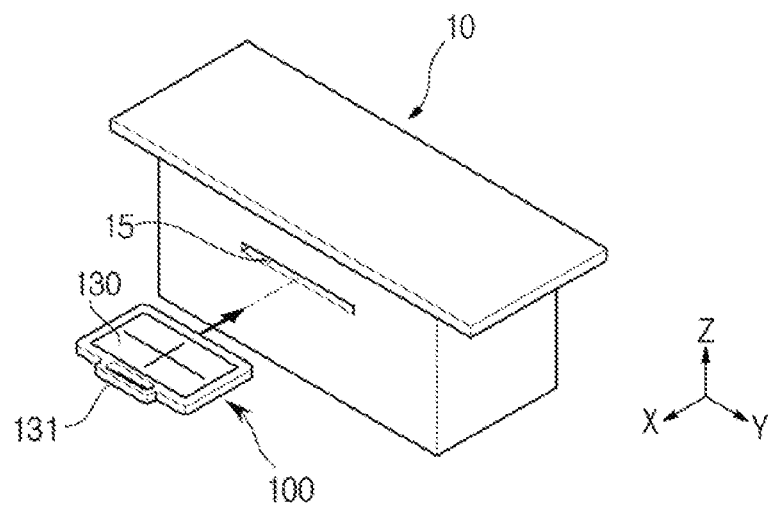
(a)
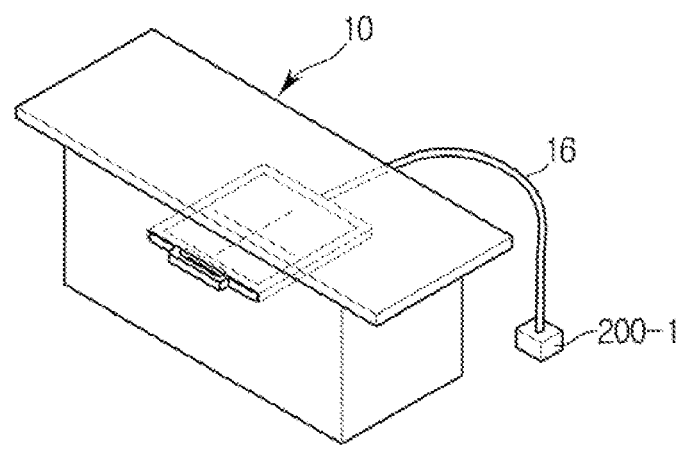
(b)

FIG. 12
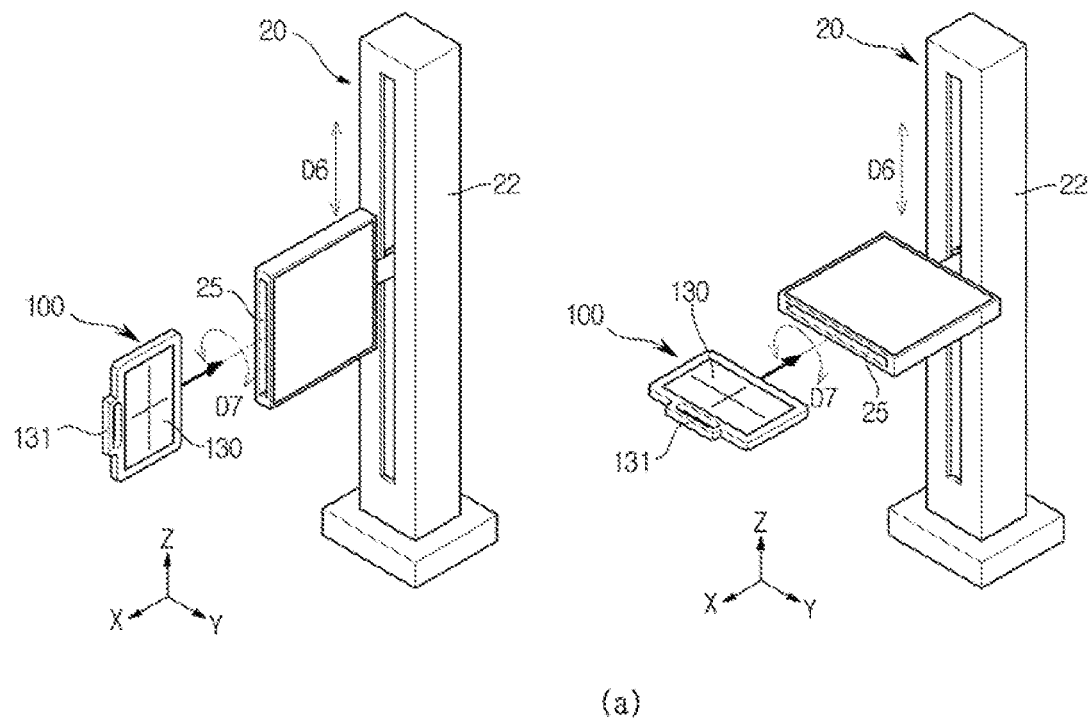
(a)
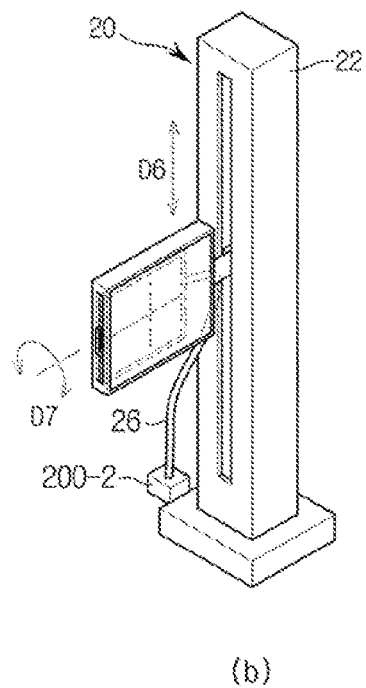
(b)

FIG. 20

| DETECTOR | UNIQUE IP OF DETECTOR |
|---|---|
| FIRST X-RAY DETECTOR (100-1) | 192.168.0.1 |
| SECOND X-RAY DETECTOR (100-2) | 192.168.0.2 |
| THIRD X-RAY DETECTOR (100-3) | 192.168.0.3 |

FIG. 21

|  | Voltage Level | ADC Level | UNIQUE IP OF DETECTOR | | |
|---|---|---|---|---|---|
| TABLE MODE | $V_{11}$ | 255 | 192.168.0.1 | W/S | ~170 |
| STAND MODE | $V_{12}$ | 170 | 192.168.0.2 | W/S | ~170 |
| PORTABLE MODE | $V_{13}$ | 127 | 192.168.0.3 | W/S | ~170 |

FIG. 22

|  | Voltage Level | ADC Level | IP OF DETECTOR |
|---|---|---|---|
| TABLE MODE | $V_{11}$ | 255 | 192.168.0.1 |
| STAND MODE | $V_{12}$ | 170 | 192.168.0.2 |
| PORTABLE MODE | $V_{13}$ | 127 | 192.168.0.3 |

FIG. 29

| | Voltage Level | | GPIO Level | | UNIQUE IP OF DETECTOR | |
|---|---|---|---|---|---|---|
| TABLE MODE | $V_{21}$ | $V_{21}$ | High | High | 192.168.0.1 | → W/S ~170 |
| STAND MODE | $V_{21}$ | $V_{22}$ | High | Low | 192.168.0.2 | → W/S ~170 |
| PORTABLE MODE | $V_{22}$ | $V_{22}$ | Low | Low | 192.168.0.3 | → W/S ~170 |

FIG. 30

|  | Voltage Level | | GPIO Level | | IP OF DETECTOR |
|---|---|---|---|---|---|
| TABLE MODE | $V_{21}$ | $V_{21}$ | High | High | 192.168.0.1 |
| STAND MODE | $V_{21}$ | $V_{22}$ | High | Low | 192.168.0.2 |
| PORTABLE MODE | $V_{22}$ | $V_{22}$ | Low | Low | 192.168.0.3 |

X-RAY IMAGING APPARATUS AND CONTROL METHOD THEREOF

CROSS-REFERENCE TO RELATED APPLICATIONS

This application is a Continuation of U.S. application Ser. No. 14/555,907, filed Nov. 28, 2014, which claims the priority benefit of Korean Patent Application No. 10-2013-0145963, filed on Nov. 28, 2013 and Korean Patent Application No. 10-2014-0166254 filed on Nov. 26, 2014 in the Korean Intellectual Property Office, the disclosures of which are incorporated herein by reference.

BACKGROUND

1. Field

The following description relates to an X-ray imaging apparatus of irradiating X-rays onto an object to produce an X-ray image, and a control method of the X-ray imaging apparatus.

2. Description of the Related Art

An X-ray imaging apparatus is equipment for acquiring images of the inside of an object using X-rays. The X-ray imaging apparatus images the inside of an object using a non-invasive method of irradiating X-rays onto the object and detecting X-rays transmitted through the object. Accordingly, a medical X-ray imaging apparatus is used to diagnose an internal injury or a disease of an object that cannot be examined externally.

The X-ray imaging apparatus includes an X-ray source to generate X-rays and to irradiate the X-rays onto an object, and an X-ray detector to detect X-rays transmitted through the object. In order to image various parts of an object, the X-ray source may be configured to be movable. The X-ray detector may be used in a table mode in which the X-ray detector is installed in a radiography table, in a stand mode in which the X-ray detector is installed in a radiography stand, and in a portable mode in which the X-ray detector is not fixed at a specific location. Also, two or more X-ray detectors may be provided in correspondence to a single X-ray source. In this case, if the exact locations of the X-ray detectors cannot be recognized, it may fail to receive image data from an X-ray detector actually used in scanning.

Lately, with digitalization of X-ray imaging apparatuses, X-ray images are acquired digitally instead of on film so that many functions of X-ray imaging apparatuses are automated. Examples of such automation are Auto Tracking of an X-ray source, automatically tracking an X-ray detector, and Auto Centering of automatically centering the locations of the X-ray source and the X-ray detector. In order to implement automation functions of an X-ray imaging apparatus, such as Auto Tracking or Auto Centering, and prevent rescanning, it is necessary to accurately determine which X-ray detector operates at which location.

SUMMARY

Therefore, it is an aspect of the present disclosure to provide an X-ray imaging apparatus capable of determining a location of an X-ray detector, and determining, if a plurality of X-ray detectors have been provided, which X-ray detector is positioned at which location.

Additional aspects of the disclosure will be set forth in part in the description which follows and, in part, will be obvious from the description, or may be learned by practice of the disclosure.

In accordance with an aspect of the present disclosure, an X-ray imaging apparatus may include: an X-ray source configured to generate and irradiate X-rays; at least one X-ray detector configured to detect the irradiated X-rays; at least one coupling module including an electric device configured to generate an electrical signal according to whether the X-ray detector has been coupled; and a controller configured to determine a coupling module with which the X-ray detector has been coupled among the at least one coupling module, based on the electrical signal.

The electric device may include an IDentification (ID) resistor to identify the coupling module.

The coupling module may correspond to a radiography mode among radiography modes including a table mode, a stand mode, and a portable mode.

A plurality of X-ray detectors and a plurality of coupling modules may be provided, and wherein the controller may determine which X-ray detector of the plurality of X-ray detectors has been coupled with which coupling module of the plurality of coupling modules.

Each coupling module may connect to the controller and a power supply unit.

The coupling module with which the X-ray detector has been coupled may supply a supply voltage to the coupled X-ray detector, and enable communications between the coupled X-ray detector and the controller.

The X-ray detector may include an Analog-Digital Converter (ADC) port.

ID resistors having different resistance values may be respectively included in the coupling modules.

The ADC port may monitor a voltage generated in correspondence to the ID resistor of the coupling module coupled with the X-ray detector, and output a digital value corresponding to a level of the voltage to the controller.

The coupled X-ray detector may transmit the digital value and a unique IP address of the X-ray detector to the controller.

The controller may determine the coupled X-ray detector based on the received unique IP address, and determine the coupling module with which the X-ray detector has been coupled, based on the received digital value.

The X-ray detector may include at least one General Purpose Input/Output (GPIO) port.

At least one ID resistor may be provided to one-to-one match the number of the GPIO port.

The at least one ID resistor may have the same resistance value.

Each of the at least one ID resistor may be a pull-up resistor or a pull-down resistor.

Different ordered pairs of ID resistors may be respectively included in different coupling modules.

Each of the at least GPIO port may monitor a voltage in correspondence to an ID resistor matching the corresponding port among at least one ID resistor of a coupling module with which the X-ray detector has been coupled, and output a relative level of the voltage to the controller.

The coupled X-ray detector may transmit the relative level of the voltage and a unique IP address of the X-ray detector to the controller.

The controller may determine the coupled X-ray detector, based on the unique IP address, and determine the coupling module with which the X-ray detector has been coupled, based on the relative level of the voltage.

In accordance with another aspect of the present disclosure, an X-ray imaging apparatus includes: an X-ray source configured to generate and irradiate X-rays; at least one X-ray detector configured to detect the irradiated X-rays; at least one coupling module configured to be coupled with the X-ray detector, and having a static Information Provider (IP) address; a controller configured to determine a coupling module with which the X-ray detector has been coupled, among the at least one coupling module, based on the static IP address.

A plurality of X-ray detectors and a plurality of coupling modules may be provided, and the controller may determine which X-ray detector of the plurality of X-ray detectors has been coupled with which coupling module of the plurality of coupling modules.

Each coupling module may connect to the controller and a power supply unit.

A static IP address may be assigned to each of the plurality of coupling modules.

The coupling module with which the X-ray detector has been coupled may supply a supply voltage to the X-ray detector, and enable communications between the X-ray detector and the controller.

The controller may receive the static IP address of the X-ray detector with which the X-ray detector has been coupled, and a unique IP address of the coupled X-ray detector.

The controller may determine the coupled X-ray detector, based on the unique IP address, and determine the coupling module in which the X-ray detector has been coupled, based on the static IP address.

The controller may maintain or change the IP address assigned to the X-ray detector in correspondence with the coupling module in which the X-ray detector has been coupled.

The controller may move the X-ray source to correspond to a location of the X-ray detector.

In accordance with another aspect of the present disclosure, a control method of an X-ray imaging apparatus may include: monitoring, at a monitoring unit included in an X-ray detector, a voltage in correspondence with an Identification (ID) electric device of a coupling module with which the X-ray detector has been coupled; outputting, from the monitoring unit, a data value corresponding to the voltage; and determining the coupling module with which the X-ray detector has been coupled, based on the data value.

In accordance with another aspect of the present disclosure, a control method of an X-ray imaging apparatus may include: assigning a static Information Provider (IP) address to at least one coupling module; receiving a static IP address of the coupling module in which an X-ray detector has been coupled; and determining the coupling module with which the X-ray detector has been coupled, based on the received static IP address.

The control method may further include maintaining or changing an IP address assigned to the X-ray detector in correspondence to the coupling module with which the X-ray detector has been coupled.

The control method may further include moving the X-ray source to correspond to a location of the X-ray detector.

According to the X-ray imaging apparatuses and the control methods thereof, it is possible to determine a location of the X-ray detector, and to determine, if a plurality of X-ray detectors have been provided, which X-ray detector is positioned at which location. Accordingly, a user does not need to designate an X-ray detector to be used in scanning, unnecessary rescanning may be prevented, and multi-use of an X-ray detector is possible.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 8 is a view for describing a method in which an X-ray detector is installed in a radiography table;

FIG. 9 is a view for describing a method in which an X-ray detector is installed in a radiography stand;

FIGS. 11 to 13 show exemplary locations of a table coupling module, a stand coupling module, and a portable coupling module;

FIGS. 20 and 21 show information that a location determiner uses to determine a location of an X-ray detector when the X-ray detector has a unique IP address;

FIG. 22 is a view for describing an example of a method of assigning an Information Provider (IP) address to an X-ray detector and an example of a method of changing an IP address of the X-ray detector;

FIG. 29 shows an example of information which a location determiner uses to determine a location of an X-ray detector in the example of FIG. 28;

FIG. 30 is a view for describing a method of assigning an IP address to an X-ray detector and a method of changing an IP address of the X-ray detector;

DETAILED DESCRIPTION

Figure 1:
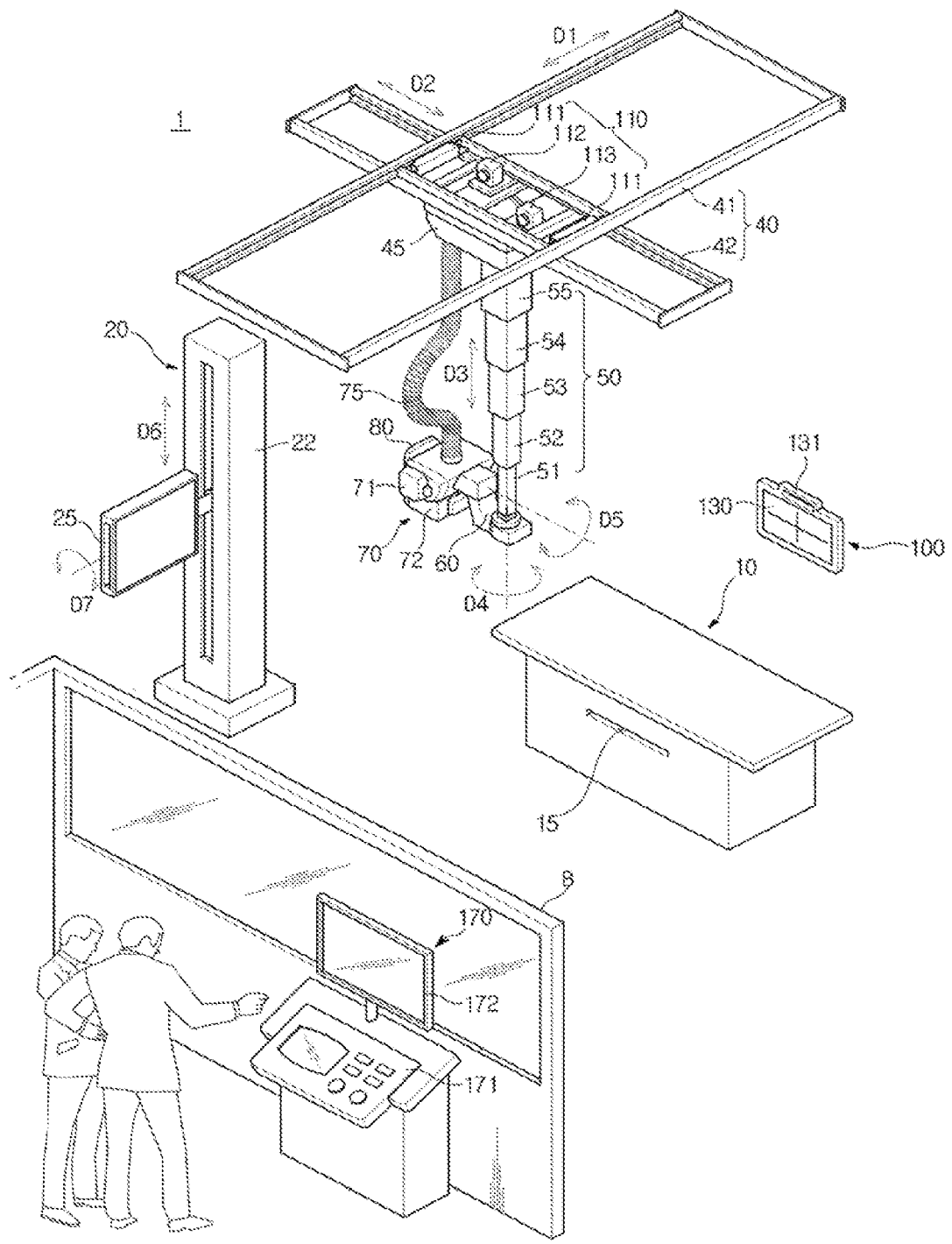
FIG. 1 is a perspective view of an X-ray imaging apparatus according to an embodiment of the present disclosure.

Reference will now be made in detail to the embodiments of the present disclosure, examples of which are illustrated in the accompanying drawings, wherein like reference numerals refer to like elements throughout.

Hereinafter, an X-ray imaging apparatus and a control method thereof according to embodiments of the present disclosure will be described in detail with reference to the accompanying drawings.

Figure 2:
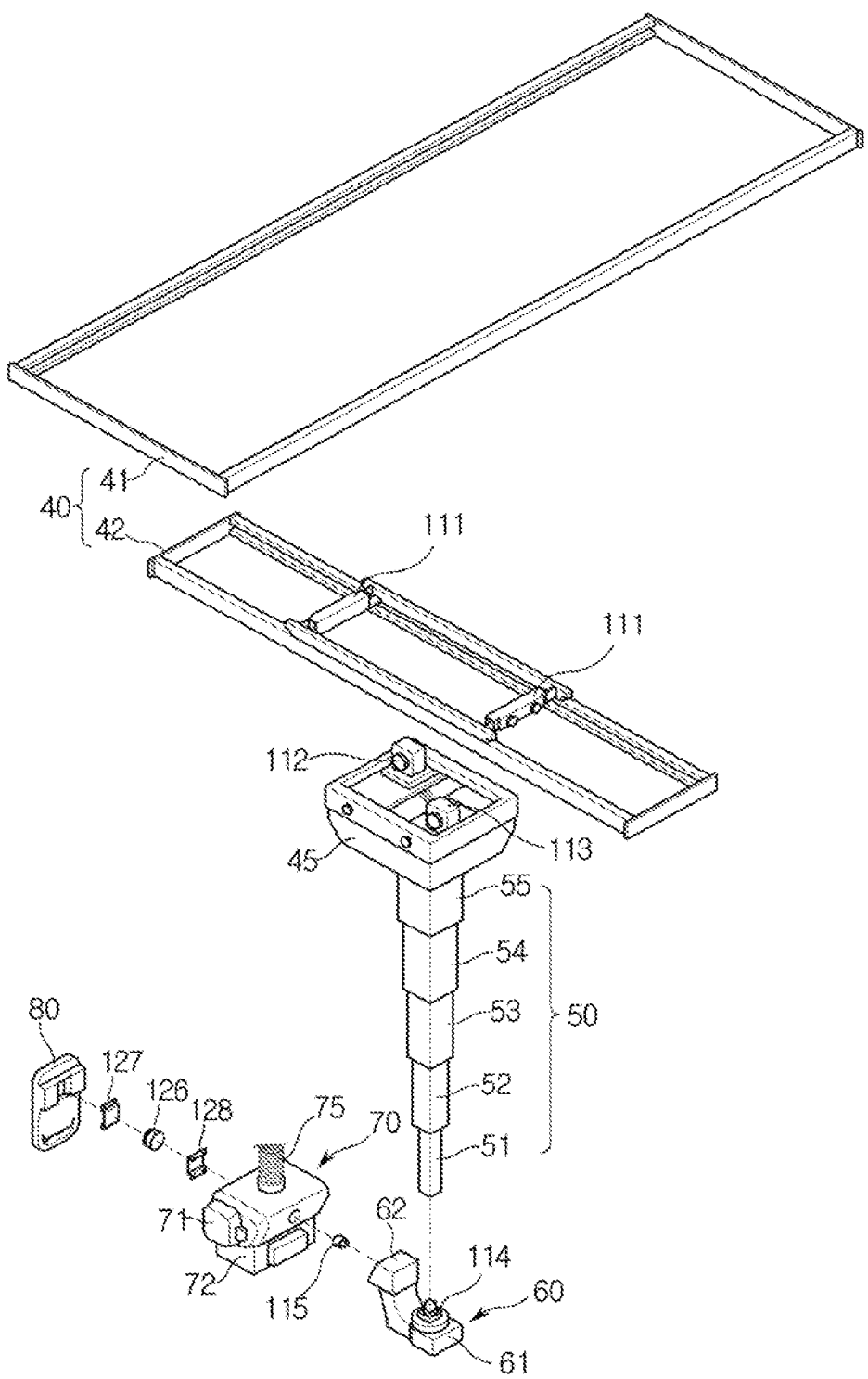
FIG. 2 is an exploded perspective view of an X-ray imaging apparatus according to an embodiment of the present disclosure.
Figure 3:
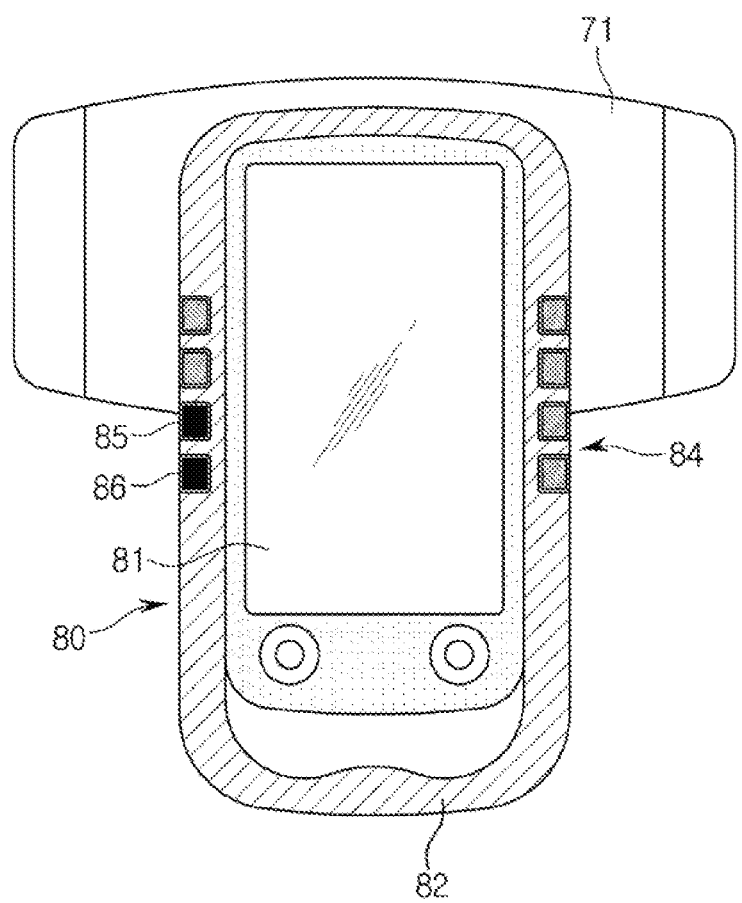
FIG. 3 is a front view of an operating unit of an X-ray imaging apparatus, according to an embodiment of the present disclosure.

FIG. 1 is a perspective view of an X-ray imaging apparatus according to an embodiment of the present disclosure, FIG. 2 is an exploded perspective view of an X-ray imaging apparatus according to an embodiment of the present disclosure, and FIG. 3 is a front view of an operating unit of an X-ray imaging apparatus, according to an embodiment of the present disclosure.

Referring to FIGS. 1, 2, and 3, an X-ray imaging apparatus 1 may include a guide rail unit 40, a carriage 45, a post frame 50, a motor unit 110, an X-ray source 70, an X-ray detector 100, an operating unit 80, and a workstation 170. The X-ray imaging apparatus 1 may further include a radiography table 10 and a radiography stand 20 in which the X-ray detector 100 can be installed.

The guide rail unit 40, the carriage 45, and the post frame 50 are used to move the X-ray source 70 toward an object.

The guide rail unit 40 may include a first guide rail 41 and a second guide rail 42 arranged to form a predetermined angle with respect to each other. The first guide rail 41 may be orthogonal to the second guide rail 42.

The first guide rail 41 may be installed on a ceiling of an examination room where a radiography apparatus is placed.

The second guide rail 42 may be disposed beneath the first guide rail 41, and slide with respect to the first guide rail 41. The first guide rail 41 may include a plurality of rollers (not shown) that are movable along the first guide rail 41. The second guide rail 42 may connect to the rollers and move along the first guide rail 41.

A direction in which the first guide rail 41 extends is defined as a first direction D1, and a direction in which the second guide rail 42 extends is defined as a second direction D2. Accordingly, the first direction D1 may be orthogonal to the second direction D2, and the first and second directions D1 and D2 may be parallel to the ceiling of the examination room.

The carriage 45 may be disposed beneath the second guide rail 42, and move along the second guide rail 42. The carriage 45 may include a plurality of rollers (not shown) to move along the second guide rail 42. Accordingly, the carriage 45 is movable in the first direction D1 together with the second guide rail 42, and movable in the second direction D2 along the second guide rail 42. The post frame 50 may be fixed on the carriage 45 and disposed below the carriage 45. The post frame 50 may include a plurality of posts 51, 52, 53, 54, and 55.

The posts 51, 52, 53, 54, and 55 may connect to each other such that they can be folded with each other. The length of the post frame 50 fixed on the carriage 45 may increase or decrease in the elevation direction of the examination room.

A direction in which the length of the post frame 50 increases or decreases is defined as a third direction D3. Accordingly, the third direction D3 may be orthogonal to the first direction D1 and the second direction D2.

The X-ray source 70 may irradiate X-rays to an object. Herein, the object may be a human's or animal's living body, however, the object is not limited to these. That is, the object may be anything whose inside structure can be imaged by the X-ray imaging apparatus 1.

The X-ray source 70 may include an X-ray tube 71 to generate X-rays, and a collimator 72 to guide the generated X-rays to be headed toward an object. The X-ray tube 71 will be described in more detail, later.

A revolute joint 60 may be disposed between the X-ray source 70 and the post frame 50.

The revolute joint 60 may couple the X-ray source 70 with the post frame 50, and support a load applied to the X-ray source 70.

The revolute joint 60 may include a first revolute joint 61 connected to the lower post 51 of the post frame 50, and a second revolute joint 62 connected to the X-ray source 70.

The first revolute joint 61 is rotatable with respect to the central axis of the post frame 50 extending in the elevation direction of the examination room. Accordingly, the first revolute joint 61 may rotate on a plane that is perpendicular to the third direction D3. The rotation direction of the first revolute joint 61 is defined as a fourth direction D4, and the fourth direction D4 is a rotation direction of an axis parallel to the third direction D3.

The second revolute joint 62 is rotatable on a plane that is perpendicular to the ceiling of the examination room. Accordingly, the second revolute joint 62 may rotate in a rotation direction of an axis parallel to the first direction D1 and the second direction D2. The rotation direction of the second rotation joint 62 is defined as a fifth direction D5, and the fifth direction D5 is a rotation direction of an axis extending in the first direction D1 or the second direction D2. The X-ray source 70 may connect to the revolute joint 60 and rotate in the fourth direction D4 and the third direction D5. Also, the X-ray source 70 may connect to the post frame 50 through the revolute joint 60, and linearly move in the first direction D1, in the second direction D2, or in the third direction D3.

In order to move the X-ray source 70 in the first direction D1 through the fifth direction D5, the motor unit 110 is used. The motor unit 110 may be electrically driven, and may include encoders.

The motor unit 110 may include a first motor 111, a second motor 112, a third motor 113, a fourth motor 114, and a fifth motor 115 that correspond to the first direction D1, the second direction D2, the third direction D3, the fourth direction D4, and the fifth direction D5, respectively.

The first to fifth motors 111 to 115 may be arranged at appropriate locations in consideration of convenience of design. For example, the first motor 111 that is used to move the second guide rail 42 in the first direction D1 may be disposed around the first guide rail 41, the second motor 112 that is used to move the carriage 45 in the second direction D2 may be disposed around the second guide rail 42, and the third motor 113 that is used to increase or decrease the length of the post frame 50 in the third direction D3 may be disposed in the carriage 45. Also, the fourth motor 114 that is used to rotate the X-ray source 70 in the fourth direction D4 may be disposed around the first revolute joint 61, and the fifth motor 115 that is used to rotate the X-ray source 70 in the fifth direction D5 may be disposed around the second revolute joint 62.

The motor unit 110 may connect to a power transfer (not shown) in order to linearly move or rotate the X-ray source 70 in the first to fifth directions D1 to D5. The power transfer may be a belt and a pulley, a chain and a sprocket, or a shaft, for example.

In one side of the X-ray source 70, the operating unit 80 may be disposed to provide a user interface. The user is a person who diagnoses an object using the X-ray imaging apparatus 1, and may be a medical staff including a doctor, a radiological technologist, and a nurse. However, the user is not limited to the above-mentioned persons, and may be anyone using the X-ray imaging apparatus 1. The operating unit 80 may be connected to the X-ray source 70 by connectors 126, 127, and 128. The operating unit may receive network and power connections through connector 75.

The operating unit 80 may include, as illustrated in FIG. 3, a first display unit 81 and a plurality of buttons 84 to allow a user to input various kinds of information for radiography or to manipulate individual units. The first display unit 81 may be implemented as a Cathode Ray Tube (CRT), a Liquid Crystal Display (LCD), or a Light Emitting Diode (LED) display, for example. However, the first display unit 81 is not limited to the above-mentioned display devices.

The buttons 84 may include a fourth directional rotation selection button 85 and a fifth directional rotation selection button 86 to rotate the X-ray source 70 in the fourth direction D4 and in the fifth direction D5. That is, when a user wants to rotate the X-ray source 70 in the fourth direction D4, the user may rotate the X-ray source 70 in the fourth direction D4 after pressing the fourth directional rotation selection button 85 or while pressing the fourth directional rotation selection button 85. When the user wants to rotate the X-ray source 70 in the fifth direction D5, the user may rotate the X-ray source 70 in the fifth direction D5 after pressing the fifth directional rotation selection button 86 or while pressing the fifth directional rotation selection button 86. The locations of the fourth and fifth directional rotation selection buttons 85 and 86 shown in FIG. 3 are exemplary, and the fourth and fifth directional rotation selection buttons 85 and 86 may be arranged at different locations.

Also, the operating unit 80 may include a handle 82 that the user can grip. The user may grip the handle 82 of the operating unit 80 to apply power or torque, thereby moving the X-ray source 70. This is defined as a manual move mode, and an automatic move mode will be defined when a motor controller 340 (see FIG. 4) is described. In FIG. 3, the handle 82 is provided in the lower part of the operating unit 80, however, the handle 82 may be provided at another location.

The X-ray detector 100 may detect X-rays transmitted through the object. In the front side of the X-ray detector 100, an incident surface 130 onto which X-rays are incident may be provided, and a sensing panel 120 (see FIG. 6) may be installed in the X-ray detector 100. In the sensing panel 120, a plurality of pixels 150 (see FIG. 7) that respond to X-rays may be arranged in a matrix form, which will be described in more detail with reference to FIG. 6, later. In the upper center part of the X-ray detector 100, a handle 131 may be provided so that the user can move or carry the X-ray detector 100.

The X-ray detector 100 may operate in different radiography modes according to its location upon radiography. More specifically, the X-ray detector 100 may operate in a table mode in which the X-ray detector 100 is installed in the radiography table 10, in a stand mode in the X-ray detector 100 is installed in the radiography stand 20, or in a portable mode in which the X-ray detector 100 is placed at an arbitrary location according to an object's location or a part to be scanned without being installed in either the radiography table 10 or the radiography stand 20. Particularly, accommodating slots 15 and 25 into which the X-ray detector 100 can be inserted may be formed in the radiography table 10 and in the radiography stand 20. The accommodating slot 15 formed in the radiography table 10 is defined as a first accommodating slot 15, and the accommodating slot 25 formed in the radiography stand 20 is defined as a second accommodating slot 25. The second accommodating slot 25 is movable in the length direction of a support bar 22, and rotatable in the rotation direction of an axis perpendicular to the length direction of the support bar 22, as illustrated in FIG. 1. The length direction of the support bar 22 is defined as a sixth direction D6, and the rotation direction of the axis perpendicular to the sixth direction D6 is defined as a seventh direction D7. A method of installing the X-ray detector 100 will be described in detail, later.

The workstation 170 may include an input unit 171 and a second display unit 172 to provide a user interface, like the operating unit 80. Accordingly, the user can input various kinds of information for radiography or manipulate individual units through the workstation 170. Also, the user may input various commands (e.g., a command for selecting a radiography location, a start command for radiography, etc.) related to operations of the X-ray imaging apparatus 1 through the workstation 170. In addition, the user may check images acquired during radiography through the workstation 170.

The input unit 171 may include at least one of a switch, a keyboard, a trackball, a mouse, and a touch screen, for example. If the input unit 171 is implemented as a Graphic User Interface (GUI) such as a touch screen, in other words, if the input unit 171 is implemented in software, the input unit 171 may be displayed through the second display unit 172. The second display unit 172 may be, like the first display unit 81, implemented as a CRT, a LCD, or a LED display, for example.

The workstation 170 may include various processors, such as a Central Processing Unit (CPU) or a Graphic Processing Unit (GPU), and a Printed Circuit Board (PCB), and may further include various kinds of storage units as necessary. Accordingly, the workstation 170 may include main components (e.g., the controller 300 (see FIG. 4)) of the X-ray imaging apparatus 1 to make determinations for operations of the X-ray imaging apparatus 1 or to generate various control signals.

The workstation 170 may be placed in an independent space B from which X-rays can be blocked, and may be connected to the X-ray source 70 and the X-ray detector 100 through wired/wireless communication.

Figure 4:
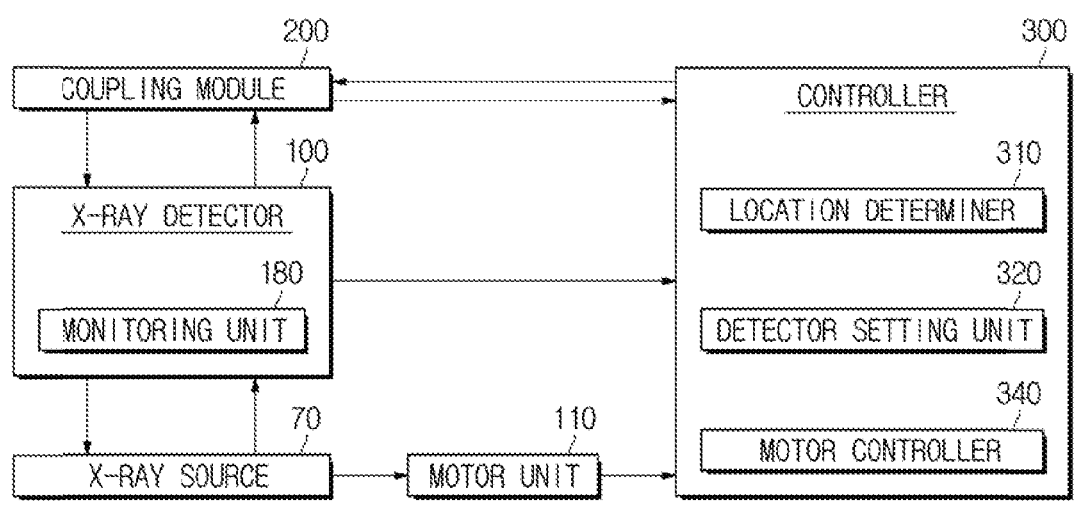
FIG. 4 is a control block diagram of an X-ray imaging apparatus according to an embodiment of the present disclosure.

FIG. 4 is a control block diagram of the X-ray imaging apparatus 1 according to an embodiment of the present disclosure.

Referring to FIG. 4, the X-ray imaging apparatus 1 may include the X-ray source 70, the X-ray detector 100, a coupling module 200, a controller 300, and the motor unit 110, and the controller 300 may determine a location of the X-ray detector 100, and move the X-ray source 70 to correspond to the location of the X-ray detector 100.

The coupling module 200 may be connected to the X-ray detector 100. Also, the coupling module 200 may include an electric device to generate an electrical signal or a change in electrical signal according to coupling with or decoupling from the X-ray detector 100. The X-ray detector 100 may include a monitoring unit 180 to monitor the electrical signal or the change in the electric signal and to convert the results of the monitoring into a digital value.

Accordingly, if the X-ray detector 100 is connected to the coupling module 200, an electrical signal may be generated by the electric device of the coupling module 200, and the monitoring unit 180 of the X-ray detector 100 may read the electrical signal and transmit it to the controller 300. The controller 300 may determine a location of the X-ray detector 100 based on the electrical signal.

Also, a plurality of coupling modules 200 may be provided to correspond to the respective modes of the X-ray detector 100. More specifically, coupling modules 200 may be respectively provided at a location corresponding to the stand mode and at a location corresponding to the table mode, and also, another coupling module 200 may be provided at a location corresponding to the portable mode. Details about the locations and structures of the coupling modules 200 will be described later.

Figure 5:
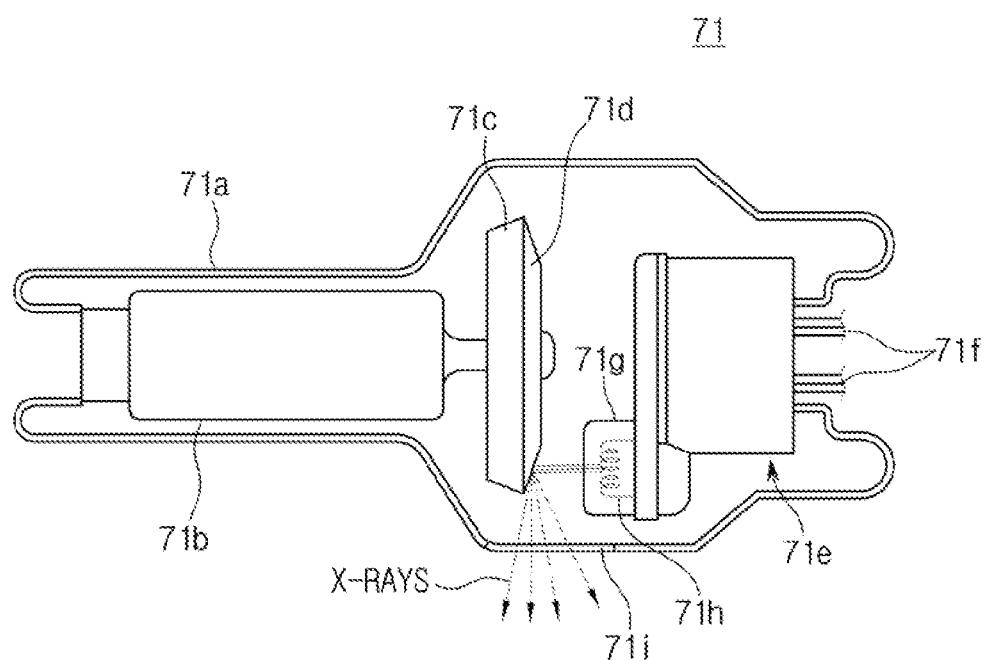
FIG. 5 illustrates an example of an internal structure of an X-ray tube.

The X-ray source 70 may generate X-rays, and irradiate the generated X-rays to an object. In order to generate X-rays, the X-ray source 70 may include an X-ray tube 71 as illustrated in FIG. 5. FIG. 5 illustrates an example of an internal structure of the X-ray tube 71.

The X-ray tube 71 may be embodied as a two-electrode vacuum tube including an anode 71c and a cathode 71e. The body of the two-electrode vacuum tube may be a glass tube 71a made of silica (hard) glass or the like.

The cathode 71e may include a filament 71h and a focusing electrode 71g for focusing electrons, and the focusing electrode 71g is also called a focusing cup. The inside of the glass tube 71a may be evacuated to a high vacuum state of approximately 10 mmHg, and the filament 71h of the cathode 71e may be heated to a high temperature, thereby generating thermoelectrons. The filament 71h may be a tungsten filament, for example, and the filament 71h may be heated by applying a current to electrical leads 71f connected to the filament 71h. However, instead of the filament 71h, a carbon nano-tube capable of being driven with high-speed pulses may be used as the cathode 71e.

The anode 71c may be made of copper, for example, and a target material 71d is applied on the surface of the anode 71c facing the cathode 71e, wherein the target material 71d may be a high-resistance material, e.g., Cr, Fe, Co, Ni, W, or Mo. The higher the melting point of the target material 71d, the smaller the focal spot size.

When a high voltage is applied between the cathode 71e and the anode 71c, thermoelectrons may be accelerated and collide with the target material 71d of the anode 71e, thereby generating X-rays. The X-rays may be irradiated to the outside through a window 71i. The window 111i may be a Beryllium (Be) thin film.

The target material 71d may be rotated by a rotor 71b. When the target material 71d rotates, the heat accumulation rate may increase 10 times per unit area and the focal spot size may be reduced, compared to when the target material 71d is fixed.

The voltage that is applied between the cathode 71e and the anode 71c of the X-ray tube 71 is called a tube voltage. The magnitude of a tube voltage may be expressed as a crest value (kVp). When the tube voltage increases, a velocity of thermoelectrons may increase accordingly. Then, energy (energy of photons) of X-rays that are generated when the thermoelectrons collide with the target material 71d may also increase. A current flowing through the X-ray tube 71 is called a tube current, and can be expressed as an average value (mA). When a tube current increases, a dose of X-rays (that is, the number of X-ray photons) may increase. In summary, an energy level of X-rays can be controlled by adjusting a tube voltage. Also, a dose of X-rays can be controlled by adjusting a tube current and an X-ray exposure time.

The X-ray detector 100 may detect X-rays irradiated by the X-ray source 70 and then transmitted through an object. The X-rays may be detected by the sensing panel 120 installed in the X-ray detector 100. The sensing panel 120 may convert the detected X-rays into electrical signals, and acquire an image about the inside of the object.

The sensing panel 120 can be classified according to its material configuration, a method of converting detected X-rays into electrical signals, and a method of acquiring image signals.

The sensing panel 120 is classified into a mono type device or a hybrid type device according to its material configuration.

If the sensing panel 120 is a mono type device, a part of detecting X-rays and generating electrical signals, and a part of reading and processing the electrical signals may be semiconductors made of the same material, or may be manufactured by one process. In this case, the sensing panel 120 may be a Charge Coupled Device (CCD) or a Complementary Metal Oxide Semiconductor (CMOS) which is a light receiving device.

If the sensing panel 120 is a hybrid type device, a part of detecting X-rays and generating electrical signals, and a part of reading and processing the electrical signals may be made of different materials, or may be manufactured by different processes. For example, there are cases of detecting X-rays using a light receiving device, such as a photodiode, a CCD, or CdZnTe, and reading and processing electrical signals using a CMOS Read Out Integrated Circuit (CMOS ROIC), of detecting X-rays using a strip detector, and reading and processing electrical signals using a CMOS ROIC, and of using an a-Si or a-Se flat panel system.

The X-ray detector 120 may use a direct conversion mode and an indirect conversion mode according to a method of converting X-rays into electrical signals.

In the direct conversion mode, if X-rays are irradiated, electron-hole pairs are temporarily generated in a light receiving device, electrons move to an anode, and holes move to a cathode by an electric field applied to both terminals of the light receiving device. The sensing panel 120 converts the movements of the electrons and holes into electrical signals. The light receiving device may be made of a-Se, CdZnTe, Hgl2, or Pbl2, for example.

In the indirect conversion mode, if X-rays irradiated from the X-ray source 70 react with a scintillator to emit photons having a wavelength of a visible light region, the light receiving device detects the photons, and converts the photons into electrical signals. The light receiving device may be made of a-Si, and the scintillator may be a GADOX scintillator of a thin film type, or a CSI (TI) of a micro pillar type or a needle type.

The sensing panel 120 may use a Charge Integration Mode (CIM) of storing charges for a predetermined time period and then acquiring a signal from the stored charges, or a Photon Counting Mode (PCM) of counting the number of photons having energy higher than threshold energy whenever a signal is generated by single X-ray photons, according to a method of acquiring image signals.

The material configuration of the sensing panel 120 and the signal conversion method of the sensing panel 120 are not limited, however, for convenience of description, in an embodiment of the present disclosure which will be described below, the sensing panel 120 uses the direct conversion mode of acquiring electrical signals directly from X-rays and the PCM, and the sensing panel 120 is a hybrid type in which a sensor chip for detecting X-rays is integrated with a read circuit chip.

Figure 6:
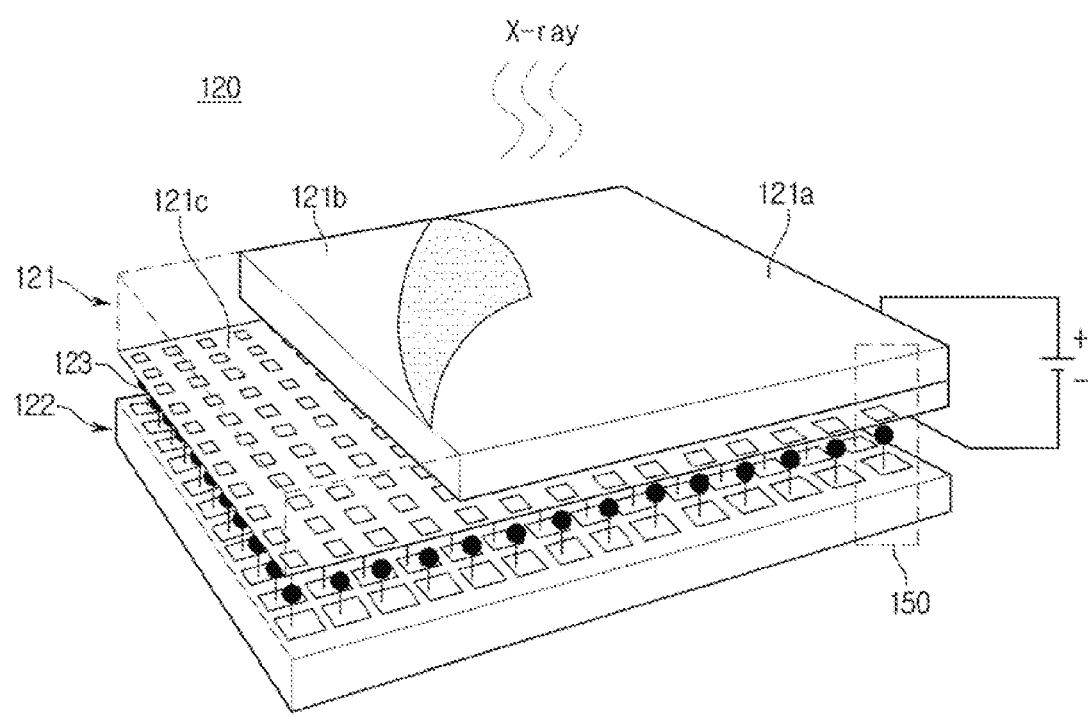
FIG. 6 schematically illustrates a structure of a sensing panel.

The sensing panel 120 may have a 2-dimensional (2D) pixel array structure including a plurality of pixels 150, as illustrated in FIG. 6. FIG. 6 schematically illustrates a structure of the sensing panel 120.

Referring to FIG. 6, the sensing panel 120 may include a light receiving device 121 to detect X-rays and convert the X-rays into electrical signals, and a read circuit 122 to read out the electrical signals.

The light receiving device 121 may be made of a single crystal semiconductor material in order to ensure high resolution, high response speed, and a high dynamic area even under conditions of low energy and a small dose of X-rays. The single crystal semiconductor material may be Ge, CdTe, CdZnTe, or GaAs.

The light receiving device 121 may be in the form of a PIN photodiode. The PIN photodiode may be fabricated by bonding a p-type semiconductor substrate 121c in the form of a 2D pixel array on the lower surface of a n-type semiconductor substrate 121b having high resistance.

The read circuit 122, which is fabricated according to a Complementary Metal Oxide Semiconductor (CMOS) process, may form a 2D array structure, and may be coupled with the p-type substrate 121c of the light receiving device 121 in units of pixels. The CMOS read circuit 122 and the light receiving device 121 may be coupled by a Flip-Chip Bonding (FCB) method. More specifically, the CMOS read circuit 122 and the light receiving device 121 may be coupled by forming bumps 123 with PbSn, In, or the like, reflowing, applying heat, and then compressing.

Figure 7:
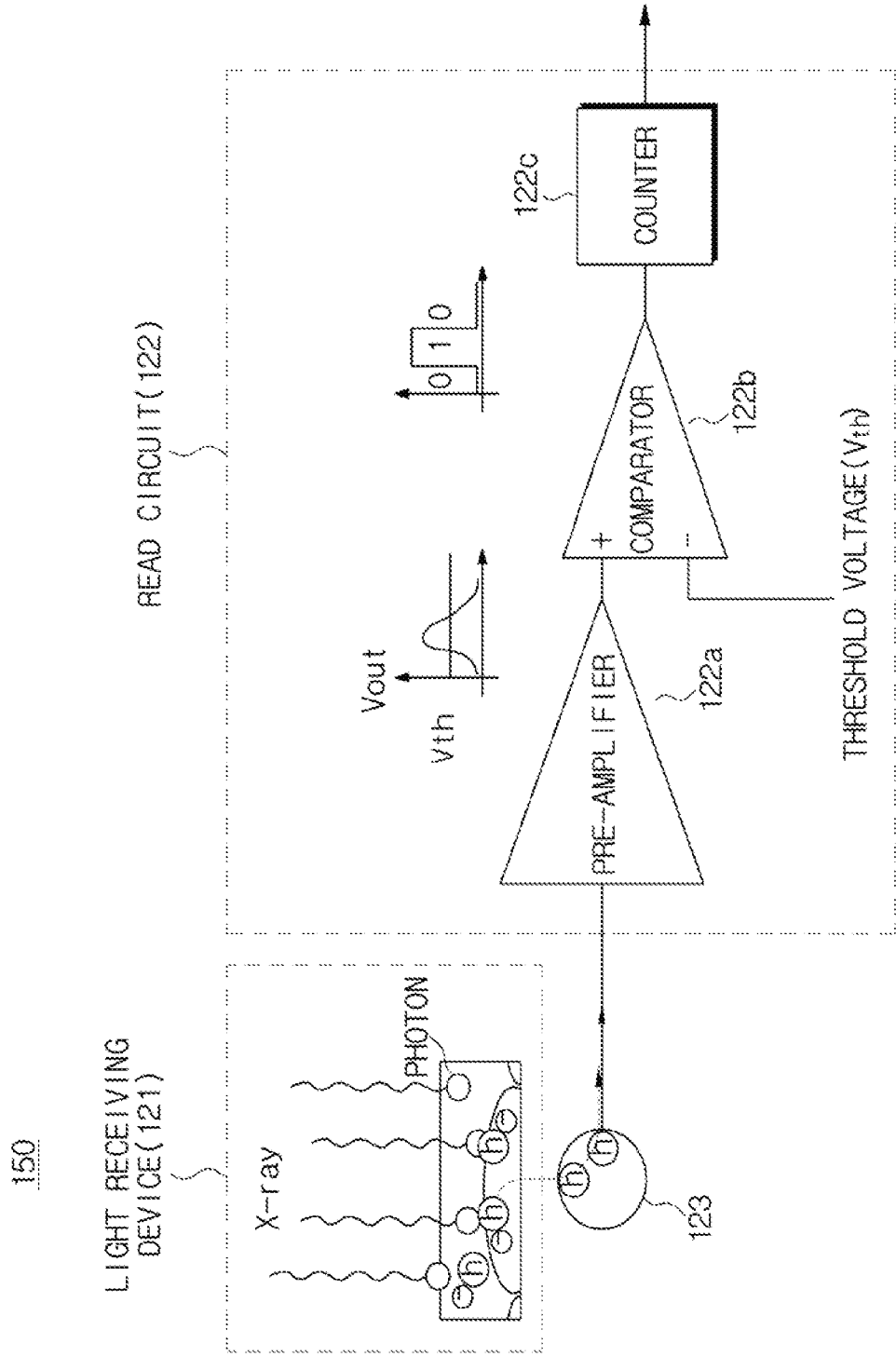
FIG. 7 is a circuit diagram schematically illustrating a pixel area of the sensing panel illustrated in FIG. 6.

FIG. 7 is a circuit diagram schematically illustrating a pixel area of the sensing panel 120 illustrated in FIG. 6.

Referring to FIG. 7, if photons of X-rays are incident to the light receiving device 121, electrons existing in a valance band may receive the energy of the photons to be excited to a conduction band over an energy gap of a band gap. Thereby, electron-hole pairs may be generated in a depletion region where neither electrons nor holes exist.

If a reverse bias is applied after metal electrodes are respectively formed on the p-type layer and the n-type substrate of the light receiving device 121, electrons in the electron-hole pairs generated in the depletion region may move to the n-type region, and holes in the electron-hole pairs may move to the p-type region. The holes moved to the p-type region may be input to the read circuit 122 through the bumps 123.

Charges input to the read circuit 122 may be transferred to a pre-amplifier 122a, and the pre-amplifier 122a may output a voltage signal corresponding to the charges.

The voltage signal output from the pre-amplifier 122a may be transferred to a comparator 122b. The comparator 122b may compare the voltage signal to a predetermined threshold voltage that can be controlled by an external device, to output a pulse signal of "1" or "0" as the result of the comparison. More specifically, if a voltage of the voltage signal is greater than the predetermined threshold voltage, the comparator 122b may output a signal of "1", and if the voltage of the voltage signal is smaller than the predetermined threshold voltage, the comparator 122b may output a signal of "0". The counter 122c may count the number of times a signal of "1" has been generated, and output the count value as digital data.

Figure 10:
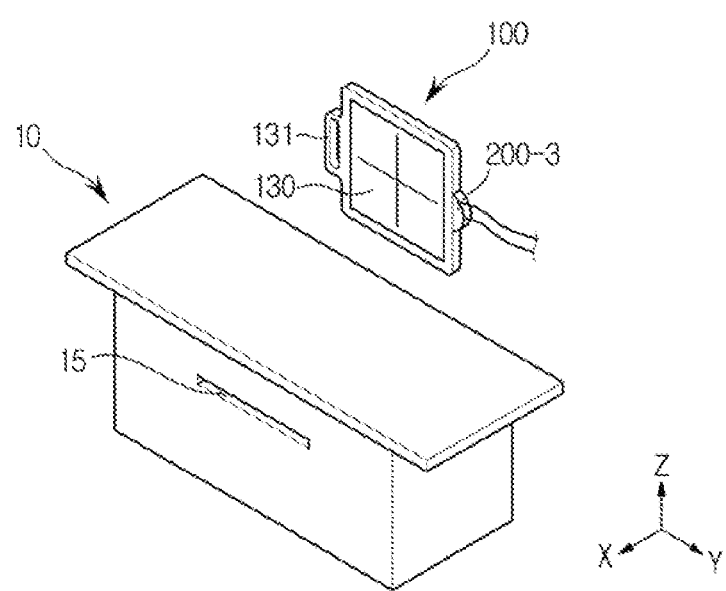
FIG. 10 is a view for describing a case in which an X-ray detector is used in a portable mode.

As described above, the X-ray detector 100 may operate in the table mode, in the stand mode, or in the portable mode in order to detect X-rays. The locations of the X-ray detector 100 in the individual radiography modes will be described with reference to FIGS. 8 to 10, below. FIG. 8 is a view for describing a method in which the X-ray detector 100 is installed in the radiography table 10, FIG. 9 is a view for describing a method in which the X-ray detector 100 is installed in the radiography stand 20, and FIG. 10 is a view for describing a case in which the X-ray detector 100 is used in the portable mode.

As described above, a plurality of coupling modules 200 may be provided to correspond to the respective radiography modes. Referring to FIGS. 8 to 10, the coupling module 200 may include a table coupling module 200-1 corresponding to the table mode, a stand coupling module 200-2 corresponding to the stand mode, and a portable coupling module 200-3 corresponding to the portable mode. However, the locations and numbers of the coupling modules 200 are only exemplary. That is, only the table coupling module 200-1 and the stand coupling module 200-2 may be provided, or four coupling modules or more may be provided. In the current embodiment, it is assumed that the coupling modules 200 includes the table coupling module 200-1, the stand coupling module 200-2, and the portable coupling module 200-3.

Referring to FIG. 8, the table coupling module 200-1 may be installed in the first accommodation slot 15. In order to perform radiography on an object that is lying on the radiography table 10, the X-ray detector 100 may be installed in the radiography table 10. More specifically, the X-ray detector 100 may be inserted into the first accommodating slot 15 formed in the radiography table 10. When the X-ray detector 100 is inserted into the first accommodating slot 15, the X-ray detector 100 is inserted in a state of being parallel to a bottom plane, that is, a plane formed by x- and y-axes, as illustrated in FIG. 8(a). After the X-ray detector 100 is inserted into the first accommodating slot 15, the X-ray detector 100 may be maintained in the state of being parallel to the bottom plane or the plane formed by x- and y-axes, as illustrated in FIG. 8(b). Meanwhile, the X-ray detector 100 inserted into the first accommodating slot 15 may be connected to the table coupling module 200-1. As such, a state in which the X-ray detector 100 has been inserted into the first accommodating slot 15 and coupled with the table coupling module 200-1 is the table mode.

Referring to FIG. 9, the stand coupling module 200-2 may be installed in the second accommodation slot 25. In order to perform radiography on an object that stands in front of the radiography stand 20, the X-ray detector 100 may be installed in the radiography stand 20. More specifically, the X-ray detector 100 may be inserted into the second accommodating slot 25 formed in the radiography stand 20. Because the second accommodating slot 25 is rotatable in the seventh direction D7, the X-ray detector 100 may be inserted into the second accommodating slot 25 in a state of being perpendicular to a bottom plane or parallel to a plane formed by x- and z-axes, as illustrated in the left side of FIG. 9(*a*), or the X-ray detector 100 may be inserted into the second accommodating slot 25 in a state of being parallel to the bottom plane or parallel to a plane formed by x- and y-axes, as illustrated in the right side of FIG. 9(*a*). After the X-ray detector 100 is inserted into the second accommodating slot 25, the second accommodating slot 25 may rotate so that the X-ray detector 100 is maintained in a state of being perpendicular to the bottom plane, that is, parallel to the plane formed by x- and z-axes, as illustrated in FIG. 9(*b*). Meanwhile, the X-ray detector 100 inserted into the second accommodating slot 25 may be connected to the stand coupling module 200-2. As such, a state in which the X-ray detector 100 has been inserted into the second accommodating slot 25 and coupled with the stand coupling module 200-2 is the stand mode.

In order to perform radiography on a moving object as well as an object that is lying or stands, the X-ray detector 100 may be in a portable state without being inserted into either the radiography table 10 or the radiography stand 20. This state is the portable mode. As shown in FIG. 10, in the portable mode, the X-ray detector 100 may be coupled with the portable coupling module 200-3, and the portable coupling module 200-3 may be placed at an arbitrary location at which radiography can be easily performed in the portable mode. For example, the portable coupling module 200-3 may be, as shown in FIG. 10, placed in the backside of the top plate of the radiography table 10.

Figure 13:
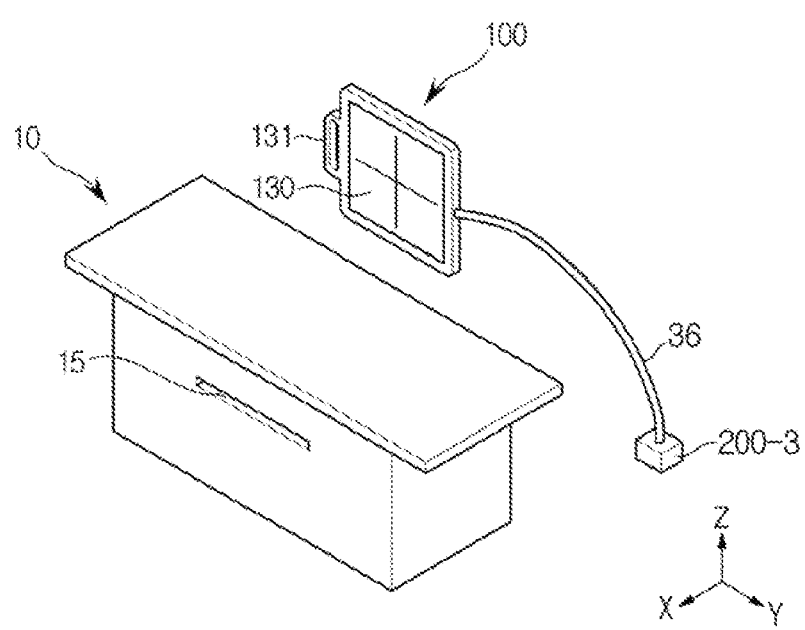

FIGS. 11 to 13 show exemplary locations of the table coupling module 200-1, the stand coupling module 200-2, and the portable coupling module 200-3.

Referring to FIG. 11, the table coupling module 200-1 may be located outside the first accommodation slot 15, and coupled with the X-ray detector 100 inserted in the first accommodation slot 15 through a cable 16. In order to be coupled with the X-ray detector 100, the table coupling module 200-1 may be located adjacent to the radiography table 10.

Referring to FIG. 12, the stand coupling module 200-2 may be located outside the second accommodation slot 25, and coupled with the X-ray detector 100 inserted in the second accommodation slot 25 through a cable 26. In order to be coupled with the X-ray detector 100, the stand coupling module 200-2 may be located adjacent to the radiography stand 20.

Referring to FIG. 13, the portable coupling module 200-3 may be coupled with the X-ray detector 100 in the portable mode through a cable 36.

Meanwhile, if the X-ray detector 100 receives a supply voltage in a wired fashion and is connected to a workstation in a wired fashion, each coupling module 200 may function to connect the X-ray detector 100 to an external power supply and a network hub. Alternatively, each coupling module 200 may be implemented as a board on which electric devices are mounted, separately from a configuration of connecting the X-ray detector 100 to an external power supply and a network hub. Hereinafter, a configuration of the coupling module 200 will be described in detail.

First, a case in which the coupling module 300 includes a configuration of connecting the X-ray detector 100 to an external power supply and a network hub will be described. In this case, the coupling module 200 may be called a power box, however, the coupling module 200 has to be defined by its configuration and operation, not by its name.

Figure 14:
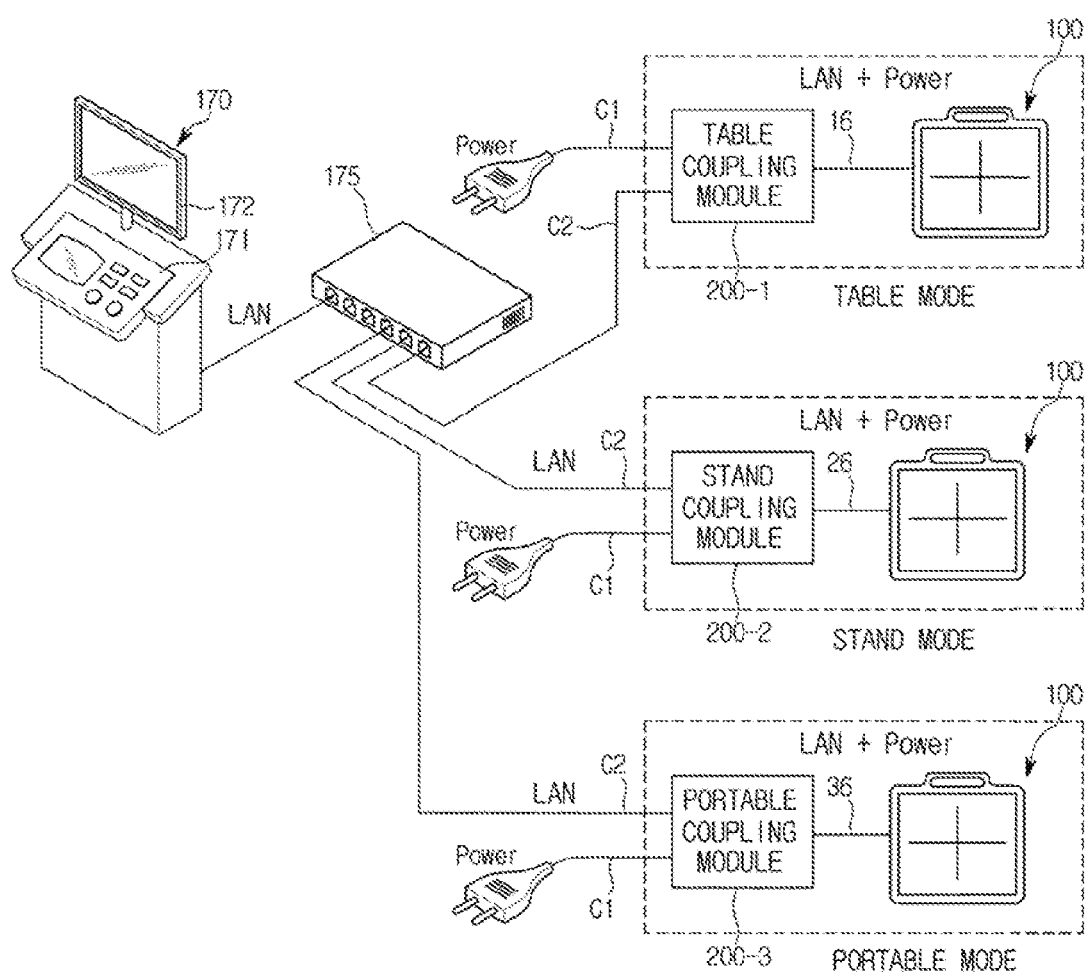
FIG. 14 shows a configuration in which an X-ray detector is connected to other external devices through coupling modules.

FIG. 14 shows a configuration in which the X-ray detector 100 is connected to other external devices through the coupling modules 200.

As shown in FIG. 14, the X-ray detector 100 that is in the table mode, in the stand mode, or in the portable mode may be connected to a power supply unit and a workstation 170 through the corresponding coupling module 200. The coupling modules 200 may include the table coupling module 200-1 included in the radiography table 10, the stand coupling module 200-2 included in the radiography stand 20, and the portable coupling module 200-3. The coupling modules 200 may supply a supply voltage to the X-ray detector 100 installed in the radiography table 10 to be in the table mode, installed in the radiography stand 20 to be in the stand mode, or coupled with the portable coupling module 200-3 to be in the portable mode, and the coupling modules 200 may connect the X-ray detector 100 to the workstation 170. The coupling modules 200 may connect to the X-ray detector 100 through single integrated cables 16, 26, and 36. As shown in FIG. 14, the each coupling module 200 may connect to the power supply unit through a power cable C1, and to the network hub 175 through a communication cable C2. However, the coupling modules 200 may connect to the X-ray detector 100 through the single integrated cables 16, 26, and 36, and the integrated cables 16, 26, and 36 may supply a supply voltage and function as communication lines.

More specifically, if the X-ray detector 100 is installed in the radiography table 10, the X-ray detector 100 may be coupled with the table coupling module 200-1. The table coupling module 200-1 may connect to the power supply unit through the power cable C1, and supply a supply voltage transferred from the power supply unit to the X-ray detector 100 coupled with the table coupling module 200-1 through the integrated cable 16. Also, the table coupling module 200-1 may connect to the workstation 170 through the network hub 175. Accordingly, the table coupling module 200-1 may output various command signals received from the workstation 170 to the X-ray detector 100 coupled with the table coupling module 200-1, and output various data received from the X-ray detector 100 coupled with the table coupling module 200-1 to the workstation 170.

If the X-ray detector 100 is installed in the radiography stand 20, the X-ray detector 100 may be coupled with the stand coupling module 200-2. The stand coupling module 200-2 may connect to the power supply unit through the power cable C1, and connect to the workstation 170 through the network hub 175 connected via the communication cable C2. Accordingly, the stand coupling module 200-2 may supply a supply voltage transferred from the power supply unit to the X-ray detector 100 coupled with the stand coupling module 200-2 through the integrated cable 26. Also, the stand coupling module 200-2 may output various command signals received from the workstation 170 to the X-ray detector 100 coupled with the stand coupling module 200-2 through the integrated cable 26, and output various data received from the X-ray detector 100 coupled with the stand coupling module 200-2 to the workstation 170.

Likewise, if the X-ray detector 100 is in the portable mode, the X-ray detector 100 may be coupled with the portable coupling module 200-3 through the integrated cable 36. The portable coupling module 200-3 may connect to the power supply unit through the integrated cable 36, and supply a supply voltage transferred from the power supply unit to the X-ray detector 100 coupled with the portable coupling module 200-3. Also, the portable coupling module 200-3 may connect to the workstation 170 through the network hub 175 and the communication cable C2 to output various command signals received from the workstation 170 to the X-ray detector 100 coupled with the portable coupling module 200-3 and to output various data received from the X-ray detector 100 coupled with the portable coupling module 200-3 to the workstation 170.

The X-ray detector 100 may be coupled with the individual coupling modules 200-1, 200-2, and 200-3 through communication lines of Local Area Network (LAN). Also, the cables C2 connecting the workstation 170 to the individual coupling modules 200-1, 200-2, and 200-3, more specifically, a cable connecting the workstation 170 to the network hub 175 and the communication cables C2 connecting the network hub 175 to the individual coupling modules 200-1, 200-2, and 200-3 may include the communication lines of LAN, as illustrated in FIG. 14.

Also, each coupling module 200 may further include an electric device to generate an electrical signal and a change in electrical signal according to coupling with the X-ray detector 100. Details about the electric device will be described later.

Figure 15:
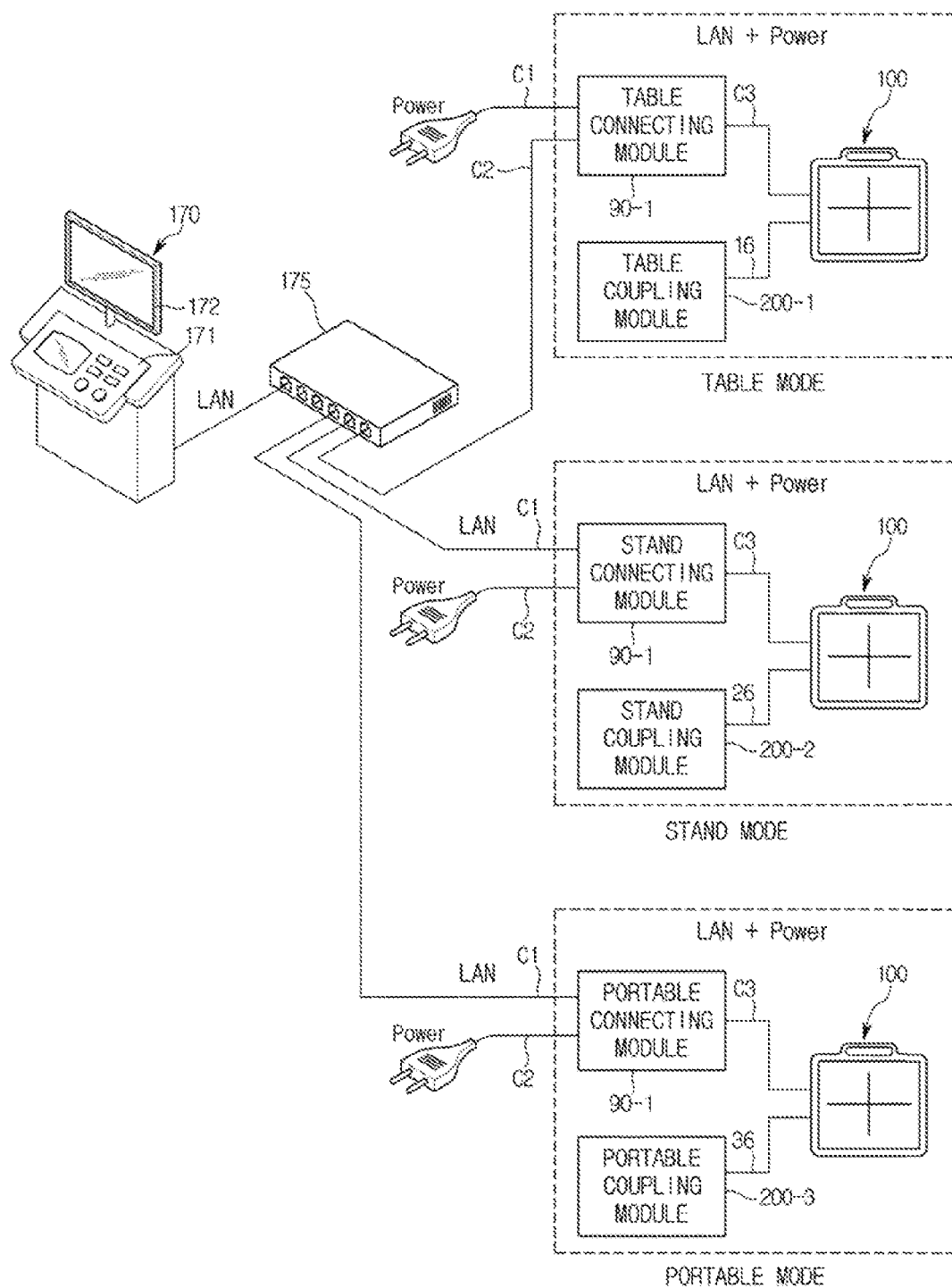
FIG. 15 shows another example of connection relationships between coupling modules and an X-ray detector.

According to another example, each coupling module 200 may be provided separately from a component to supply a supply voltage and function as a communication line. FIG. 15 shows another example of connection relationships between coupling modules and the X-ray detector 100.

Referring to FIG. 15, in order to receive a supply voltage and perform communications, the X-ray detector 100 that is in the table mode may connect to a table connecting module 90-1, the X-ray detector 100 that is in the stand mode may connect to a stand connecting module 90-2, and the X-ray detector 100 that is in the portable mode may connect to a portable connecting module 90-3. The connecting modules 90-1, 90-2, and 90-3 may function to connect the X-ray detector 100 to the power supply unit and the network hub 175, as described above with reference to FIG. 14.

The coupling modules 200 may be separated from the connecting modules 90-1, 90-2, and 90-3, respectively. For example, each of the coupling modules 200-1, 200-2, and 200-3 may be configured with a sub board and an electric device mounted on the sub board. In this case, the X-ray detector 100 may connect to the respective connecting modules 90-1, 90-2, and 90-3 through integrated cables C3, and connect to the coupling modules 200-1, 200-2, and 200-3 through separate cables 16, 26, and 36, respectively.

Referring again to FIG. 4, the controller 300 may include a location determiner 310, a detector setting unit 320, and a motor controller 340.

The location determiner 310 may determine a location at which the X-ray detector 100 has been installed. In order to help a determination by the location determiner 310, the X-ray detector 100 may include a monitoring unit 180 (for example, an Analog-Digital Converter (ADC) port or a General Purpose Input/Output (GPIO) port) to monitor a voltage, and the coupling module 200 may include an electric device to generate an electrical signal according to coupling with the X-ray detector 100. In order to identify the coupling module 200 according to the generated electrical signal, the electric device may be an IDentification (ID) electric device having a unique characteristic value. For example, the ID electric device may be a unique ID resistor. A method in which the location determiner 310 determines an installation location of the X-ray detector 100 using the monitoring unit 180 and the ID resistor will be described in detail with reference to FIGS. 16 and 17, below.

Figure 16:
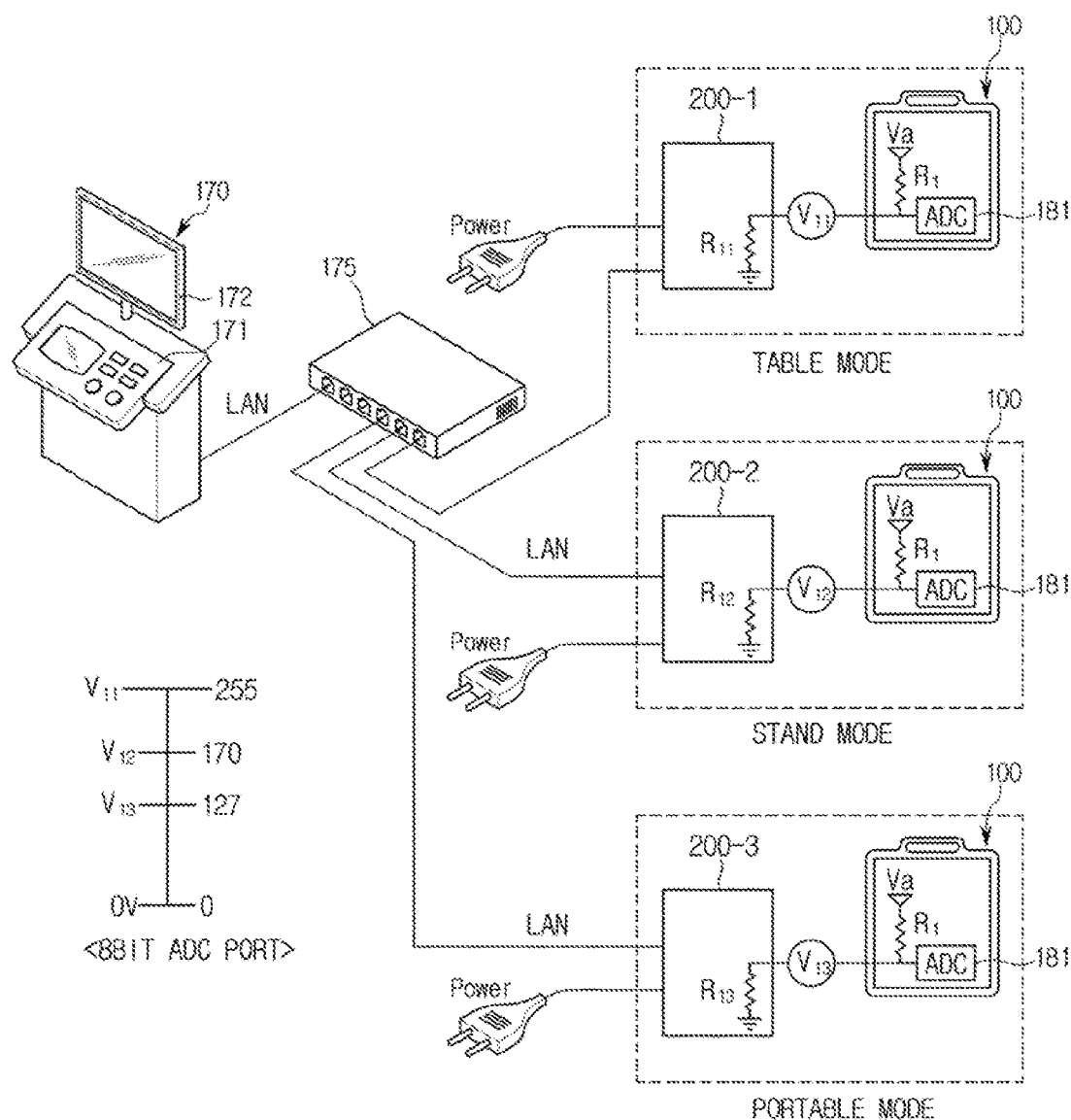
FIGS. 16 and 17 are views for describing an example of a method of determining an installation location of an X-ray detector based on the control block diagram of FIG. 4.
Figure 17:
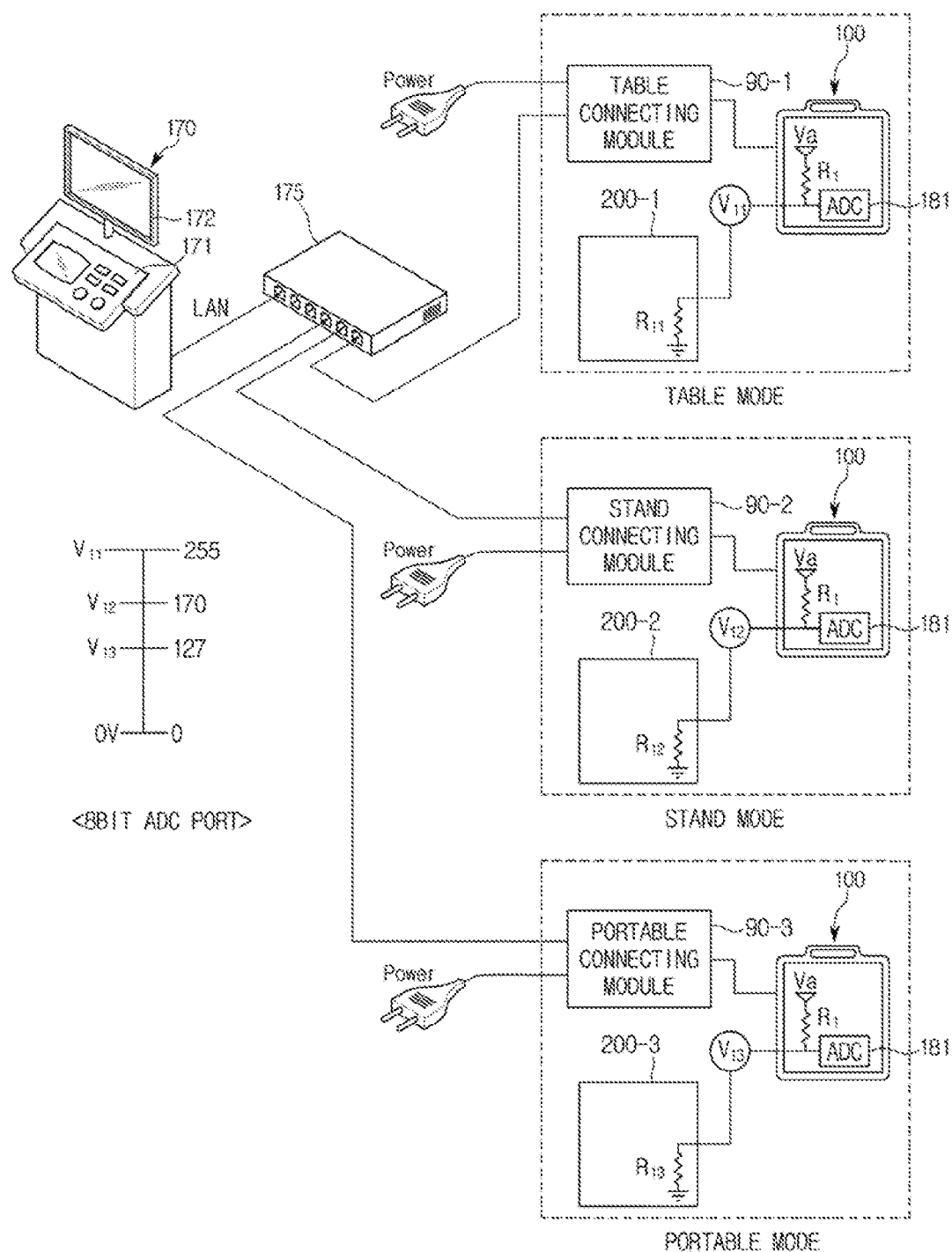
Figure 18:
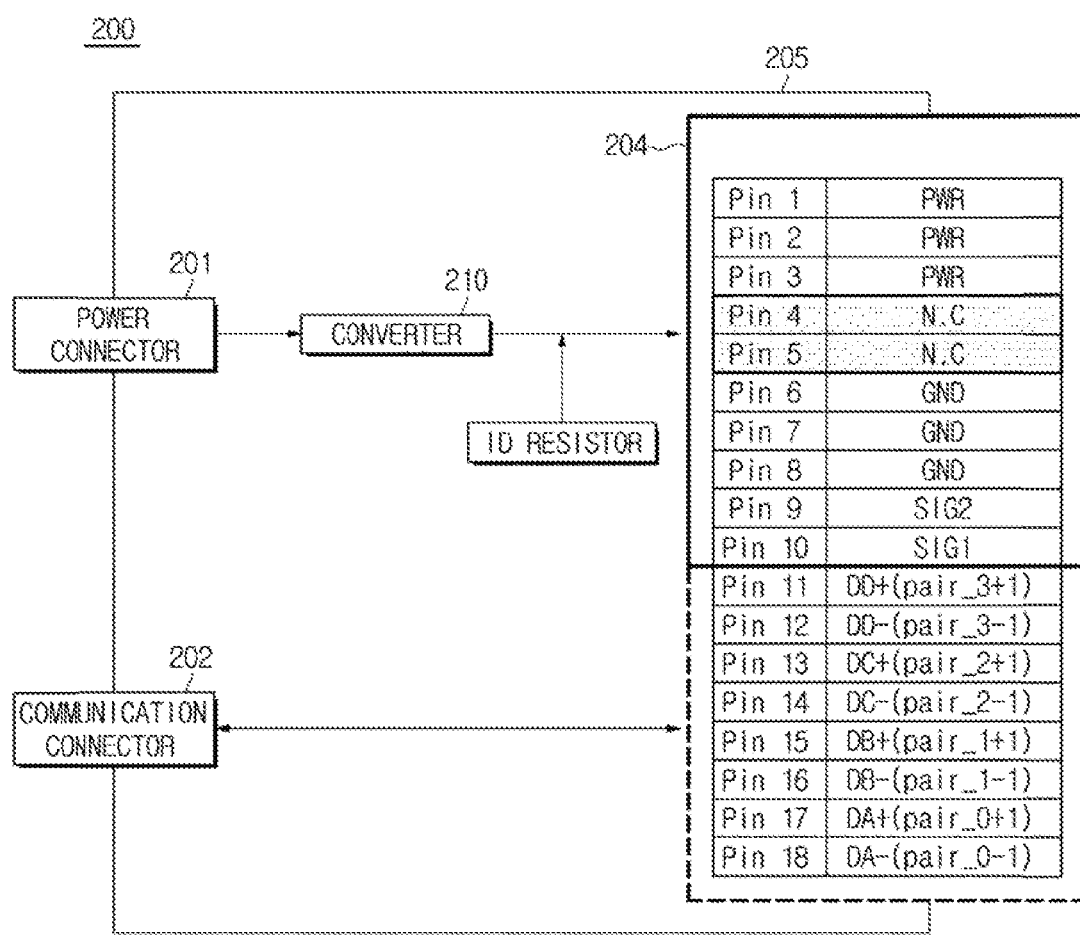
FIG. 18 shows an internal configuration of a coupling module.

FIGS. 16 and 17 are views for describing an example of a method of determining an installation location of the X-ray detector 100 based on the control block diagram of FIG. 4, and FIG. 18 shows an internal configuration of the coupling module 200. FIGS. 16 and 18 relate to a case in which each coupling module supplies a supply voltage while functioning as a communication line, and FIG. 17 relates to a case in which each coupling module is implemented as a separate module without supplying a supply voltage or functioning as a communication line.

The X-ray detector 100 may include the monitoring unit 180 for monitoring a voltage and converting a level of the monitored voltage into a digital value. In FIG. 16, as an example of the monitoring unit 180, an ADC port 181 is shown. The ADC port 181 may be an Analog-Digital port. Also, the table coupling module 200-1 includes an ID resistor $R_{11}$, the stand coupling module 200-2 includes an ID resistor $R_{12}$, and the portable coupling module 200-3 includes an ID resistor $R_{13}$. The ID resistors $R_{11}$, $R_{12}$, and $R_{13}$ have different resistance values that are unique values for identifying the respective radiography modes.

Referring to FIG. 18, the coupling module 200 that supplies a supply voltage while functioning as a communication line may include a power connector 201 to which the power cable C1 is connected, and a communication connector 202 to which the communication cable C2 is connected. The power connector 201 and the communication connector 202 may be implemented as ports. A power supply unit to which the other end of the power cable C1 is connected may supply an AC voltage, and in this case, the coupling module 200 may further include a converter 210 to convert an AC voltage into a DC voltage so as to supply a DC voltage to the X-ray detector 100.

A detector connecting unit 204 that is connected to the X-ray detector 100 may include a plurality of fins, and an arrangement example of the fins is shown in FIG. 18. Referring to the example of FIG. 18, a part of the fins, for example, Pin 11 to Pin 18 may be used to connect to a communication line, Pin 1 to Pin 10 may be used to supply a supply voltage, and Pin 4 and Pin 5 corresponding to non-connected terminals among the pins used for supplying a supply voltage may be used to monitor an electrical signal generated by an ID resistor.

As shown in FIG. 18, if the coupling module 200 supplies a supply voltage while functioning as a communication line, the coupling module 200 can be easily configured by adding an ID resistor on a conventional board 205 for supplying a supply voltage and functioning as a communication line.

As described above, the coupling module 200 may supply a supply voltage and function as a communication line, while generating an electrical signal according to coupling with the X-ray detector 100, or the coupling module 200 may be implemented as a separate module from a connecting module of supplying a supply voltage and functioning as a communication line. However, in the current embodiment, for convenience of description, a case in which the coupling module 200 supplies a supply voltage while functioning as a communication line will be described as an example.

Referring again to FIGS. 16 and 17, a voltage Va is applied to the X-ray detector 100. The voltage Va may be applied through a voltage probe. Because the ID resistors included in the respective coupling modules 200-1, 200-2, and 200-3 have different resistance values, a voltage that is monitored by the ADC port 181 varies depending on which coupling module the X-ray detector 100 has been coupled with.

In detail, if the X-ray detector 100 is in the table mode, the ADC port 181 may monitor a voltage $V_{11}$ applied to an ID check line in correspondence to the ID resistor $R_{11}$ included in the table coupling module 200-1. If the X-ray detector 100 is in the stand mode, the ADC port 181 may monitor a voltage $V_{12}$ applied to an ID check line in correspondence to the ID resistor $R_{12}$ included in the stand coupling module 200-2. If the X-ray detector 100 is in the portable mode, the ADC port 181 may monitor a voltage $V_{13}$ applied to an ID check line in correspondence to the ID resistor $R_{13}$ included in the portable coupling module 200-3.

The ADC port 181 may convert the monitored voltage into a digital value corresponding to a level of the monitored voltage, and output the digital value to the location determiner 310. As described above, because a voltage that is monitored by the ADC port 181 varies depending on which coupling module the X-ray detector 100 has been coupled with, a value which the ADC port 181 outputs to the location determiner 310 also varies depending on which coupling module the X-ray detector 100 has been coupled with. In the current example, it is assumed that the ADC port 181 is an 8 bit ADC. That is, it is assumed that the ADC port 181 can output a value ranging from 0 to 255.

If the X-ray detector 100 has been installed in the radiography table 10 and monitored a voltage $V_{11}$, for example, a voltage of 5V, the ADC port 181 may output a digital value (e.g., 255) corresponding to 5V to the location determiner 310. If the X-ray detector 100 has been installed in the radiography stand 20 and monitored a voltage $V_{12}$, for example, a voltage of 3.2V, the ADC port 181 may output a digital value (e.g., 170) corresponding to 3.2V to the location determiner 310. If the X-ray detector 100 is in the portable mode and has monitored a voltage $V_{13}$, for example, a voltage of 2.5V, the ADC port 181 may output a digital value (e.g., 127) corresponding to 2.5V to the location determiner 310.

Because the voltage Va that is applied to the X-ray detector 100 is constant, and a resistance value of an ID resistor also does not change in a module, the ADC port 181 may output a constant digital value when the X-ray detector 100 has been installed in a module. If the X-ray detector 100 has been installed in the radiography table 10, the ADC port 181 outputs a value of 255, and if the X-ray detector 100 has been installed in the radiography stand 20, the ADC port 181 outputs a value of 170. Also, if the X-ray detector 100 is in the portable mode, the ADC port 181 outputs a value of 127.

Accordingly, the location determiner 310 may determine a location at which the X-ray detector 100 has been installed, based on a digital value output from the ADC port 181. If the ADC port 181 has output a value of 255, the location determiner 310 may determine that the X-ray detector 100 has been installed in the radiography table 10, and if the ADC port 181 has output a value of 170, the location determiner 310 may determine that the X-ray detector 100 has been installed in the radiography stand 20. Also, if the ADC port 181 has output a value of 127, the location determiner 310 may determine that the X-ray detector 100 is in the portable mode.

Meanwhile, in order for the respective coupling modules 200 to include different ID resistors, the respective coupling modules may include resistors having different ID resistance values. However, it is also possible to provide a single coupling module and to change a resistance value through a switch. This will be described with reference to FIG. 19, below.

Figure 19:
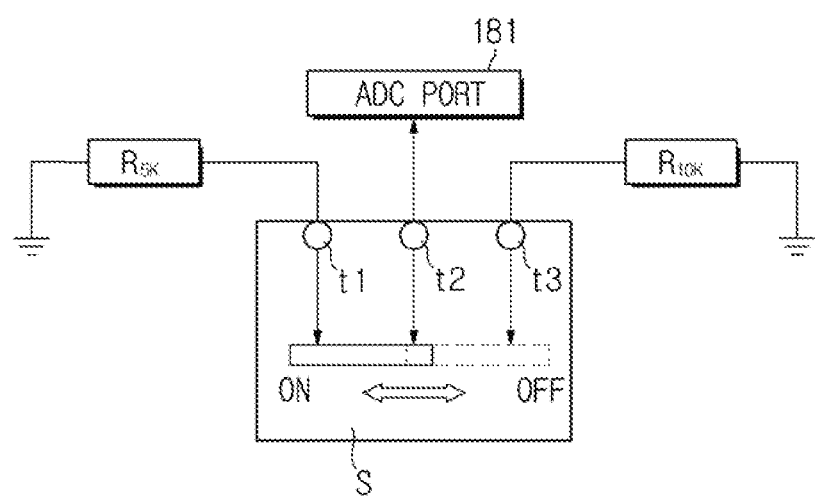
FIG. 19 is a circuit configuration diagram of a coupling module that is used in common.

FIG. 19 is a circuit configuration diagram of the coupling module 200 that is used in common.

Referring to FIG. 19, the coupling module 200 may include a switch S that can change a resistance value according to an on/off state, and a plurality of resistors having different resistance values. In the current example, the coupling module 200 is assumed to include a resistor $R_{5K}$ having a resistance value of 5KΩ and a resistor $R_{10K}$ having a resistance value of 10KΩ. The switch S may be a DIP switch. Three terminals (that is, first, second, and third terminals t1, t2, and t3) of the switch S may connect to the resistor $R_{5K}$ having a resistance value of 5KΩ, the ADC port 181, and the resistor $R_{10K}$ having a resistance value of 10KΩ, respectively. If a state in which the first terminal t1 is shorted to the second terminal t2 is defined as an on state, and a state in which the second terminal t2 is shorted to the third terminal t3 is defined as an off state, the switch S may be switched on to set an ID resistance value of the coupling module 200 to 5KΩ, and the switch S may be switched off to set an ID resistance value of the corresponding coupling module 200 to 10KΩ.

Meanwhile, for convenience of description, a case in which the X-ray imaging apparatus 1 includes a table coupling module 200-1, a stand coupling module 200-2, and a portable coupling module 200-3 has been described. However, the number of modules is not limited. In other words, both the radiography table 10 and the radiography stand 20 may be provided, or a plurality of radiography tables, such as a first radiography table and a second radiography table, and/or a plurality of radiography stands, such as a first radiography stand and a second radiography stand, may be provided.

When a plurality of radiography tables 10 are provided, the radiography tables 10 may include different coupling modules. Likewise, when a plurality of radiography stands 20 or a plurality of portable coupling modules 200-3 are provided, the radiography stands 20 may also include different coupling modules, or the portable coupling modules 2003 may be different coupling modules. For example, if a first table coupling module, a second table coupling module, a first stand coupling module, and a first portable coupling module are provided, the first table coupling module, the second table coupling module, the first stand coupling module, and the first portable coupling module are all different modules.

Different modules include different ID resistors. Accordingly, the number of digital values that can be output from the ADC port 181 corresponds to the number of different modules. For example, if a plurality of coupling modules corresponding to a first radiography table, a second radiography table, a first radiography stand, and a second radiography stand are provided, and a coupling module corresponding to the portable mode is provided, the number of digital values that can be output from the ADC port 181 is five in correspondence to the number of the different modules. In other words, a value that is output from the ADC port 181 when the X-ray detector 100 has been installed in the first radiography table, a value that is output from the ADC port 181 when the X-ray detector 100 has been installed in the second radiography table, a value that is output from the ADC port 181 when the X-ray detector 100 has been installed in the first radiography stand, a value that is output from the ADC port 181 when the X-ray detector 100 has been installed in the second radiography stand, and a value that is output from the ADC port 181 when the X-ray detector 100 is in the portable mode are different values. When the X-ray detector 100 has been installed in a predetermined module, the ADC port 181 outputs a constant value corresponding to the module.

Even when there are more or less modules than those shown in FIGS. 16 and 17, the location determiner 310 can determine an installation location of the X-ray detector 100 based on a digital value output from the ADC port 181.

In the current example, the ADC port 181 is an 8 bit ADC. However, the ADC port 181 may be a 4 bit ADC, a 10 bit ADC, a 12 bit ADC, or a 14 bit ADC according to the number of different modules.

Meanwhile, the same X-ray detector 100 may be used in the respective radiography modes as described above, or different X-ray detectors may be used in the respective radiography modes. The latter case corresponds to when a plurality of X-ray detectors are provided in a radiography room, and an X-ray detector that is suitable for a radiography mode is used. In this case, the use purposes of the respective X-ray detectors may have been set in advance. For example, if three radiography modes of the table mode, the stand mode, and the portable mode exist, three X-ray detectors may be provided in a radiography room, and the respective X-ray detectors may have been allocated to the corresponding radiography modes. Before radiography starts, a workstation may determine whether an X-ray detector corresponding to the corresponding radiography mode is at a proper location. Alternatively, although three X-ray detectors exist, the use purposes of the X-ray detectors may have not been set in advance, and whenever radiography is performed, the locations of the X-ray detectors may be determined. This will be described in detail with reference to FIG. 20.

FIGS. 20 and 21 show information that the location determiner 310 uses to determine a location of an X-ray detector when the X-ray detector has a unique IP address.

A plurality of X-ray detectors may have unique IP addresses. Referring to the example of FIG. 20, a first X-ray detector 100-1 may have an unique IP address of 192.168.0.1, a second X-ray detector 100-2 may have an unique IP address of 192.168.0.2, and a third X-ray detector 100-3 may have an unique IP address of 192.168.0.3.

The workstation 170 may transmit a signal (for example, a Ping signal) for identifying a device connected to the network hub 175, and the X-ray detector 100 connected to the network hub 175 may transmit an ack signal in response to the Ping signal. The ack signal may include an ADC level, together with a unique IP address of the X-ray detector 100.

As shown in FIG. 21, if the first X-ray detector 100-1 has been coupled with the table coupling module 200-1, the X-ray detector 100-1 may transmit an ack signal including an unique IP address of 192.168.0.1 and an ADC level of 255, in response to the Ping signal received from the workstation 170. Accordingly, the location determiner 310 may determine that the first X-ray detector 100-1 has been installed in the radiography table 10, that is, that the first X-ray detector 100-1 is in the table mode.

If the second X-ray detector 100-2 has been coupled with the stand coupling module 200-2, the second X-ray detector 100-2 may transmit an ack signal including an unique IP address of 192.168.0.2 and an ADC level of 170, in response to the Ping signal received from the workstation 170. Accordingly, the location determiner 310 may determine that the second X-ray detector 100-2 has been installed in the radiography stand 20, that is, that the second X-ray detector 100-2 is in the stand mode.

If the third X-ray detector 100-3 has been coupled with the portable coupling module 200-3, the third X-ray detector 100-3 may transmit an ack signal including an unique IP address of 192.168.0.3 and an ADC level of 127, in response to the Ping signal received from the workstation 170. Accordingly, the location determiner 310 may determine that the third X-ray detector 100-3 is in the portable mode.

In some cases, one of the three X-ray detectors 100-1, 100-2, and 100-3 may be coupled with a coupling module, or two or more of the three X-ray detectors 100-1, 100-2, and 100-3 may be coupled with coupling modules. If two X-ray detectors or more are coupled with coupling modules, for example, if the first X-ray detector 100-1 is installed in the radiography table 10, and the second X-ray detector 100-2 is installed in the radiography stand 20, both the first and second X-ray detectors 100-1 and 100-2 may generate ack signals, and transmit the ack signals to the workstation 170. If the ack signals include only unique IP addresses, the installed X-ray detectors 100-1 and 100-2 can be identified, but the locations of the X-ray detectors 100-1 and 10-2 cannot be determined. In the current example, an ack signal includes an ADC level indicating a location of the corresponding X-ray detector, together with an unique IP address. Accordingly, the location determiner 310 may accurately determine which X-ray detector is positioned in which location, although a plurality of X-ray detectors have been coupled with coupling modules. As a result, it is possible to prevent rescanning due to the case in which data is received from an X-ray detector not used for radiography or the case in which no data is received from an X-ray detector used for radiography.

The detector setting unit 320 may set an X-ray detector corresponding to a current radiography mode to a used X-ray detector, and enable the workstation 170 to receive data from the X-ray detector set to the used X-ray detector. For example, if a current radiography mode is the stand mode, and the location determiner 310 determines that the second X-ray detector 100-2 is in the stand mode, the detector setting unit 320 may set the second X-ray detector 100-2 to a used X-ray detector.

Meanwhile, the use purposes of the individual X-ray detectors may have been set in advance, as described above. That is, initial settings for the individual radiography modes may have been made in advance. For example, if the second X-ray detector 100-2 has been initially set to an X-ray detector that is used in the stand mode, and the location determiner 310 determines that the second X-ray detector 100-2 has been installed in the radiography stand 20, data from the second X-ray detector 100-2 may be received according to the initial setting.

However, if the first X-ray detector 100-1 has been initially set to an X-ray detector that is used in the stand mode, and the location determiner 310 determines that the second X-ray detector 100-2 is in the stand mode, the detector setting unit 320 may change the initial setting. That is, the detector setting unit 320 may reset the use purpose of the second X-ray detector 100-2 to the stand mode. However, it is also possible to temporarily reset an X-ray detector (that is, a used X-ray detector) that is currently used for radiography, without changing the initial setting.

As another example, the detector setting unit 320 (see FIG. 4) may set IP addresses in correspondence to the number of modules, and assign an IP address corresponding to an installation location of the X-ray detector 100 to the X-ray detector 100, or change an IP address assigned to the X-ray detector 100 according to an installation location of the X-ray detector 100.

First, the detector setting unit 320 may set IP addresses in correspondence with the number of modules. If there are a plurality of radiography tables 10, a plurality of radiography stands 20, and/or a plurality of portable coupling modules 200-3, for example, if there are a first radiography table, a second radiography table, a first radiography stand, a second radiography stand, and a first portable coupling module 200-3, the detector setting unit 320 may set an IP address for the first radiography table, an IP address for the second radiography table, an IP address for the first radiography stand, an IP address for the second radiography stand, and an IP address for the portable coupling module 200-3 to different values in correspondence with the number of the modules.

If there is a radiography table 10, a radiography stand 20, and a portable coupling module 200-3, the detector setting unit 320 may set an IP address for the radiography table 10, an IP address for the radiography stand 20, and an IP address for the portable coupling module 200-3 to different values. For example, the detector setting unit 320 may set an IP address for the radiography table 10 to 192.168.10.1, an IP address for the radiography stand 20 to 192.168.0.2, and an IP address for the portable coupling module 200-3 to 192.168.0.3.

Then, the detector setting unit 320 may assign an IP address to the X-ray detector 100 or change an IP address of the X-ray detector 100, based on a determination of the location determiner 310. This will be described in more detail with reference to FIG. 22, below. FIG. 22 is a view for describing an example of a method of assigning an IP address to the X-ray detector 100 and an example of a method of changing an IP address of the X-ray detector 100. The following description will be given based on the example of FIG. 16.

As described above with reference to FIG. 16, if the ADC port 181 has monitored a voltage $V_{11}$ and output a value of 255 corresponding to a level of the voltage $V_{11}$, the location determiner 310 may determine that the X-ray detector 100 has been installed in the radiography table 10. The detector setting unit 320 may assign the IP address 192.168.0.1 for the radiography table 10 to the X-ray detector 100 based on the determination of the location determiner 310. If an IP address that is different from 192.168.0.1 has already been assigned to the X-ray detector 100, the detector setting unit 320 may change the IP address of the X-ray detector 100 to 192.168.0.1 so that the IP address of the X-ray detector 100 is identical to the IP address for the radiography table 10.

If the ADC port 181 has monitored a voltage $V_{12}$ and output a value of 170 corresponding to a level of the voltage $V_{12}$, the location determiner 310 may determine that the X-ray detector 100 has been installed in the radiography stand 20. Accordingly, the detector setting unit 320 may assign the IP address 192.168.0.2 for the radiography stand 20 to the X-ray detector 100. If an IP address that is different from 192.168.0.2 has already been assigned to the X-ray detector 100, the detector setting unit 320 may change the IP address of the X-ray detector 100 to 192.168.0.2 so that the IP address of the X-ray detector 100 is identical to the IP address for the radiography stand 20.

If the ADC port 181 has monitored a voltage $V_{13}$ and output a value of 127 corresponding to a level of the voltage $V_{13}$, the location determiner 310 may determine that the X-ray detector 100 is in the portable mode. Accordingly, the detector setting unit 320 may assign the IP address 192.168.0.3 for portable to the X-ray detector 100. If an IP address that is different from 192.168.0.3 has already been assigned to the X-ray detector 100, the detector setting unit 320 may change the IP address of the X-ray detector 100 to 192.168.0.3 so that the IP address of the X-ray detector 100 is identical to the IP address for portable.

As such, because the detector setting unit 320 assigns an IP address to the X-ray detector 100 or changes an IP address of the X-ray detector 100 according to an installation location of the X-ray detector 100, the X-ray detector 100 can be used at various locations. For example, the X-ray detector 100 can be used in any one of the first radiography table, the second radiography table, the first radiography stand, the second radiography stand, and the first portable coupling module 200-3, and the X-ray detector 100 can be used in any one of the radiography table 10, the radiography stand 20, and the first portable coupling module 200-3.

Meanwhile, the user may apply power or torque to the handle 82 of the operating unit 80 (see FIG. 3), based on the determination of the location determiner 310 so as to move the X-ray source 70 to correspond to the location of the X-ray detector 100. This is the manual move mode defined above.

The automatic move mode can be defined in correspondence to the manual move mode. In the automatic move mode, the motor controller 340 controls driving of the motor unit 110 in order to move the X-ray source 70.

More specifically, if a user sets a radiography mode based on a determination of the location determiner 310, the motor controller 340 may detect locations of the X-ray source 70 and the X-ray detector 100, and output a control signal(s) to a motor(s) that needs to be driven. The X-ray source 70 may move to correspond to the location of the X-ray detector 100 according to driving of the motor unit 110. The user's setting may be done through the first display unit 81, the buttons 84, or the input unit 171 or the second display unit 172 of the workstation 170. A mode of moving the X-ray source 70 according to a user's setting is defined as the automatic move mode.

Figure 23:
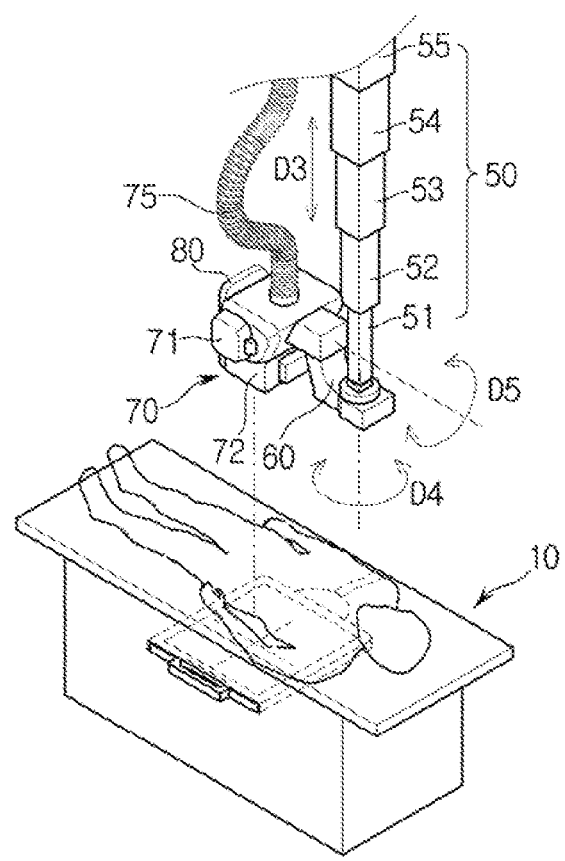
FIGS. 23 to 25 are views for describing movement of an X-ray source in an automatic move mode.
Figure 24:
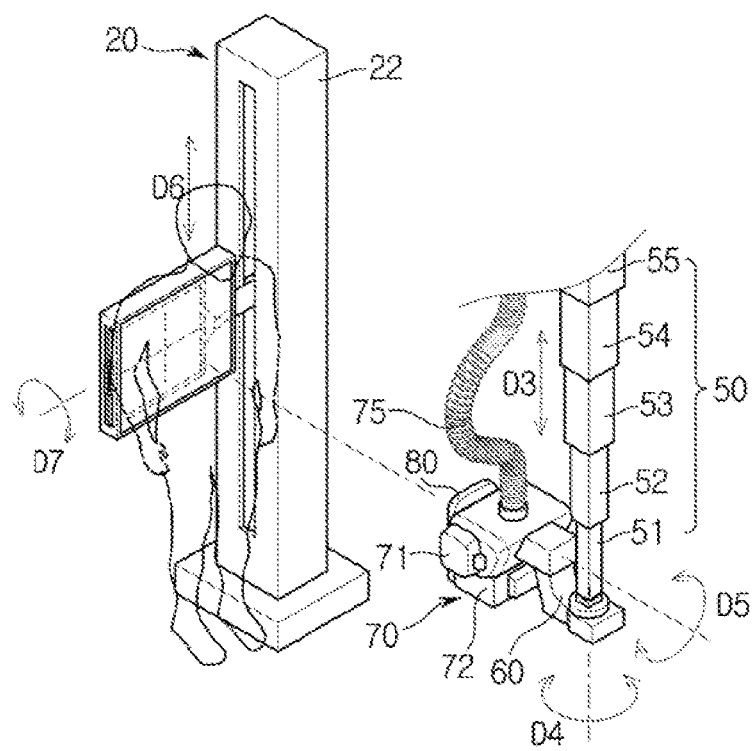
Figure 25:
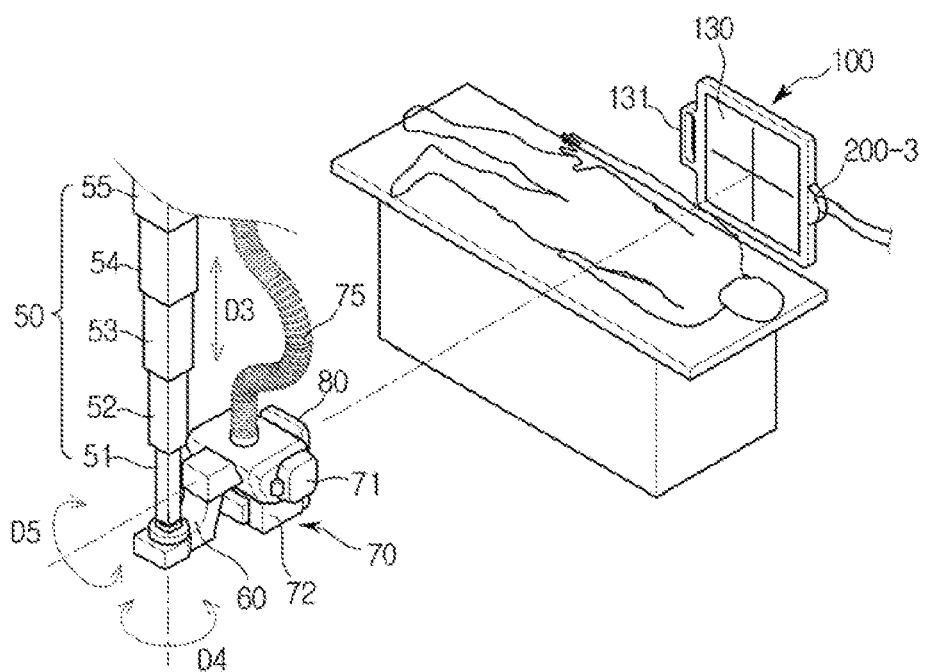

FIGS. 23, 24, and 25 are views for describing movement of the X-ray source 70 in the automatic move mode. In FIGS. 23, 24, and 25, a case in which there is a radiography table 10, a case in which there is a radiography stand 20, and a case in which there is a portable coupling module 200-3 are respectively shown.

If the location determiner 310 determines that the X-ray detector 100 has been installed in the radiography table 10, a user may set a radiography mode to "table". According to the user's setting, the motor controller 340 (see FIG. 4) may output a control signal for controlling driving of the motor unit 110 in order to move the X-ray source 70 to the radiography table 10. If the motor unit 110 is driven according to the control signal, the X-ray source 10 moves to the location of the X-ray detector 100 installed in the radiography table 10, as illustrated in FIG. 23. In this state, X-rays irradiated from the X-ray source 70 can be detected by the X-ray detector 100 installed in the radiography table 10.

If the location determiner 310 determines that the X-ray detector 100 has been installed in the radiography stand 20, the user may set a radiography mode to "stand". According to the user's setting, the motor controller 340 may output a control signal for controlling driving of the motor unit 110 in order to move the X-ray source 70 to the radiography stand 20. If the motor unit 110 is driven according to the control signal, the X-ray source 10 moves to the location of the X-ray detector 100 installed in the radiography stand 20, as illustrated in FIG. 24. In this state, X-rays irradiated from the X-ray source 70 can be detected by the X-ray detector 100 installed in the radiography stand 20.

If the location determiner 310 determines that the X-ray detector 100 has been installed in the portable coupling module 200-3, the user may set a radiography mode to "portable". According to the user's setting, the motor controller 340 may output a control signal for controlling driving of the motor unit 110 in order to move the X-ray source 70 to the portable coupling module 200-3. If the motor unit 110 is driven according to the control signal, the X-ray source 10 moves to the location of the X-ray detector 100 installed in the radiography portable 30, as illustrated in FIG. 25. In this state, X-rays irradiated from the X-ray source 70 can be detected by the X-ray detector 100 installed in the portable coupling module 200-3.

Unlike the cases shown in FIGS. 23, 24, and 25, a case in which there are a plurality of radiography tables 10, a case in which there are a plurality of radiography stands 20, or a case in which there are a plurality of portable coupling module 200-3 can be considered. For example, a case in which there are a first radiography table, a second radiography table, a first radiography stand, a second radiography stand, and a portable coupling module 200-3 can be considered. In this case, if the location determiner 310 determines that the X-ray detector 100 has been installed in the first radiography table, the user may set a radiography mode to "first table". According to the user's setting, the motor controller 340 may output a control signal(s) to a motor(s) that needs to be driven, and the motor unit 110 is driven according to the control signal to move the X-ray source 10 to correspond to the location of the X-ray detector 100 installed in the first radiography table.

Alternatively, a radiography mode may be set regardless of a current location of an X-ray detector. In this case, a radiography mode may be selected by a user, or a location of an X-ray detector may be determined as in the above-described examples. For example, if a user selects the table mode as a radiography mode, and the location determiner 310 determines that the first X-ray detector 100-1 is in the table mode, the detector setting unit 320 may set the first X-ray detector 100-1 as a used X-ray detector, and receive data from the first X-ray detector 100-1. If the initially set use purpose of the first X-ray detector 100-1 is not the table mode, the detector setting unit 320 may change or maintain the initial setting. In this case, the motor controller 340 may output a control signal to the motor 110 according to an input from the user.

The location determiner 310, the detector setting unit 320, and the motor controller 340 may be installed in one unit or in different units. For example, all of the location determiner 310, the detector setting unit 320, and the motor controller 340 may be installed in the workstation 170 (see FIG. 1). As an example, the location determiner 310 and the detector setting unit 320 may be installed in the workstation 170, and the motor controller 340 may be installed in the carriage 45 (see FIG. 1).

The X-ray imaging apparatus 1 may further include a storage unit, and the storage unit may store data or algorithms for manipulating the X-ray imaging apparatus 1.

For example, the storage unit may store a digital value output from the ADC port 181 (see FIG. 4). Referring again to FIG. 21, the storage unit may store a value of 255 when the X-ray detector 100 has been installed in the radiography table 10, a value of 170 when the X-ray detector 100 has been installed in the radiography stand 20, and a value of 127 when the X-ray detector 1 is in the portable mode. As another example, the storage unit may store IP addresses set in correspondence to the number of modules. Referring again to FIG. 22, the storage unit may store 192.168.0.1 set to an IP address for a radiography table, 192.168.0.2 set to an IP address for a radiography stand, and 192.168.0.3 set to an IP address for portable.

Also, the storage unit may map unique IP addresses of the individual X-ray detectors to initially set use purposes (radiography modes) of the X-ray detectors, and store the results of the mapping. After the location determiner 310 determines locations of X-ray detectors, the storage unit may set an X-ray detector that is in a current radiography mode, to a used X-ray detector, and store the result of the setting.

Also, the storage unit may store an algorithm for converting a monitored voltage into a digital value, and an algorithm for determining an installation location of the X-ray detector 100 based on the digital value.

The storage unit may be Read Only Memory (ROM), Programmable Read Only Memory (PROM), Erasable Programmable Read Only Memory (EPROM), non-volatile memory such as flash memory, volatile memory such as Random Access Memory (RAM), a hard disk, or an optical disk. However, the storage unit is not limited to the above-mentioned devices, and may be any other device well-known in the art.

Figure 26:
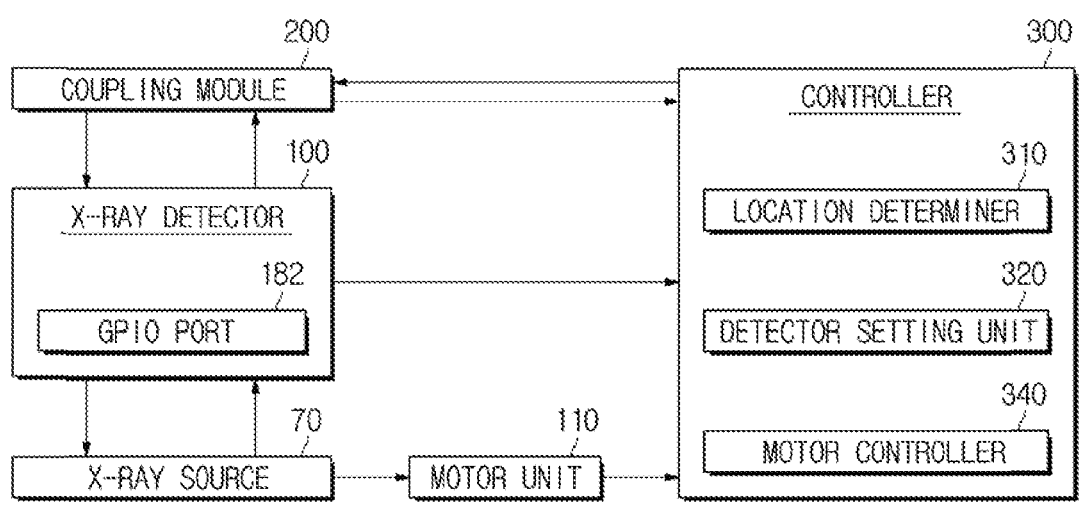
FIG. 26 is a control block diagram of an X-ray imaging apparatus according to an embodiment of the present disclosure.

FIG. 26 is a control block diagram of an X-ray imaging apparatus according to another embodiment of the present disclosure.

Referring to FIG. 26, an X-ray imaging apparatus 1 may include an X-ray source 70, the X-ray detector 100, a coupling module 200, a controller 300, and a motor unit 110. The controller 300 may determine a location of the X-ray detector 100, and move the X-ray source 70 to correspond to the location of the X-ray detector 100.

The X-ray source 70 and the motor unit 110 are the same as the X-ray source 70 and the motor unit 110 described above in the embodiment of FIG. 4, and accordingly, further descriptions thereof will be omitted. Also, in the following descriptions about the X-ray detector 100, the coupling module 200, and the controller 300, the same parts are described above with reference to FIG. 4, and descriptions thereof will be omitted.

The controller 300 may include a location determiner 310, a detector setting unit 320, and a motor controller 340.

The location determiner 310 may determine an installation location of the X-ray detector 100. In order to help a determination of the location determiner 310, the X-ray detector 100 may include a monitoring unit for monitoring a voltage. In the above-described embodiment, the ADC port 181 is used as the monitoring unit for monitoring a voltage, however, in the current embodiment, a General Purpose Input/Output (GPIO) port 182 may be used as the monitoring unit for monitoring a voltage. The individual coupling modules 200-1, 200-2, and 200-3 included in the coupling module 200 include unique ID resistors. A method in which the location determiner 310 determines an installation location of the X-ray detector 100 using the port and the ID resistors will be described in detail with reference to FIGS. 27 and 28, below.

Figure 27:
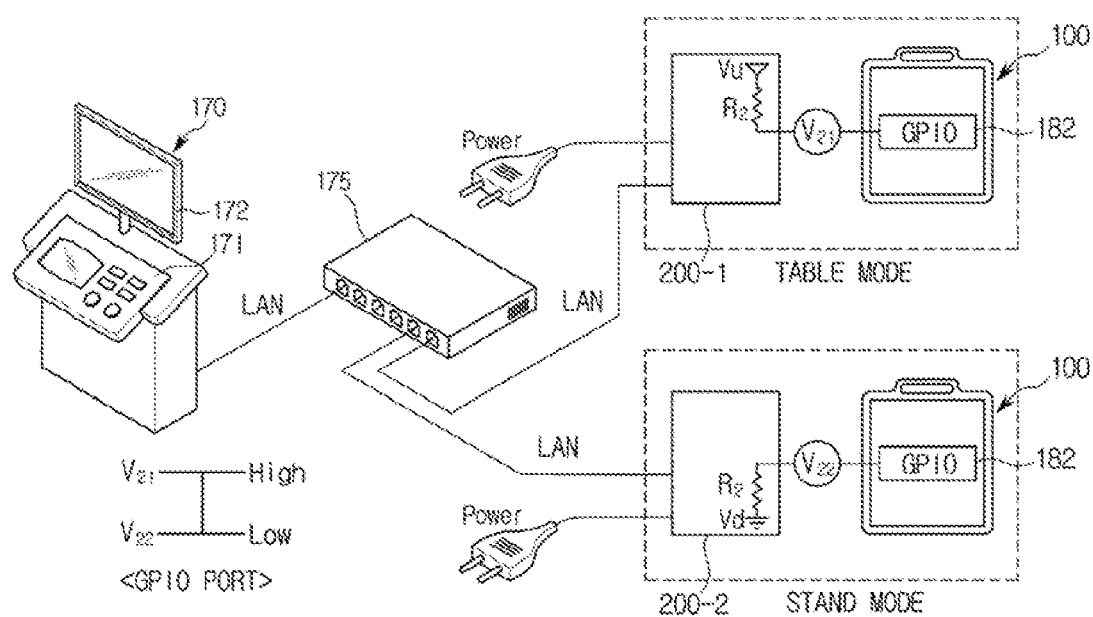
FIG. 27 is a view for describing an example of a method of determining an installation location of an X-ray detector based on the control block diagram of FIG. 26.

FIG. 27 is a view for describing an example of a method of determining an installation location of the X-ray detector 100 based on the control block diagram of FIG. 26. In FIG. 27, a case in which there is a radiography table 10 and a radiography stand 20, and the location determiner 310 determines which one of the radiography table 10 and the radiography stand 20 the X-ray detector 100 has been installed in is shown.

The X-ray detector 100 may include a port for monitoring a voltage and outputting a relative level of the voltage. In FIG. 27, the port is a GPIO port 182. The table coupling module 200-1 includes a pull-up ID resistor $R_2$, and the stand coupling module 200-2 includes a pull-down ID resistor $R_2$. The pull-up ID resistor $R_2$ and the pull-down ID resistor $R_2$ have the same resistance value of $R_2$.

Because the ID resistor included in the table coupling module 200-1 is a pull-up resistor and the ID resistor included in the stand coupling module 200-2 is a pull-down resistor although the ID resistors have the same resistance value, a value that the GPIO port 181 monitors may vary depending on which module the X-ray detector 100 has been installed in.

More specifically, if the X-ray detector 100 has been installed in the radiography table 10, the GPIO port 182 may monitor a voltage $V_{21}$ applied to an ID check line in correspondence to the pull-up ID resistor $R_2$ included in the table coupling module 200-1. If the X-ray detector 100 has been installed in the radiography stand 20, the GPIO port 182 may monitor a voltage $V_{22}$ applied to an ID check line in correspondence to the pull-down ID resistor $R_2$ included in the stand coupling module 200-2. Because the ID resistor included in the table coupling module 200-1 is a pull-up resistor and the ID resistor included in the stand coupling module 200-2 is a pull-down resistor, in other words, because a voltage Vu that is applied to the table coupling module 200-1 is higher than a voltage Vd that is applied to the stand coupling module 200-2, the GPIO port 182 may monitor different voltages of $V_{21}$ and $V_{22}$ depending on an installation location of the X-ray detector 100. For example, if $R_2$ is 5KΩ, Vu is 5V, and Vd is 0V, the voltage $V_{21}$ becomes 5V and the voltage $V_{22}$ becomes 0V.

The GPIO port 182 may output a relative level of a monitored voltage to the location determiner 310. Because a voltage that is monitored by the GPIO port 182 depends on which module the X-ray detector 100 has been installed in, a value that is output from the GPIO port 182 to the location determiner 310 also depends on which module the X-ray detector 110 has been installed in.

For example, if the X-ray detector 100 has been installed in the radiography table 10, and the GPIO port 182 has monitored a voltage V21 (e.g., 5V), the GPIO port 182 may output a high level corresponding to a relative level of 5V to the location determiner 310. If the X-ray detector 100 has been installed in the radiography stand 20, and the GPIO port 182 has monitored a voltage $V_{22}$ (e.g., 0V), the GPIO port 182 may output a low level corresponding to a relative level of 0V to the location determiner 310.

Because the ID resistors have the same resistance value of $R_2$, and a voltage that is applied to the X-ray detector 100 is constant in a module, the GPIO port 182 may output a constant value when the X-ray detector 100 has been installed in a module. If the X-ray detector 100 has been installed in the radiography table 10, the GPIO port 182 may output a high level, and if the X-ray detector 100 has been installed in the radiography stand 20, the GPIO port 182 may output a low level.

Accordingly, the location determiner 310 may determine an installation location of the X-ray detector 100 based on an output value from the GPIO port 182. If the GPIO port 182 has output a high level, the location determiner 310 may determine that the X-ray detector 100 has been installed in the radiography table 10, and if the GPIO port 182 has output a low level, the location determiner 310 may determine that the X-ray detector 100 has been installed in the radiography stand 20.

The output value from the GPIO port 182 may be transmitted to the workstation 170, together with the unique IP address of the corresponding X-ray detector 100. Accordingly, the location determiner 310 may determine which X-ray detector is positioned at which location, using the output value of the GIP port 182 and the unique IP address.

Meanwhile, if the X-ray imaging apparatus 1 further includes a storage unit, the storage unit may store an output value from the GPIO port 182 according to an installation location of the X-ray detector 100. In other words, the storage unit may store a high level when the X-ray detector 100 has been installed in the radiography table 10, and store a low level when the X-ray detector 100 has been installed in the radiography stand 20.

Figure 28:
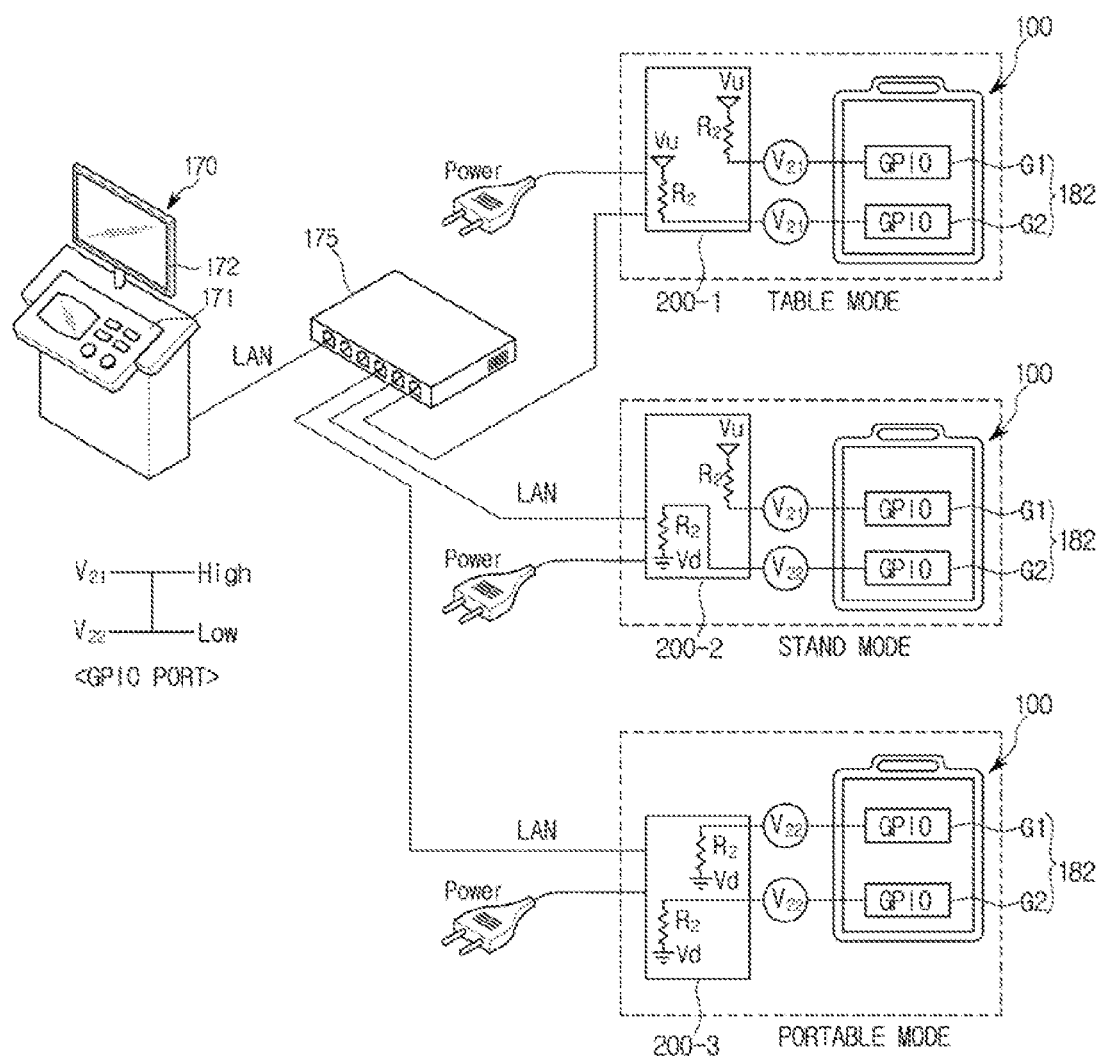
FIG. 28 is a view for describing another example of a method of determining an installation location of an X-ray detector based on the control block diagram of FIG. 26.

FIG. 28 is a view for describing an example of a method of determining an installation location of the X-ray detector 100 based on the control block diagram of FIG. 26, and FIG. 29 shows an example of information which the location determiner 310 uses to determine a location of the X-ray detector 100 in the example of FIG. 28. In FIG. 28, a case in which there is a radiography table 10, a radiography stand 20, and a portable coupling module 200-3, and the location determiner 310 determines which one of the radiography table 10, the radiography stand 20, and the portable coupling module 200-3 the X-ray detector 100 has been installed in or coupled with is shown.

Referring to FIG. 28, the X-ray detector 100 may include two GPIO ports 182, that is, a first GPIO port G1 and a second GPIO port G2. Also, each of first, second, and third coupling modules 200-1, 200-2, and 200-3 includes two ID resistors. More specifically, the table coupling module 200-1 includes two pull-up ID resistors, the stand coupling module 200-2 includes a pull-up ID resistor and a pull-down ID resistor, and the portable coupling module 200-3 includes two pull-down ID resistors. All of the pull-up ID resistors and the pull-down ID resistors have the same resistance value of $R_2$. The ID resistors included in each of the coupling modules 200-1, 200-2, and 200-3 can be expressed as an ordered pair according to an order in which the ID resistors are connected to the GPIO port 182. For example, the ID resistors included in the stand coupling module 200-2 may be expressed as an ordered pair of a pull-up ID resistor $R_2$ and a pull-down ID resistor $R_2$.

The first GPIO port G1 and the second GPIO port G2 may monitor voltages applied to ID check lines, respectively.

More specifically, if the X-ray detector 100 has been coupled with the table coupling module 200-1, the first GPIO port G1 and the second GPIO port G2 may monitor a voltage $V_{21}$ in correspondence to the pull-up ID resistors $R_2$. If the X-ray detector 100 has been coupled with the stand coupling module 200-2, the first GPIO port G1 may monitor a voltage $V_{21}$ in correspondence to the pull-down ID resistor $R_2$, and the second GPIO port G2 may monitor a voltage $V_{22}$ in correspondence to the pull-down ID resistor $R_2$. If the X-ray detector 100 has been coupled with the portable coupling module 200-3, the first and second GPIO ports G1 and G2 may monitor a voltage $V_{22}$ in correspondence to the pull-down ID resistors $R_2$.

The first and second GPIO ports G1 and G2 may output relative levels of the monitored voltages to the location determiner 310.

Referring to the example of FIG. 29, if the first X-ray detector 100-1 is in the table mode so that the first and second GPIO ports G1 and G2 have monitored a voltage $V_{21}$ (e.g., 5V), the first and second GPIO ports G1 and G2 may transmit a high level corresponding to a relative level of 5V to the location determiner 310. The levels may be transmitted together with a unique IP address of the first X-ray detector 100-1. Herein, unique IP addresses of the first X-ray detector 100-1, the second X-ray detector 100-2, and the third X-ray detector 100-3 are assumed to be values as shown in FIG. 20. The location determiner 310 may determine that the first X-ray detector 100-1 is in the table mode, based on the GPIO level and the unique IP address.

If the second X-ray detector 100-2 is in the stand mode so that the first GPIO port G1 and the second GPIO port G2 have monitored a voltage V21 (e.g., 5V) and a voltage $V_{22}$ (e.g., 0V), respectively, the first GPIO port G1 may output a high level corresponding to a relative level of 5V to the location determiner 310, and the second GPIO port G2 may transmit a low level corresponding to a relative level of 0V to the location determiner 310. The levels may be transmitted together with a unique IP address of the second X-ray detector 100-2. The location determiner 310 may determine that the second X-ray detector 100-2 is in the stand mode, based on the GPIO level and the unique IP address.

If the third X-ray detector 100-3 is in the portable mode so that the first and second GPIO ports G1 and G2 have monitored a voltage $V_{22}$ (e.g., 0V), the first and second GPIO ports G1 and G2 may transmit a low level corresponding to a relative level of 0V to the location determiner 310. The levels may be transmitted together with a unique IP address of the third X-ray detector 100-3. The location determiner 310 may determine that the third X-ray detector 100-3 is in the portable mode, based on the GPIO level and the unique IP address.

Accordingly, the location determiner 310 may determine which X-ray detector 100 is in which radiography mode, based on the output values from the first and second GPIO ports G1 and G2 and the unique IP address of the X-ray detector 100. In summary, in the example of FIG. 29, if all of the first and second GPIO ports G1 and G2 have output a high level, the location determiner 310 may determine that the X-ray detector 100 is in the table mode, and if the first GPIO port G1 has output a high level and the second GPIO port G2 has output a low level, the location determiner 310 may determine that the X-ray detector 100 is in the stand mode. Also, if all of the first and second GPIO ports G1 and G2 have output a low level, the location determiner 310 may determine that the X-ray detector 100 is in the portable mode.

The GPIO level may be, like an ADC level, included in an ack signal responding to a Ping signal from the workstation 170. If the ack signal includes only the unique IP address of the corresponding X-ray detector, which X-ray detector has been installed can be determined, but, a location of the X-ray detector cannot be determined. According to the current example, since an ack signal includes an unique IP address of an X-ray detector and a GPIO level that is used to determine a location of the corresponding X-ray detector, the location determiner 310 may determine which X-ray detector has been positioned at which location, even when a plurality of X-ray detectors have been coupled with the coupling modules.

Meanwhile, the output values of the GPIO ports 182 may be expressed as an ordered pair according to an order of the GPIO ports 190. For example, if the X-ray detector 100 has been installed in the radiography stand 20 so that the first GPIO port G1 has output a high level and the second GPIO port G2 has output a low level, the output values of the GPIO ports 182 may be expressed as an ordered pair (High, Low).

If the X-ray imaging apparatus 1 further includes a storage unit, the storage unit may store output values of the first and second GPIO ports G1 and G2 according to a location of the X-ray detector 100. The storage unit may store a high level output from the first and second GPIO ports G1 and G2 when the X-ray detector 100 has been installed in the radiography table 10, a high level output from the first GPIO port G1 and a low level output from the second GPIO port G2 when the X-ray detector 100 has been installed in the radiography stand 20, and a low level output from the first and second GPIO ports G1 and G2 when the X-ray detector 100 has been coupled with the portable coupling module 200-3, that is, when the X-ray detector 100 is in the portable mode.

For convenience of description, a case in which the X-ray imaging apparatus 1 includes a radiography table 10 and a radiography stand 20, or a case in which the X-ray imaging apparatus 1 includes a radiography table 10, a radiography stand 20, and a portable coupling module 200-3 has been described. However, the number of modules is not limited.

One or more GPIO ports 182 may be provided according to the number of modules. Also, one or more ID resistors may be provided according to the number of the GPIO ports 182 so that the ID resistors can one-to-one match the GPIO ports 182. The ID resistors have a different configuration for each coupling module 200 so that output values from the GPIO ports 182 vary depending on which module the X-ray detector 100 has been installed in.

Accordingly, even when the number of modules is greater or smaller than those illustrated in FIGS. 27 and 28, the location determiner 310 may determine an installation location of the X-ray detector 100 based on output values of the GPIO ports 182.

The detector setting unit 320 may set, as described above, an X-ray detector corresponding to a selected radiography mode to a used X-ray detector to receive data. If the use purposes of X-ray detectors have been set in advance, the detector setting unit 320 may change the initial settings of the X-ray detectors, or set a used X-ray detector without changing the initial settings of X-ray detectors. Since this operation has been described above, a detailed description thereof will be omitted.

As another example, the detector setting unit 320 may set IP addresses in correspondence to the number of modules, and assign an IP address corresponding to an installation location of the X-ray detector 100 to the X-ray detector 100, or change the IP address assigned to the X-ray detector 100 according to an installation location of the X-ray detector 100.

FIG. 30 is a view for describing a method of assigning an IP address to the X-ray detector 100 and a method of changing an IP address of the X-ray detector 100. In FIG. 30, an IP address for a radiography table 10 has been set to 192.168.0.1, an IP address for a radiography stand 20 has been set to 192.168.0.2, and an IP address for portable has been set to 192.168.0.3, based on the example shown in FIG. 28.

As described above with reference to FIG. 28, if the first and second GPIO ports G1 and G2 have monitored a voltage $V_{21}$ and output a high level corresponding to a relative level of the voltage $V_{21}$, the location determiner 310 may determine that the X-ray detector 100 has been installed in the radiography table 10. Based on the determination of the location determiner 310, the detector setting unit 320 may assign the IP address 192.168.0.1 for the radiography table 10 to the X-ray detector 100. If an IP address that is different from 192.168.0.1 has been assigned to the X-ray detector 100, the detector setting unit 320 may change the IP address of the X-ray detector 100 to 192.168.0.1 so that the IP address of the X-ray detector 100 is identical to the IP address for the radiography table 10.

If the first GPIO port G1 has monitored a voltage $V_{12}$ and output a high level while the second GPIO port G2 has monitored a voltage $V_{22}$ and output a low level, the location determiner 310 may determine that the X-ray detector 100 has been installed in the radiography stand 20. Accordingly, the detector setting unit 320 may assign the IP address 192.168.0.2 for the radiography stand 20 to the X-ray detector 100. If an IP address that is different from 192.168.0.2 has been assigned to the X-ray detector 100, the detector setting unit 320 may change the IP address of the X-ray detector 100 to 192.168.0.2 so that the IP address of the X-ray detector 100 is identical to the IP address for the radiography stand 20.

If the first and second GPIO ports G1 and G2 have monitored a voltage $V_{22}$ and output a low level corresponding to a relative level of the voltage $V_{22}$, the location determiner 310 may determine that the X-ray detector 100 is in the portable mode. Accordingly, the detector setting unit 320 may assign the IP address 192.168.0.3 for portable to the X-ray detector 100. If an IP address that is different from 192.168.0.3 has been assigned to the X-ray detector 100, the detector setting unit 320 may change the IP address of the X-ray detector 100 to 192.168.0.3 so that the IP address of the X-ray detector 100 is identical to the IP address for portable.

As such, because the detector setting unit 320 assigns an IP address to the X-ray detector 100 or changes an IP address of the X-ray detector 100 according to an installation location of the X-ray detector 100, the X-ray detector 100 can be used at various locations.

Figure 31:
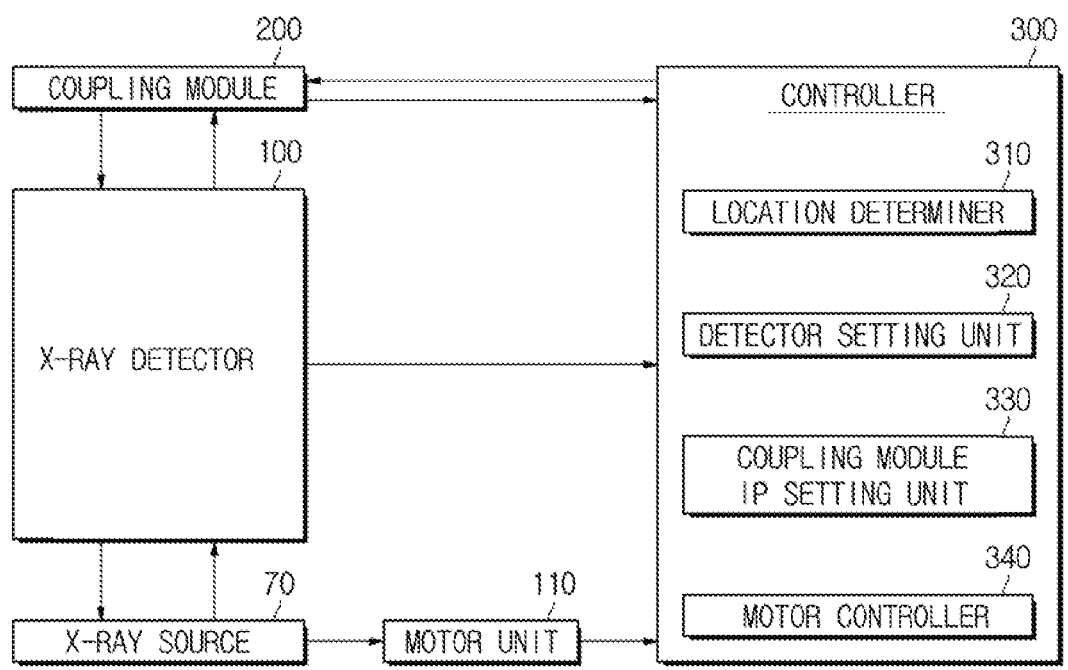
FIG. 31 is a control block diagram of an X-ray imaging apparatus according to still another embodiment of the present disclosure.

FIG. 31 is a control block diagram of an X-ray imaging apparatus according to an embodiment of the present disclosure.

Referring to FIG. 31, an X-ray imaging apparatus 1 may include an X-ray source 70, the X-ray detector 100, a coupling module 200, a controller 300, and a motor unit 110, and the controller 300 may determine a location of the X-ray detector 100 to move the X-ray source 70 to correspond to the location of the X-ray detector 100. The controller 300 may include a location determiner 310, a detector setting unit 320, a coupling module IP setting unit 330, and a motor controller 340.

The X-ray source 70, the X-ray detector 100, the motor unit 110, and the motor controller 340 are the same components as those used in the above-described embodiments, and accordingly, further descriptions thereof will be omitted. Also, in the following descriptions about the coupling module 200, the location determiner 310, and the detector setting unit 320, the same parts as those described in the above embodiments will be omitted.

Figure 32:
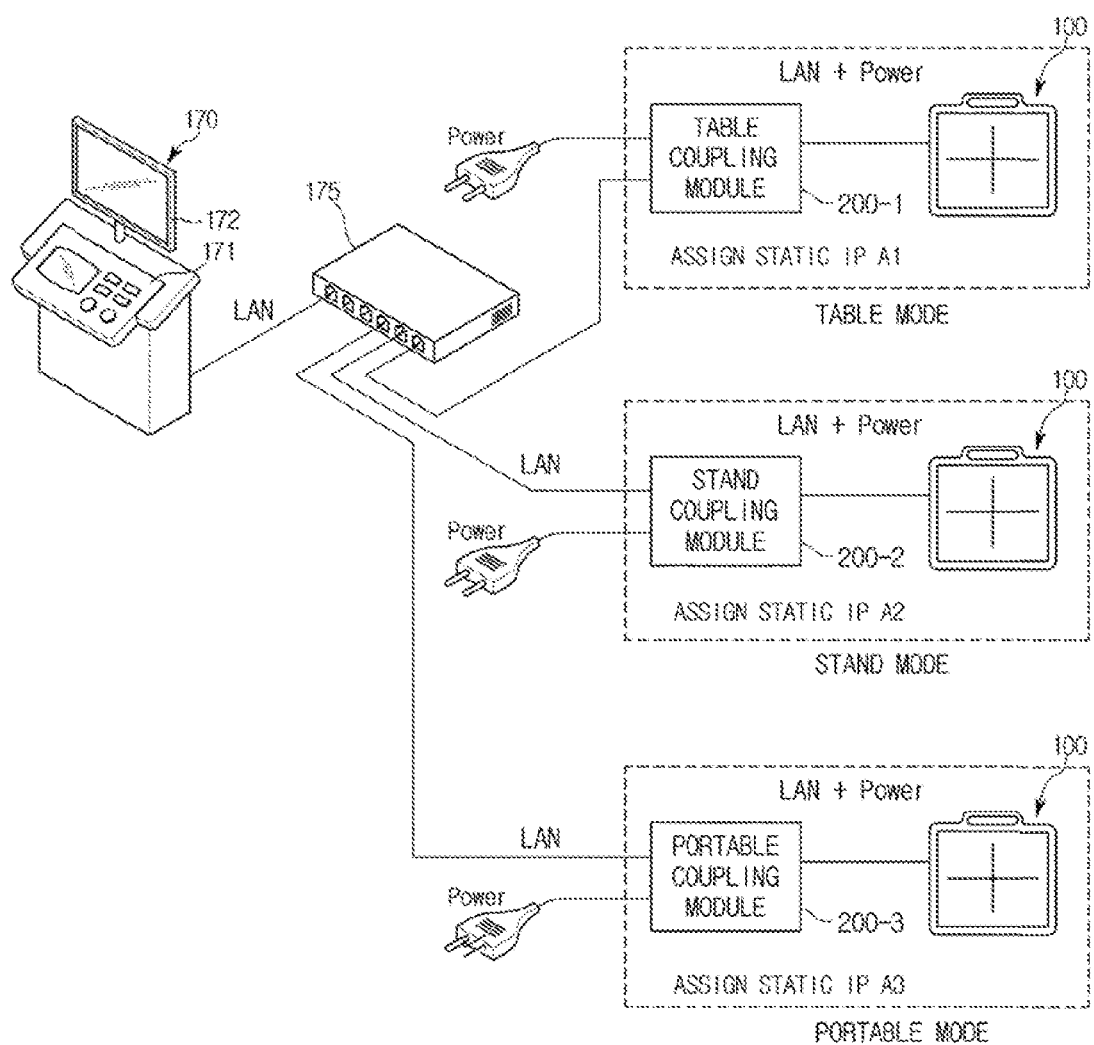
FIG. 32 is a view for describing an example of a method of determining an installation location of an X-ray detector based on the control block diagram of FIG. 31.

FIG. 32 is a view for describing an example of a method of determining an installation location of the X-ray detector 100 based on the control block diagram of FIG. 31. In the example of FIG. 32, a table coupling module 200-1, a stand coupling module 200-2, and a portable coupling module 200-3 are provided. Accordingly, the location determiner 310 may determine which one of the table coupling module 200-1, the stand coupling module 200-2, and the portable coupling module 200-3 the X-ray detector 100 has been coupled with.

Referring to FIG. 32, the coupling module IP setting unit 330 may set IP addresses in correspondence to the number of modules, and assign the IP addresses, respectively, to the coupling modules 200-1, 200-2, and 200-3. The IP addresses assigned to the respective coupling modules 200-1, 200-2, and 200-3 do not change. That is, the coupling module IP setting unit 330 may assign static IP addresses to the coupling modules 200-1, 200-2, and 200-3, respectively.

More specifically, the coupling module IP setting unit 330 may set a static IP address for the radiography table 10 to A1, a static IP address for the radiography stand 20 to A2, and a static IP address for portable to A3, respectively, in correspondence to the number of modules. Then, the coupling module IP setting unit 330 may assign the static IP address A1 to the first coupling module 200-1, the static IP address A2 to the second coupling module 200-2, and the static IP address A3 to the third coupling module 200-3. The static IP addresses A1, A2, and A3 are different values.

Thereafter, the location determiner 310 determines an installation location of the X-ray detector 100. At this time, a static IP address assigned to a coupling module 200 is used. More specifically, before determining an installation location of the X-ray detector 100, the location determiner 310 may request the coupling module 200 to send a static IP address and a unique IP address of the X-ray detector 100 coupled with the coupling module 200. At this time, the coupling module 200 may communicate with the workstation 170. For example, if a unique IP address assigned to the X-ray detector 100 is B2, and a static IP address of the coupling module 200 coupled with the X-ray detector 100 is A1, the location determiner 310 may determine that the second X-ray detector 100-2 has been coupled with the table coupling module 200-1, that is, that the second X-ray detector 100-2 is in the table mode.

As another example, the detector setting unit 320 may set IP addresses in correspondence to the number of modules, and assign an IP address to the X-ray detector 100, and maintain or change the IP address assigned to the X-ray detector 100 according to an installation location of the X-ray detector 100.

First, the detector setting unit 320 may set IP addresses in correspondence to the number of modules, and assign an IP address to the X-ray detector 100. More specifically, the detector setting unit 320 may set an IP address for the radiography table 10 to B1, an IP address for the radiography stand 20 to B2, and an IP address for portable to B3, in correspondence to the number of modules. Then, the detector setting unit 320 may assign an IP address to the X-ray detector 100 according to the set IP addresses. That is, the IP address assigned to the X-ray detector 100 may be any one of B1, B2, and B3.

The detector setting unit 320 may maintain or change an IP address of the X-ray detector 100 according to the installation location of the X-ray detector 100. Because the X-ray detector 100 allocated an IP address B2, that is, the X-ray detector 100 for the radiography stand 20 has been installed in the radiography table 10, the detector setting unit 320 may change the IP address of the X-ray detector 100 from B2 to B1 to thus convert the X-ray detector 100 for the radiography stand 20 to the X-ray detector 100 for the radiography table 10.

Meanwhile, if the X-ray imaging apparatus 1 further includes a storage unit, the storage unit may store the IP addresses for the coupling modules 200 and the IP addresses for the X-ray detector 100, set in correspondence to the number of modules. Referring again to FIG. 32, the storage unit may store A1 set to an IP address for the radiography table 10, A2 set to an IP address for the radiography stand 20, and A3 set to an IP address for portable so that the IP addresses A1, A2, and A3 can be assigned to the coupling modules. Also, the storage unit may store B1 set to an IP address for the radiography table 10, B2 set to an IP address for the radiography stand 20, and B3 set to an IP address for portable so that the IP address B1, B2, or B3 can be assigned to the X-ray detector 100.

The storage unit may store algorithms for determining an installation location of the X-ray detector 100 using a static IP address of a coupling module 200.

Meanwhile, the coupling module 200 may assign its own static IP address. This operation will be described with reference to FIG. 33, below.

Figure 33:
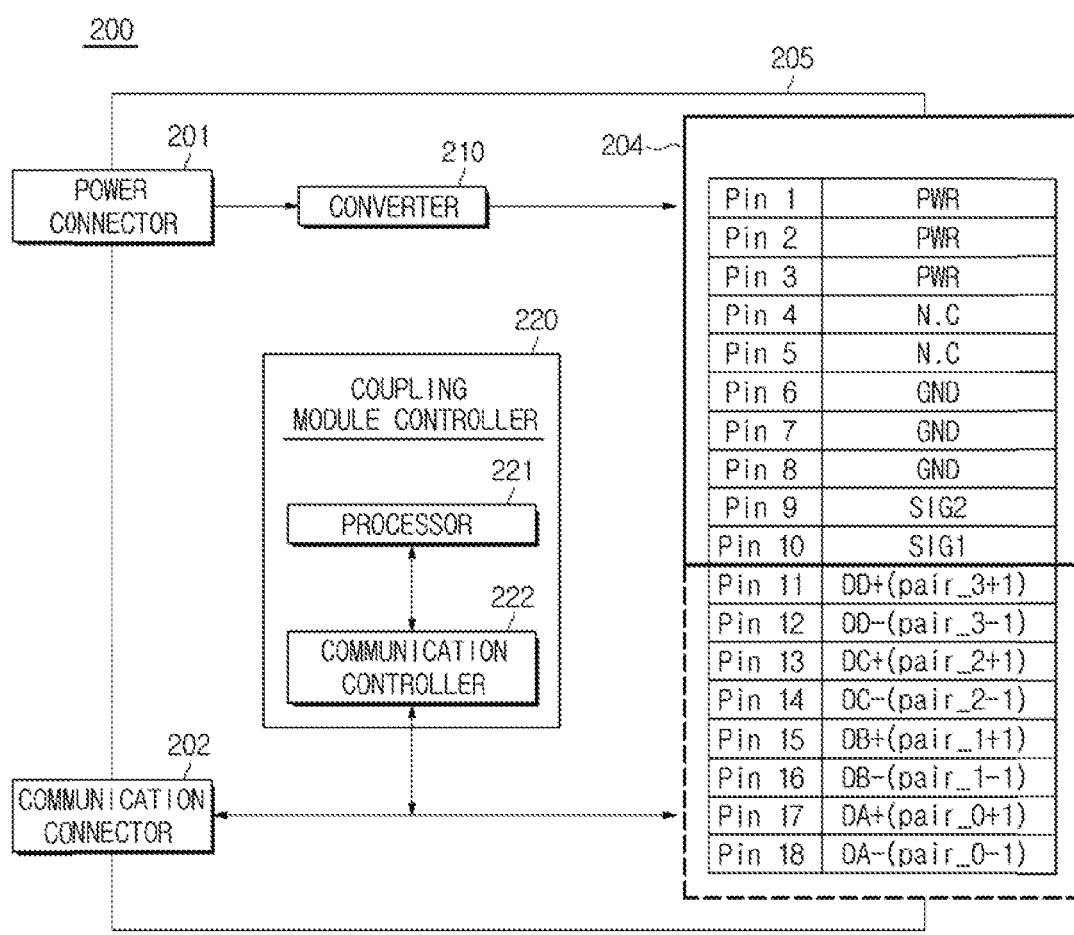
FIG. 33 shows an internal configuration of a coupling module of assigning a static IP address.

FIG. 33 shows an internal configuration of a coupling module 200 of assigning a static IP address.

Referring to FIG. 33, the coupling module 200 may include a coupling module controller 220 to assign a static IP address and to control communication. The coupling module controller 220 may include a processor 221 to assign a static IP address, and a communication controller 222 to control communications between the network hub 175 and the X-ray detector 100.

As described above, the coupling module 200 may further include a converter 210 to convert an AC voltage received from a power supply unit into a DC voltage. In the following description, descriptions about the same components as those described above with reference to FIG. 18 will be omitted.

Even in the case in which the coupling module 200 itself assigns its own static IP address, the coupling module 200 may transmit its own static IP address and a unique IP address of an X-ray detector 100 coupled with the coupling module 200, to the location determiner 310, according to a request from the location determiner 310, and the location determiner 310 may determine a location of the X-ray detector 100 based on the static IP address and the unique IP address.

Meanwhile, in FIG. 32, for convenience of description, a case in which there are a table coupling module 200-1, a stand coupling module 200-2, and a portable coupling module 200-3 has been described. However, the number of modules is not limited.

Components of the X-ray imaging apparatuses according to the above-described embodiments, and functions of the components have been described. Hereinafter, a control method of an X-ray imaging apparatus will be described with reference to a given flowchart. The X-ray imaging apparatus 1 described above with reference to FIGS. 1 to 33 can be applied to the control method of the X-ray imaging apparatus, and accordingly, the above descriptions can be applied to the control method of the X-ray imaging apparatus 1. In the following description, for convenience of description, it is assumed that the X-ray imaging apparatus 1 includes a radiography table 10, a radiography stand 20, and a portable coupling module 200-3.

Figure 34:
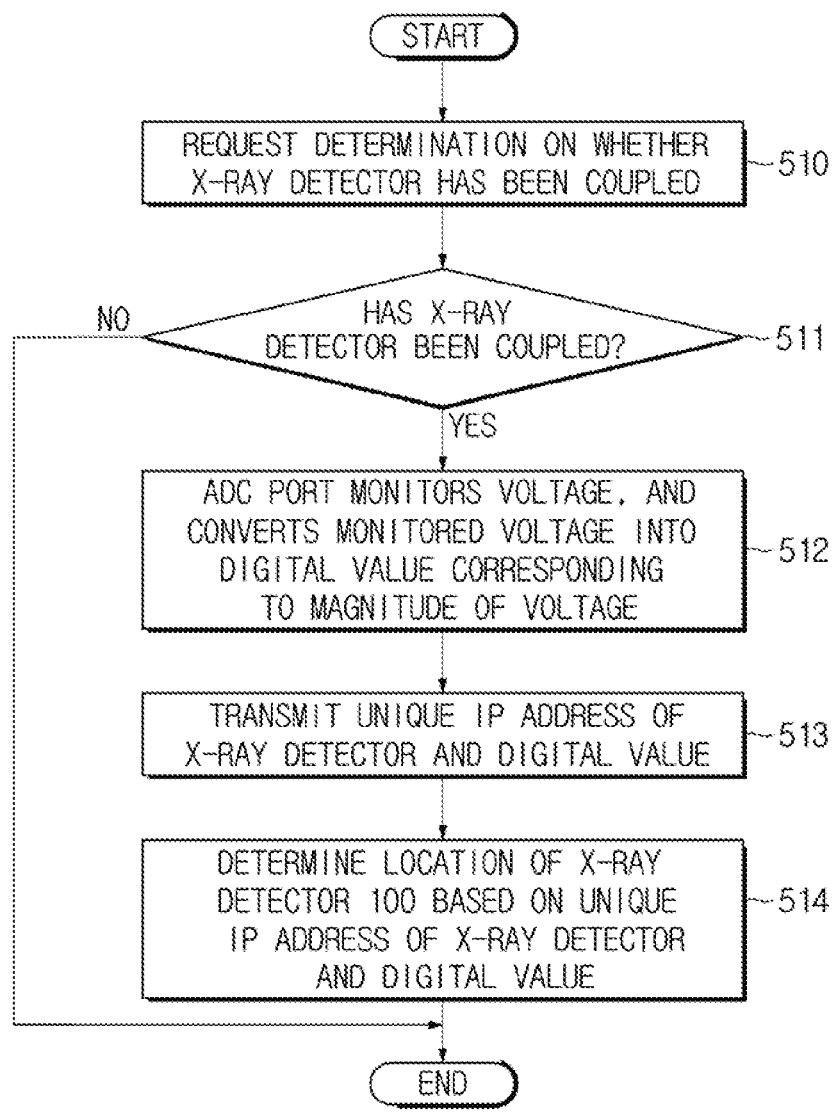
FIG. 34 is a flowchart illustrating a control method of an X-ray imaging apparatus, according to an embodiment of the present disclosure.

FIG. 34 is a flowchart illustrating a control method of an X-ray imaging apparatus, according to an embodiment of the present disclosure.

Referring to FIG. 34, the workstation 170 (see FIG. 1) may request determination on whether an X-ray detector has been connected, in operation 510. For example, the workstation 170 may transmit a Ping signal through the network hub 175, and request determination on whether there is an X-ray detector connected to the network hub 175.

If the X-ray detector 100 has been coupled with the table coupling module 200-1, the stand coupling module 200-2, or the portable coupling module 200-3, and connected to the network hub 175 through the coupling module ("Yes" in operation 511), the ADC port 181 may monitor a voltage, and convert the monitored voltage into a digital value corresponding to a magnitude of the voltage, in operation 512. As described above in the embodiment of FIG. 16 among embodiments of the X-ray imaging apparatus 1, if the X-ray detector 100 has been coupled with a coupling module 200, an electrical signal may be generated by an ID resistor included in the coupling module 200, and the ADC port 181 may monitor the electrical signal, that is, a voltage.

The X-ray detector 100 coupled with the coupling module 200 may transmit its own unique IP address and the digital value converted by the ADC port 181 to the workstation 170, in operation 513. For example, the unique IP address of the X-ray detector 100 and the digital value may be included in an ack signal responding to the Ping signal received from the workstation 170.

Thereafter, a location of the X-ray detector 100 may be determined based on the unique IP address of the X-ray detector 100 and the digital value, in operation 514. More specifically, the location determiner 310 of the workstation 170 may determine which X-ray detector 100 has been connected to the network hub 175, based on the received IP address, and determine a location of the X-ray detector 100, based on the received digital value. The ID resistors included in the respective coupling modules 200 may have different resistance values, and the location determiner 310 may know information about the resistance values. Accordingly, the location determiner 310 may determine which one of the plurality of coupling modules 200 the X-ray detector 100 has been coupled with, that is, which radiography mode of the table mode, the stand mode, and the portable mode the X-ray detector 100 is in, based on the digital value converted by the ADC port 181.

After which X-ray detector has been positioned at which location is determined, the corresponding X-ray detector may be set to a used X-ray detector. For example, it is assumed that there are three radiography modes of a table mode, a stand mode, and a portable mode, and there are three X-ray detectors of a first X-ray detector 100-1, a second X-ray detector 100-2, and a third X-ray detector 100-3. If the stand mode is selected as a radiography mode, and the location determiner 310 determines that the second X-ray detector 100-2 has been coupled with the stand coupling module 200-3 to be in the stand mode, the location determiner 310 may set the second X-ray detector 100-2 to a used X-ray detector to enable the workstation 170 to receive data from the second X-ray detector 100-2.

Also, if the X-ray source 70 can be automatically moved, the motor controller 340 may control the motor 110 to move the X-ray source 70 to a location corresponding to the X-ray detector 100-2.

Figure 35:
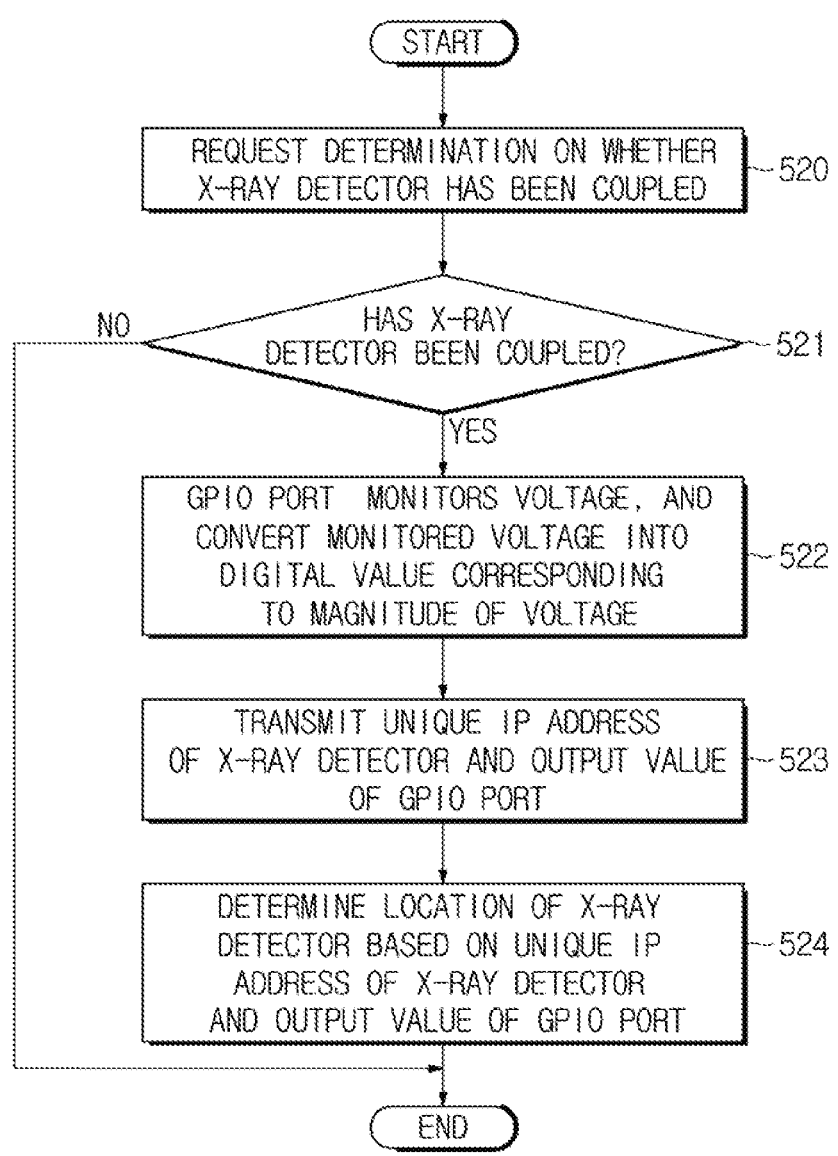
FIG. 35 is a flowchart illustrating a control method of an X-ray imaging apparatus, according to another embodiment of the present disclosure.

FIG. 35 is a flowchart illustrating a control method of an X-ray imaging apparatus, according to another embodiment of the present disclosure.

Referring to FIG. 35, the workstation 170 may request determination on whether an X-ray detector has been connected, in operation 520. For example, the workstation 170 may transmit a Ping signal through the network hub 175 to request determination on whether there is an X-ray detector connected to the network hub 175.

If the X-ray detector 100 has been coupled with the table coupling module 200-1, the stand coupling module 200-2, or the portable coupling module 200-3, and connected to the network hub 175 through the coupling module ("Yes" in operation 521), the GPIO port 182 may monitor a voltage, and convert the monitored voltage into a digital value corresponding to a magnitude of the voltage, in operation 522. As described above in the embodiment of FIG. 27 among embodiments of the X-ray imaging apparatus 1, if the X-ray detector 100 has been coupled with a coupling module 200, an electrical signal may be generated by an ID resistor included in the coupling module 200, and the GPIO port 182 may monitor the electrical signal, that is, a voltage.

The X-ray detector 100 coupled with the coupling module 200 may transmit its own unique IP address and the output value of the GPIO port 182 to the workstation 170, in operation 523. For example, the unique IP address of the X-ray detector 100 and the digital value may be included in an ack signal responding to the Ping signal received from the workstation 170.

Thereafter, a location of the X-ray detector 100 may be determined based on the unique IP address of the X-ray detector 100 and the output value of the GPIO port 182, in operation 524. More specifically, the location determiner 310 of the workstation 170 may determine which X-ray detector 100 has been connected to the network hub 175, based on the received IP address, and determine a location of the X-ray detector 100, based on the output value of the GPIO port 182. The ID resistors included in the respective coupling modules 200 may have different resistance values, and the location determiner 310 may know information about the resistance values. Herein, each ID resistor may be a pull-up resistor or a pull-down resistor. Accordingly, the location determiner 310 may determine which one of the plurality of coupling modules 200 the X-ray detector 100 has been coupled with, that is, which radiography mode of the table mode, the stand mode, and the portable mode the X-ray detector 100 is in, based on the output value of the GPIO port 182.

After which X-ray detector has been positioned at which location is determined, the corresponding X-ray detector may be set to a used X-ray detector. Since this operation has been described above, a detailed description thereof will be omitted.

Figure 36:
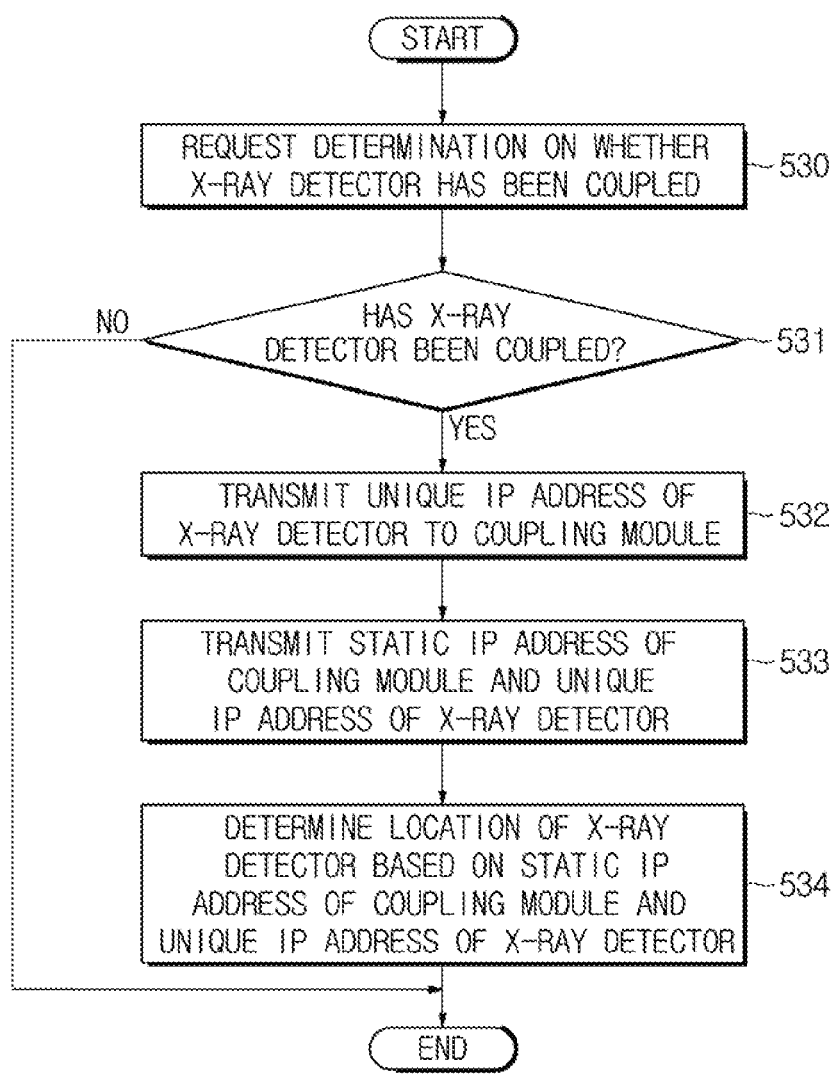
FIG. 36 is a flowchart illustrating a control method of an X-ray imaging apparatus, according to still another embodiment of the present disclosure.

FIG. 36 is a flowchart illustrating a control method of an X-ray imaging apparatus, according to still another embodiment of the present disclosure.

Referring to FIG. 36, the workstation 170 may request determination on whether an X-ray detector has been coupled, in operation 530. For example, the workstation 170 may transmit a Ping signal through the network hub 175 to request determination on whether there is an X-ray detector connected to the network hub 175.

If the X-ray detector 100 has been coupled with the table coupling module 200-1, the stand coupling module 200-2, or the portable coupling module 200-3, and connected to the network hub 175 through the coupling module ("Yes" in operation 531), the X-ray detector 100 may transmit its own unique IP address to the coupling module 200 with which the X-ray detector 100 has been coupled, in operation 532.

Then, the coupling module 200 may transmit its own static IP address and the unique IP address of the X-ray detector 100 with which the coupling module 200 has been coupled, to the workstation 170, in operation 533. The coupling module 200 may have its own static IP address, and the plurality of coupling modules 200 may have different static IP addresses. For example, if the coupling modules 200 include the table coupling module 200-1, the stand coupling module 200-2, and the portable coupling module 200-3, the three coupling modules 200-1, 200-2, and 200-3 may have different static IP addresses. The static IP address of each coupling module 200 may be assigned by the processor 221 included in the coupling module 200, or by the controller 300 of the workstation 170.

Then, a location of the X-ray detector 100 may be determined based on the static IP address of the coupling module 200 and the unique IP address of the X-ray detector 100, in operation 534. The location determiner 310 of the workstation 170 may determine which X-ray detector 100 has been coupled, based on the unique IP address of the X-ray detector 100 received from the coupling module 200, and determine which coupling module 200 the corresponding X-ray detector 100 has been coupled with, based on the static IP address of the coupling module 200. That is, the location determiner 310 may determine which X-ray detector 100 has been coupled with which coupling module 200 or which X-ray detector 100 is in which radiography mode.

Meanwhile, the controller 300 of the workstation 170 may set or change the IP address of the X-ray detector 100. This operation will be described with reference to FIGS. 37 to 42, below.

Figure 37:
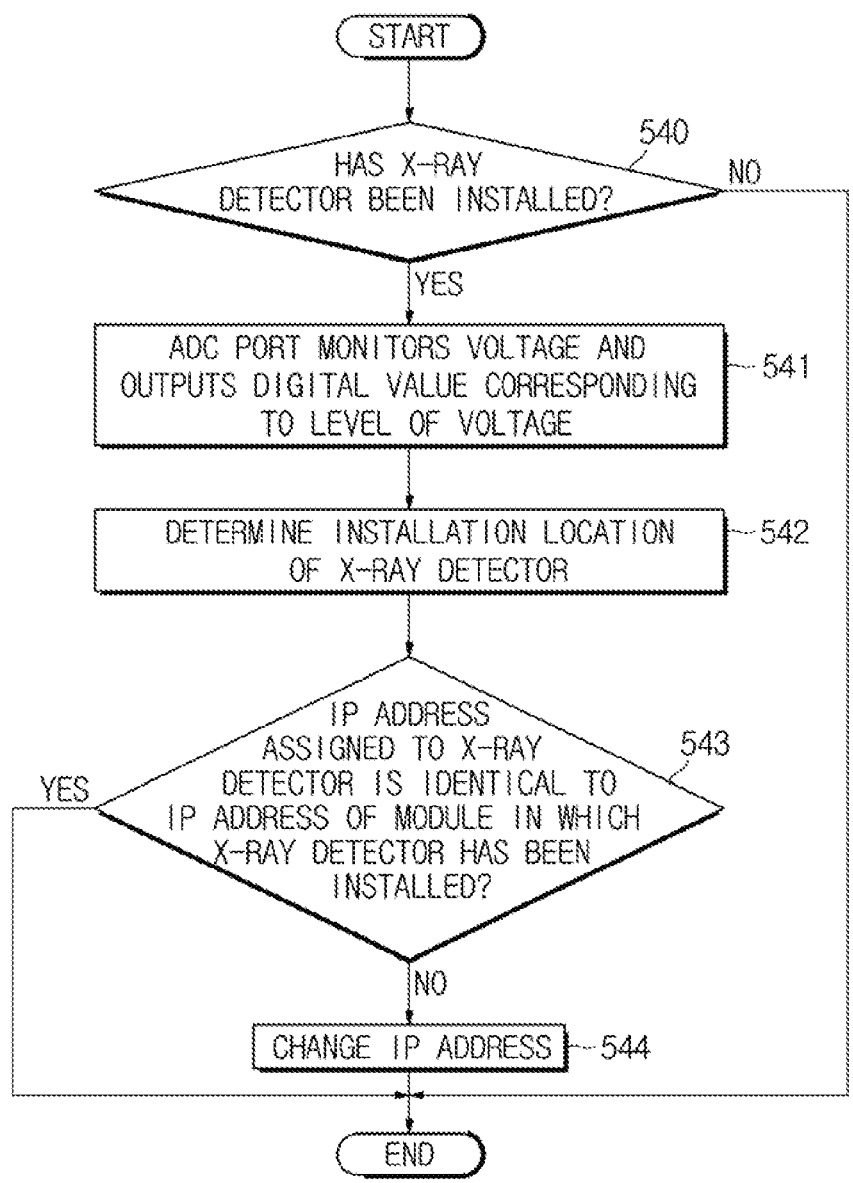
FIGS. 37 and 38 are flowcharts regarding a case in which a controller sets or changes an IP address of an X-ray detector, in the control method of the X-ray imaging apparatus according to the embodiment of the present disclosure.
Figure 38:
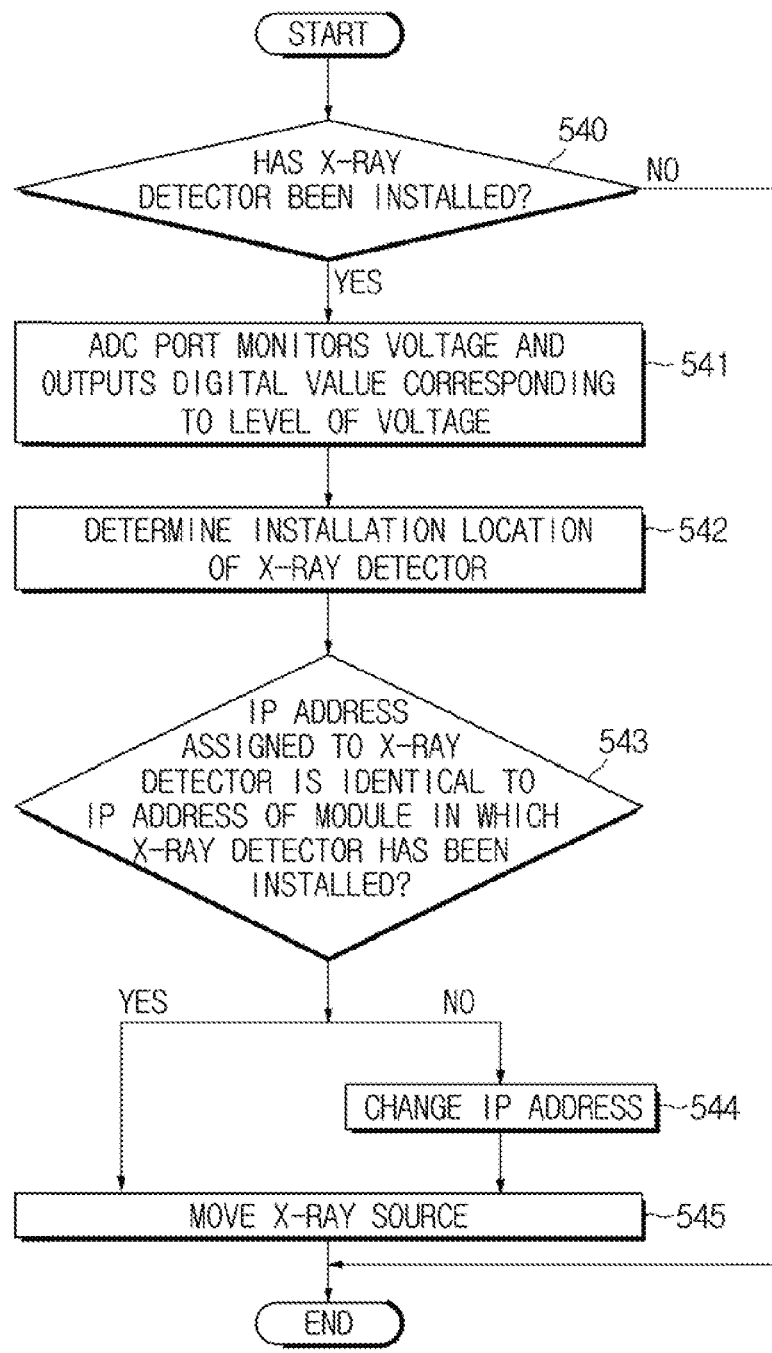

FIGS. 37 and 38 are flowcharts regarding a case in which the controller 300 sets or changes the IP address of the X-ray detector 100, in the control method of the X-ray imaging apparatus 1 according to the embodiment of the present disclosure;

In FIG. 37, the table coupling module 200-1, the stand coupling module 200-2, and the portable coupling module 200-3 are assumed to include different ID resistors.

The workstation 170 may determine whether the X-ray detector 100 has been installed, in operation 540.

More specifically, if the workstation 170 requests individual modules to determine whether the X-ray detector 100 has been installed therein, the modules wait for an ack signal from the X-ray detector 100. If a module that has received an ack signal from the X-ray detector 100 is found, the workstation 170 may determine that the X-ray detector 100 has been installed.

If no module that has received an ack signal from the X-ray detector 100 is found, the process terminates.

If the workstation 170 determines that the X-ray detector 100 has been installed, the ADC port 181 of the X-ray detector 100 may monitor a voltage applied to an ID check line, convert the monitored voltage into a digital value corresponding to a level of the voltage, and output the digital value to the location determiner 310, in operation 541.

The location determiner 310 may determine an installation location of the X-ray detector 100, based on the digital value output from the ADC port 181, in operation 542.

Because ID resistors included in the coupling modules 200 have different resistance values, a voltage that is monitored by the ADC port 181 varies depending on which module the X-ray detector 100 has been installed in. In other words, a value which the ADC port 181 outputs to the location determiner 310 varies depending on which module the X-ray detector 100 has been installed in. Accordingly, the location determiner 310 may determine an installation location of the X-ray detector 100 based on the digital value output from the ADC port 181.

The detector setting unit 320 may assign an IP address of a module in which the X-ray detector 100 has been installed, to the X-ray detector 100. If the X-ray detector 100 has already been assigned an IP address, the detector setting unit 320 may determine whether the IP address assigned to the X-ray detector 100 is identical to the IP address of the module in which the X-ray detector 100 has been installed, in operation 543.

If the detector setting unit 320 determines that the IP address assigned to the X-ray detector 100 is not identical to the IP address of the module in which the X-ray detector 100 has been installed, the detector setting unit 320 may change the IP address of the X-ray detector 100 to the IP address of the module in which the X-ray detector 100 has been installed, in operation 544.

Meanwhile, as shown in FIG. 38, after the location of the X-ray detector 100 is determined, the X-ray source 70 may move. If the detector setting unit 320 determines that the IP address assigned to the X-ray detector 100 is identical to the IP address of the module in which the X-ray detector 100 has been installed, or if the detector setting unit 320 changes the IP address of the X-ray detector 100 to the IP address of the module in which the X-ray detector 100 has been installed, the X-ray source 70 may move to correspond to the location of the X-ray detector 100, in operation 545.

More specifically, in a manual move mode, a user may apply power or torque to the handle 82 of the operating unit 80 (see FIG. 3) to move the X-ray source 70. In an automatic move mode, the user may set a radiography mode corresponding to an installation location of the X-ray detector 100, and according to the user's setting, the motor unit 110 may be driven to move the X-ray source 70.

Figure 39:
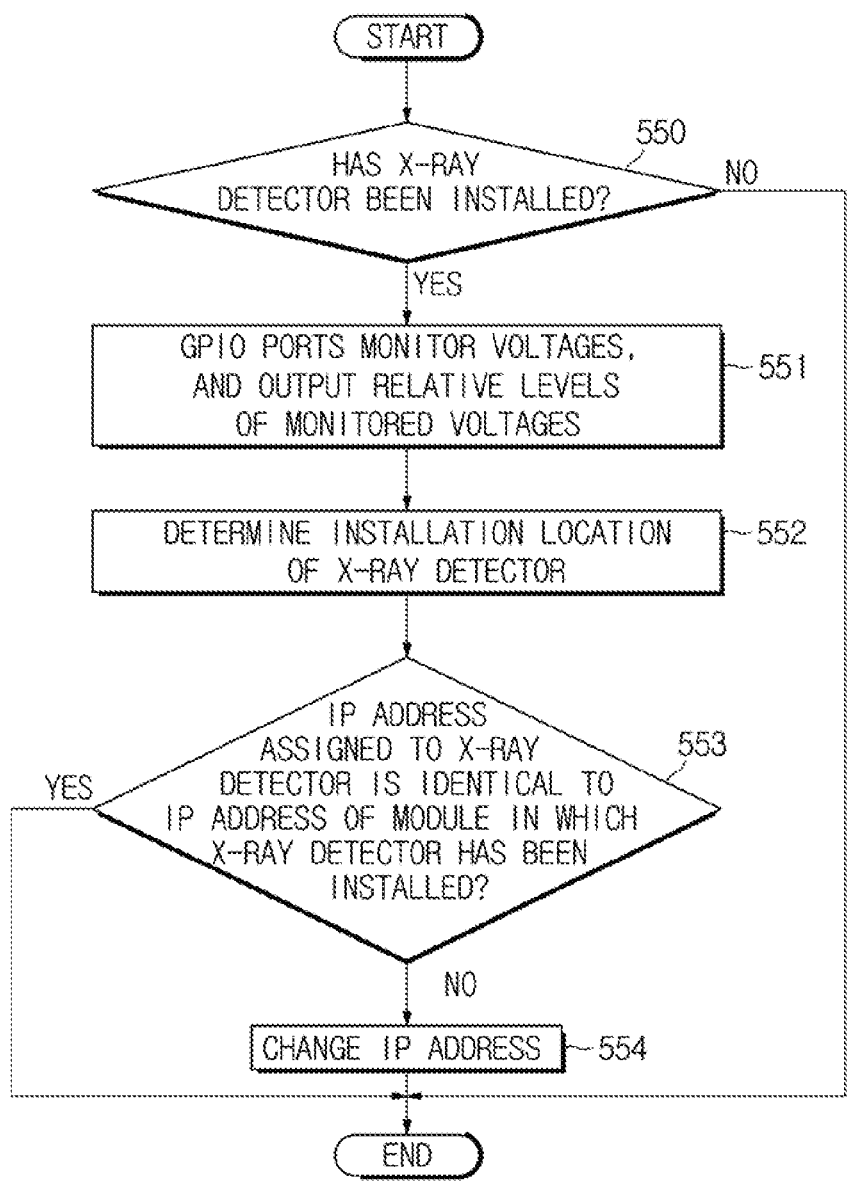
FIGS. 39 and 40 are flowcharts regarding a case in which a controller sets or changes an IP address of an X-ray detector, in the control method of the X-ray imaging apparatus according to the other embodiment of the present disclosure.
Figure 40:
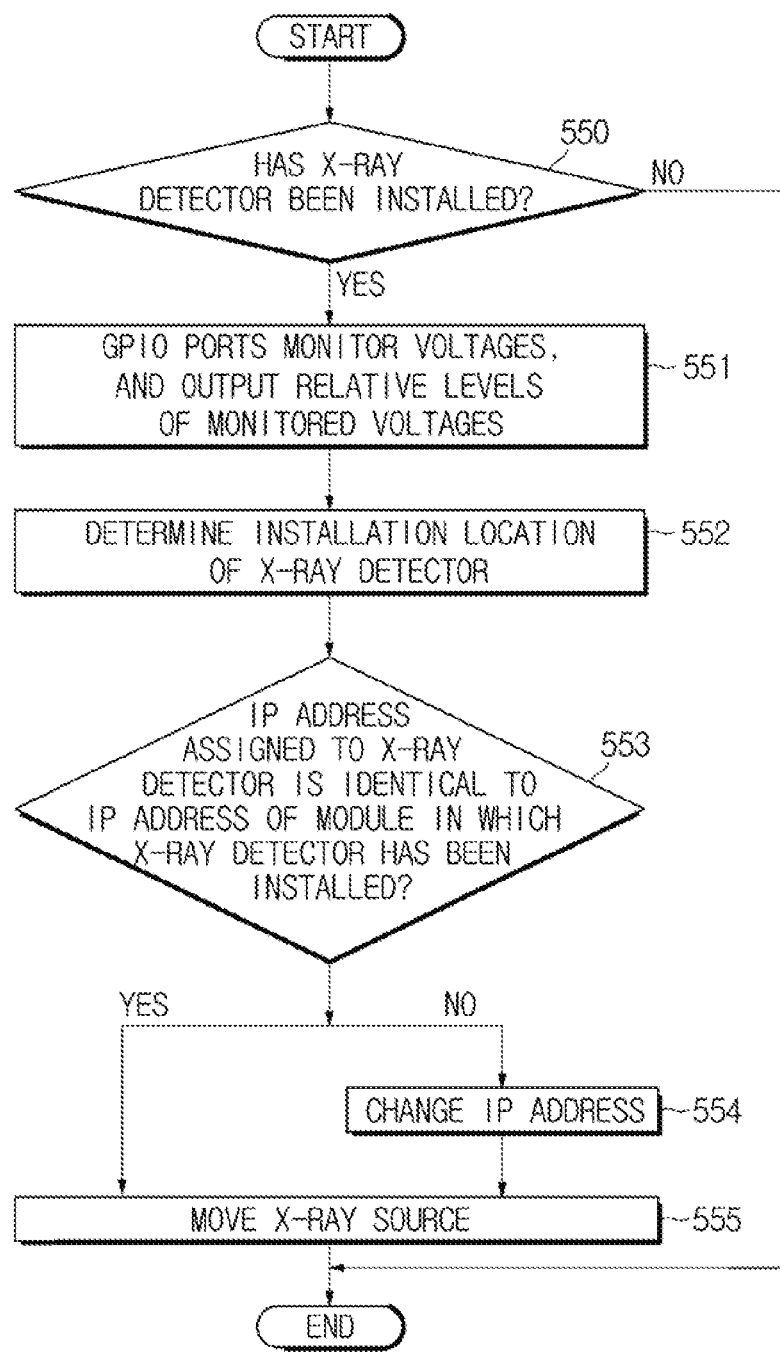

FIGS. 39 and 40 are flowcharts regarding a case in which the controller 300 sets or changes the IP address of the X-ray detector 100, in the control method of the X-ray imaging apparatus 1 according to the other embodiment of the present disclosure.

In the following description, descriptions of the same parts as in the above-described embodiment will be omitted.

In FIGS. 39 and 40, it is assumed that the X-ray detector 100 includes two GPIO ports 182, that is, a first GPIO port G1 and a second GPIO port G2, and each of the coupling modules 200-1, 200-2, and 200-3 includes two ID resistors. For example, as illustrated in FIG. 28, the table coupling module 200-1 includes two pull-up ID resistors that can be respectively connected to the first and second GPIO ports G1 and G2, the stand coupling module 200-2 includes a pull-up ID resistor that can be connected to the first GPIO port G1 and a pull-down ID resistor that can be connected to the second GPIO port G2, and the portable coupling module 200-3 includes two pull-down ID resistors that can be respectively connected to the first and second GPIO ports G1 and G2. The pull-up ID resistors and the pull-down ID resistors have the same resistance value. That is, the ID resistors included in the table coupling module 200-1 can be expressed as an ordered pair of two pull-up ID resistors $R_2$, the ID resistors included in the stand coupling module 200-2 can be expressed as an ordered pair of a pull-up ID resistor $R_2$ and a pull-down ID resistor $R_2$, and the ID resistors included in the portable coupling module 200-3 can be expressed as an ordered pair of two pull-down ID resistors $R_2$.

The workstation 170 may determine whether the X-ray detector 100 has been installed, in operation 550.

If the workstation 170 determines that no X-ray detector 100 has been installed, the process terminates.

If the workstation 170 determines that the X-ray detector 100 has been installed, the first GPIO port G1 and the second GPIO port G2 may monitor voltages applied to ID check lines, respectively. Then, the first GPIO port G1 and the second GPIO port G2 may output relative levels of the monitored voltages, respectively, to the location determiner 310, in operation 551.

The location determiner 310 may determine an installation location of the X-ray detector 100, based on the output values from the first and second GPIO ports G1 and G2 or an ordered pair of the output values from the first and second GPIO ports G1 and G2, in operation 552.

Because the ID resistors have a different configuration for each coupling module, voltages that are monitored by the first and second GPIO ports G1 and G2 vary depending on an installation location of the X-ray detector 100. In other words, values that are output from the first and second GPIO ports G1 and G2 to the location determiner 310, or an ordered pair of the output values from the first and second GPIO ports G1 and G2 may vary depending on which module the X-ray detector 100 has been installed in. Accordingly, the location determiner 310 may determine an installation location of the X-ray detector 100, based on output values of the first and second GPIO ports G1 and G2 or an ordered pair of output values of the first and second ports G1 and G2.

The detector setting unit 320 may assign an IP address of a module in which the X-ray detector 100 has been installed, to the X-ray detector 100. If the X-ray detector 100 has already been assigned an IP address, the detector setting unit 320 may determine whether the IP address assigned to the X-ray detector 100 is identical to the IP address of the module in which the X-ray detector 100 has been installed, in operation 553.

If the detector setting unit 320 determines that the IP address assigned to the X-ray detector 100 is not identical to the IP address of the module in which the X-ray detector 100 has been installed, the detector setting unit 320 may change the IP address of the X-ray detector 100 to the IP address of the module, in operation 554.

Meanwhile, as shown in FIG. 40, after the location of the X-ray detector 100 is determined, the X-ray source 70 may move.

If the detector setting unit 320 determines that the IP address assigned to the X-ray detector 100 is identical to the IP address of the module, or if the detector setting unit 320 changes the IP address of the X-ray detector 100 to the IP address of the module, the X-ray source 70 may move to correspond to the location of the X-ray detector 100, in operation 555.

Figure 41:
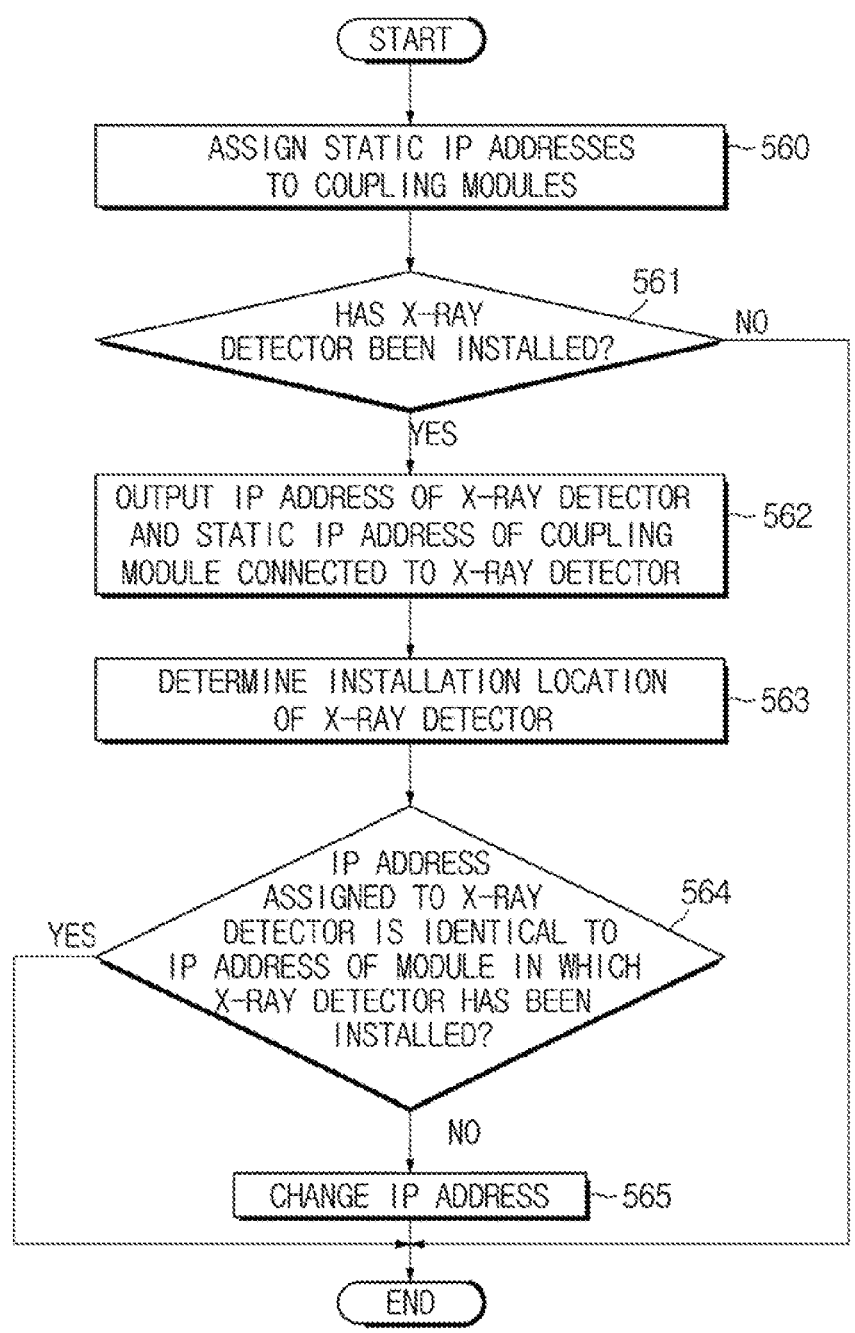
FIGS. 41 and 42 are flowcharts regarding a case in which a controller sets or changes an IP address of an X-ray detector, in the control method of the X-ray imaging apparatus according to the still another embodiment of the present disclosure.
Figure 42:
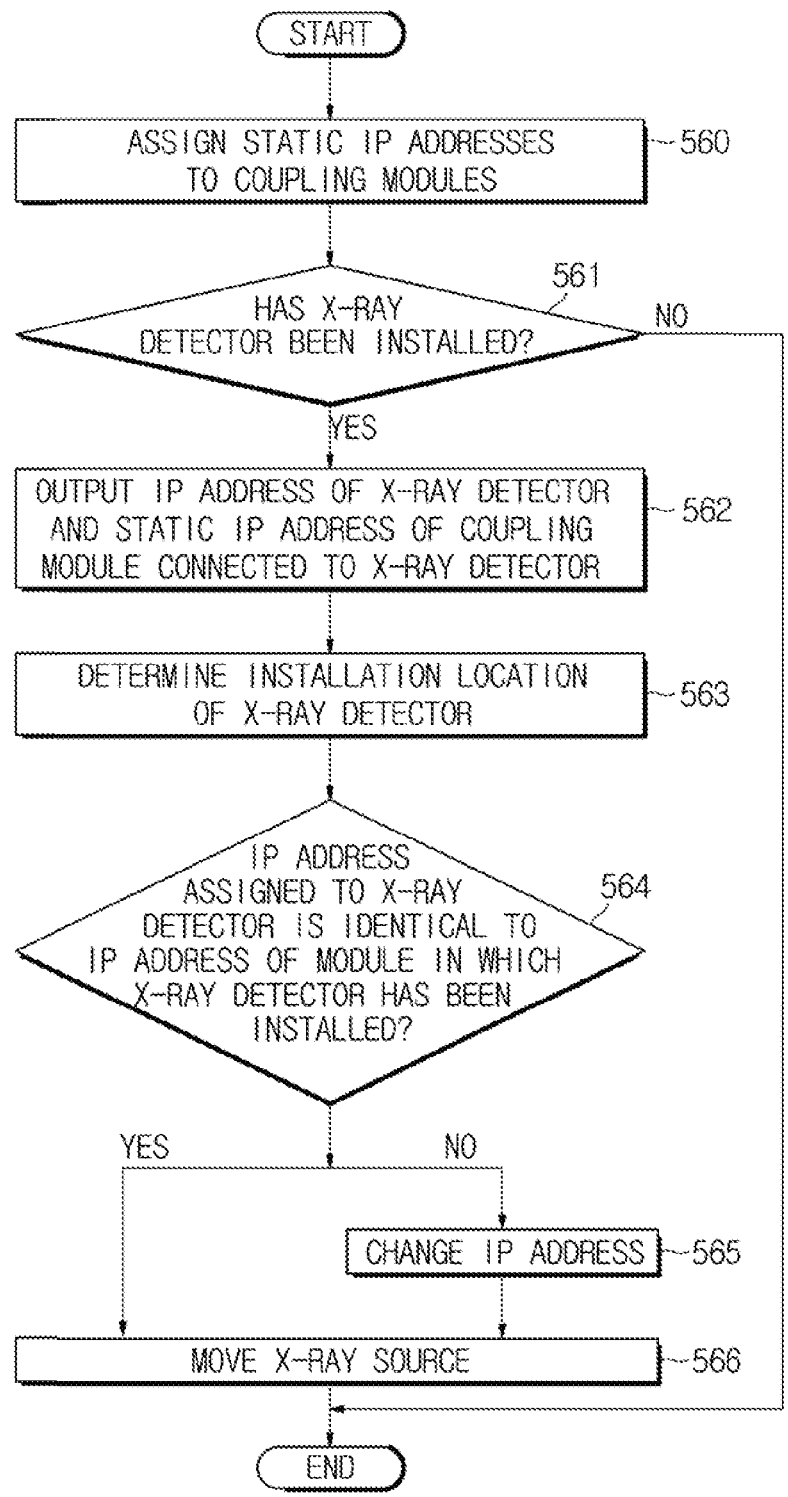

FIGS. 41 and 42 are flowcharts regarding a case in which the controller 300 sets or changes an IP address of the X-ray detector 100, in the control method of the X-ray imaging apparatus 1 according to the still another embodiment of the present disclosure. In the following description, descriptions of the same parts as in the above-described embodiment will be omitted.

First, the detector setting unit 320 may assign an IP address to the X-ray detector 100. Then, the coupling module IP setting unit 330 may assign static IP addresses to the first, second, and third coupling modules 200-1, 200-2, and 200-3, in operation 560. That is, IP addresses assigned to the first, second, and third coupling modules 200-1, 200-2, and 200-3 do not change. Also, the static IP addresses respectively assigned to the first, second, and third coupling modules 200-1, 200-2, and 200-3 are different values. Also, each of the first, second, and third coupling modules 200-1, 200-2, and 200-3 may assign its own static IP address.

After the static IP addresses are assigned to the first, second, and third coupling modules 200-1, 200-2, and 200-3, the workstation 170 may determine whether the X-ray detector has been installed, in operation 561.

More specifically, if the workstation 170 requests individual modules to determine whether the X-ray detector 100 has been installed therein, the modules wait an ack signal from the X-ray detector 100. If a module that has received acknowledge from the X-ray detector 100 is found, the workstation 170 may determine that the X-ray detector 100 has been installed. The module that has received an ack signal from the X-ray detector 100 is referred to as a module M.

If the workstation 170 determines that no X-ray detector 100 has been installed, the process terminates.

If the workstation 170 determines that the X-ray detector 100 has been installed, the module M may output an IP address of the X-ray detector 100 and a static IP address of the coupling module 200 connected to the X-ray detector 100, in operation 562. More specifically, the module M that has received an ack signal from the X-ray detector 100 may request the X-ray detector 100 to send an IP address, and receive an IP address from the X-ray detector 100. Then, the module M may transmit the IP address of the X-ray detector 100 and the static IP address of the coupling module 200 connected to the X-ray detector 100, that is, the static IP address of the coupling module 200 included in the module M to the workstation 170.

The location determiner 310 may determine an installation location of the X-ray detector 100 based on the IP addresses received from the module M, in operation 563.

For example, if the IP address of the X-ray detector 100 is an IP address for the radiography stand 20, and the static IP address of the coupling module is an IP address for the radiography table 10, the location determiner 310 may determine that the X-ray detector 100 has been installed in the radiography table 10.

Thereafter, the detector setting unit 320 may determine whether the IP address of the X-ray detector 100 is identical to an IP address of a module in which the X-ray detector 100 has been installed, in operation 564.

If the detector setting unit 320 determines that the IP address of the X-ray detector 100 is not identical to the IP address of the module, the detector setting unit 320 may change the IP address of the X-ray detector 100 to the IP address of the module, in operation 565. Because the IP address of the X-ray detector 100 is an IP address for the radiography stand 20, and a module in which the X-ray detector 100 has been installed is the radiography table 10, the detector setting unit 320 may change the IP address of the X-ray detector 100 to the IP address for the radiography table 10 so that the X-ray detector 100 can detect X-rays in the radiography table 10.

Meanwhile, as shown in FIG. 42, after the location of the X-ray detector 100 is determined, the X-ray source 70 may move.

If the detector setting unit 320 determines that the IP address of the X-ray detector 100 is identical to the IP address of the module, or if the detector setting unit 320 changes the IP address of the X-ray detector 100 to the IP address for the radiography table 10, the X-ray source 70 may move to correspond to the location of the X-ray detector 100, in operation 566.

The above-described embodiments may be recorded in computer-readable media including program instructions to implement various operations embodied by a computer. The media may also include, alone or in combination with the program instructions, data files, data structures, and the like. The program instructions recorded on the media may be those specially designed and constructed for the purposes of embodiments, or they may be of the kind well-known and available to those having skill in the computer software arts. Examples of computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. The computer-readable media may also be a distributed network, so that the program instructions are stored and executed in a distributed fashion. The program instructions may be executed by one or more processors. The computer-readable media may also be embodied in at least one application specific integrated circuit (ASIC) or Field Programmable Gate Array (FPGA), which executes (processes like a processor) program instructions. Examples of program instructions include both machine code, such as produced by a compiler, and files containing higher level code that may be executed by the computer using an interpreter. The above-described devices may be configured to act as one or more software modules in order to perform the operations of the above-described embodiments, or vice versa.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An X-ray imaging apparatus comprising:
    an X-ray source configured to irradiate X-rays;
    an X-ray detector configured to detect the irradiated X-rays;
    a controller; and
    a plurality of coupling modules, each coupling module of the plurality of coupling modules having a static Information Provider (IP) address and being coupleable with the X-ray detector such that the coupling module enables the controller to communication with the X-ray detector,
    wherein the controller is configured to determine a respective coupling module of the plurality of coupling modules with which the X-ray detector is coupled, based on the static IP address of the respective coupling module having been transmitted from the X-ray detector.

2. The X-ray imaging apparatus according to claim 1, wherein each coupling module of the plurality of coupling modules is configured to be connected with the controller and a power supply unit.

3. The X-ray imaging apparatus according to claim 2, wherein the respective coupling module is configured to supply a voltage to the X-ray detector, and enable communications between the X-ray detector and the controller.

4. The X-ray imaging apparatus according to claim 1, wherein
    the controller is configured to assign the static IP addresses to the plurality of coupling modules, respectively, or
    each coupling module of the plurality of coupling modules is configured to assign its own static IP address.

5. The X-ray imaging apparatus according to claim 1, wherein the X-ray detector is configured to transmit the static IP address of the respective coupling module with which the X-ray detector is coupled and a unique IP address of the X-ray detector to the controller.

6. The X-ray imaging apparatus according to claim 5, wherein the controller is configured to identify the X-ray detector after being coupled with the respective coupling module based on the unique IP address.

7. The X-ray imaging apparatus according to claim 5, wherein the controller is configured to maintain or change the unique IP address of the X-ray detector in correspondence with the respective coupling module after the respective coupling module is coupled with the X-ray detector.

8. The X-ray imaging apparatus according to claim 1, wherein the controller is configured to move the X-ray source to correspond to a location of the X-ray detector.

9. A control method of an X-ray imaging apparatus that includes an X-ray source configured to irradiate X-rays, a controller and a plurality of coupling modules, each coupling module of the plurality of coupling modules having a static Information Provider (IP) address and being coupleable with an X-ray detector detecting the irradiated X-rays such that the controller communicates with the X-ray detector, the method comprising:

receiving, from the X-ray detector, the static IP address of a respective coupling module of the plurality of coupling modules with which the X-ray detector is coupled; and determining the respective coupling module with which the X-ray detector is coupled, based on the received static IP address.

10. The control method according to claim 9, further comprising:

assigning, by the controller, the static IP addresses to the plurality of coupling modules, respectively, or assigning, by each coupling module of the plurality of coupling modules, its own static IP address.

11. The control method according to claim 9, further comprising:

receiving a unique IP address of the X-ray detector from the X-ray detector after the X-ray detector is coupled with the respective coupling module.

12. The control method according to claim 11, further comprising:

identifying the X-ray detector after being coupled with the respective coupling module based on the unique IP address.

13. The control method according to claim 11, further comprising, maintaining or changing the unique IP address of the X-ray detector in correspondence to the respective coupling module with which the X-ray detector is coupled.

14. The control method according to claim 9, further comprising:

moving the X-ray source to correspond to a location of the X-ray detector after the X-ray detector is coupled with the respective coupling module.

15. An X-ray imaging apparatus comprising:

an X-ray source configured to irradiate X-rays;

a controller; and a plurality of coupling modules, each coupling module of the plurality of coupling modules having a static Information Provider (IP) address and being coupleable with each X-ray detector of a plurality of X-ray detectors that are configured to detect the irradiated X-rays, to enable communication between a coupled X-ray detector and the controller, wherein the controller is configured to determine a respective coupling module of the plurality of coupling modules with which a respective X-ray detector of the plurality of X-ray detectors has been coupled, based on the static IP address of the respective coupling module having been transmitted from the respective X-ray detector.

* * * * *